(12) United States Patent
Pasqualini et al.

(10) Patent No.: US 12,103,966 B2
(45) Date of Patent: Oct. 1, 2024

(54) GRP78-BINDING ANTIBODIES AND USES THEREOF IN DETECTING OR NEUTRALIZING GRP78

(71) Applicant: Rutgers, The State University of New Jersey, New Brunswick, NJ (US)

(72) Inventors: Renata Pasqualini, New Brunswick, NJ (US); Wadih Arap, New Brunswick, NJ (US); Fernanda Iamassaki Staquicini, New Brunswick, NJ (US); Fortunato Ferrara, Santa Fe, NM (US); Sara D'Angelo, Santa Fe, NM (US); Andrew R. M. Bradbury, Santa Fe, NM (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 92 days.

(21) Appl. No.: 17/837,888

(22) Filed: Jun. 10, 2022

(65) Prior Publication Data
US 2022/0348680 A1   Nov. 3, 2022

Related U.S. Application Data

(60) Continuation of application No. 17/592,828, filed on Feb. 4, 2022, which is a division of application No. 16/333,898, filed as application No. PCT/US2017/052661 on Sep. 21, 2017, now Pat. No. 11,254,751.

(60) Provisional application No. 62/397,521, filed on Sep. 21, 2016, provisional application No. 62/397,512, filed on Sep. 21, 2016.

(51) Int. Cl.
| C07K 16/18 | (2006.01) |
| A61K 39/395 | (2006.01) |
| A61K 47/68 | (2017.01) |
| A61P 35/00 | (2006.01) |
| C07K 16/30 | (2006.01) |
| G01N 33/574 | (2006.01) |
| A61K 38/07 | (2006.01) |
| A61K 39/00 | (2006.01) |
| A61K 49/00 | (2006.01) |
| C07K 14/47 | (2006.01) |
| C07K 16/00 | (2006.01) |
| C07K 16/28 | (2006.01) |
| C12N 15/10 | (2006.01) |
| C12N 15/64 | (2006.01) |
| C12Q 1/6869 | (2018.01) |
| G01N 33/50 | (2006.01) |

(52) U.S. Cl.
CPC .......... *C07K 16/18* (2013.01); *A61K 39/3955* (2013.01); *A61K 39/39558* (2013.01); *A61K 47/6803* (2017.08); *A61K 47/68031* (2023.08); *A61K 47/68033* (2023.08); *A61P 35/00* (2018.01); *C07K 16/30* (2013.01); *C07K 16/3023* (2013.01); *G01N 33/574* (2013.01); *A61K 38/07* (2013.01); *A61K 2039/505* (2013.01); *A61K 47/6817* (2017.08); *A61K 47/6843* (2017.08); *A61K 47/6849* (2017.08); *A61K 47/6891* (2017.08); *A61K 49/0008* (2013.01); *C07K 14/47* (2013.01); *C07K 16/005* (2013.01); *C07K 16/28* (2013.01); *C07K 16/2866* (2013.01); *C07K 2317/21* (2013.01); *C07K 2317/35* (2013.01); *C07K 2317/55* (2013.01); *C07K 2317/622* (2013.01); *C07K 2317/73* (2013.01); *C07K 2317/77* (2013.01); *C12N 15/1037* (2013.01); *C12N 15/64* (2013.01); *C12N 2810/00* (2013.01); *C12Q 1/6869* (2013.01); *G01N 33/5011* (2013.01); *G01N 33/57423* (2013.01)

(58) Field of Classification Search
CPC .... C07K 16/18; C07K 16/30; A61K 39/3955; A61K 39/39558; A61P 35/00
See application file for complete search history.

(56) References Cited

U.S. PATENT DOCUMENTS

| 10,259,884 B2 | 4/2019 | Hallahan et al. |
| 10,851,161 B2 | 12/2020 | Gill et al. |
| 2004/0208877 A1 | 10/2004 | Levanon et al. |
| 2010/0041074 A1 | 2/2010 | Kimura |
| 2022/0306763 A1 | 9/2022 | Pasqualini et al. |
| 2023/0028927 A1 | 1/2023 | Pasqualini et al. |
| 2023/0139913 A1 | 5/2023 | Pasqualini et al. |

FOREIGN PATENT DOCUMENTS

| WO | 2013040472 A2 | 3/2013 |
| WO | 2014153056 A2 | 9/2014 |

OTHER PUBLICATIONS

Nagelkerke et al (2014. Biochimica et Biophysica Acta 1846: 277-284).*

(Continued)

*Primary Examiner* — Zachary C Howard
(74) *Attorney, Agent, or Firm* — Saul Ewing LLP; Domingos J. Silva; Lukas Pfannenstiel

(57) ABSTRACT

Isolated or recombinant EphA5 or GRP78 targeting antibodies are provided. In some cases, antibodies of the embodiments can be used for the detection, diagnosis and/or therapeutic treatment of human diseases, such as cancer. A method of rapidly identifying antibodies or antibody fragments for the treatment of cancer using a combination of in vitro and in vivo methodologies is also provided.

26 Claims, 37 Drawing Sheets
Specification includes a Sequence Listing.

(56) References Cited

OTHER PUBLICATIONS

Arap, et al., "Cell surface expression of the stress response chaperone GRP78 enables tumor targeting by circulating ligands", Cancer Cell, vol. 6, 2004, pp. 275-284.

Bowley, R.D., "Libraries against libraries for combinatorial selection of replicating antigen-antibody pairs", PNAS, 106(5), 2009, pp. 1380-1385.

Daneshmand, et al., "Glucose-regulated protein GRP78 is upregulated in prostate cancer and correlates with recurrence and survival", Human Pathology, vol. 38, 2007, pp. 1547-1552.

D'Angelo, et al., "Selection of phage-displayed accessible recombinant targeted antibodies (SPARTA): methodology and applications", JCI Insight, 3(9), 2018, pp. e98305, 12 pages.

Frenzel, et al., "Construction of Human Antibody Gene Libraries and Selection of Antibodies by Phage Display", Human Monoclonal Antibodies: Methods and Protocols, Methods in Molecular Biology, vol. 1060, Chapter 12, 2014, pp. 215-243.

Harpley, C.J., "Optimization of Methods for Phage Display Using Single-Chain Variable Fragment Phagemid libraries", A thesis presented to the graduate school of the University of Florida in partial fulfillment of the requirements for the degree of Master of Science, University of Florida, 2008, pp. 97.

Lee, A.S., "Glucose regulated proteins in cancer: molecular mechanisms and therapeutic potential", Nat Rev Cancer, 14(4), 2014, pp. 263-276.

Lee, et al., "GRP78 as a Novel Predictor of Responsiveness to Chemotherapy in Breast Cancer", Cancer Res, 66(16), 2006, pp. 7849-7853.

Mandelin, et al., "Selection and identification of ligand peptides targeting a model of castrate-resistant osteogenic prostate cancer and their receptors", PNAS, 112(12), 2015, pp. 3776-3781.

Miao, et al., "Inhibition of Established Micrometastases by Targeted Drug Delivery via Cell Surface-Associated GRP78", Clin Cancer Res, 19(8), 2013, pp. 2107-2116.

Pilch, et al., "Peptides selected for binding to clotted plasma accumulate in tumor stroma and wounds", PNAS, 103(8), 2006, pp. 2800-2804.

Sato, et al., "GRP78 Signaling Hub: A Receptor for Targeted Tumor Therapy", Advances in Genetics, vol. 69, 2010, pp. 97-114.

Staquicini, et al., "Receptor Tyrosine Kinase EphA5 is a Functional Molecular Target in Human Lung Cancer", J Biol Chem, 290(12), 2015, pp. 7345-7359.

Tikunova, N.V., "i dr. Fagovyi displei na osnove nitchatykh bacteriofagov: primenie dlya othora recombinantnykh antitel", Acta Naturae, No. 3, 2009, pp. ss 22-31.

Wiersma, et al., "Mechanisms of translocation of ER chaperones to the cell surface and immunomodulatory roles in cancer and autoimmunity", Frontiers in Oncology, 5(7), 2015, pp. 1-14.

Sanchez-Martin, et al., "Proteasome activator complex PA28 identified as an accessible target in prostate cancer by in vivo selection of human antibodies", PNAS, 110(34), Aug. 20, 2013, pp. 13791-13796.

Sanchez-Martin, et al., "Proteasome activator complex PA28 identified as an accessible target in prostate cancer by in vivo selection of human antibodies, Supporting Information", PNAS, 110, 2014, pp. 1-24.

Sanchez-Martin, et al., "Selection strategies for anticancer antibody discovery: searching off the beaten path", Trends in Biotechnology, 33(5), 2015, pp. 292-301.

Ueberberg, et al., "Phage library-screening: A powerful approach for generation of targeting-agents specific for normal pancreatic islet-cells and islet-cell carcinoma in vivo", Regulatory Peptides, vol. 160, 2010, pp. 1-8.

\* cited by examiner

FIG. 22

HCDR3 sequences for anti-EphA5 and
anti-GRP78 monoclonals

| Clone | HCDR3 sequence | SEQ ID |
|---|---|---|
| Anti-EphA5 (E1) | CATHAAAGDYW | SEQ ID NO: 64 |
| Anti-EphA5 (E2) | CARVAAAGDYW | SEQ ID NO: 65 |
| Anti-EphA5 (E3) | CAREGAFGGRK | SEQ ID NO: 66 |
| Anti-EphA5 (E4) | CAREIWSGYAYFDLW | SEQ ID NO: 67 |
| Anti-GRP78 (G1) | CARYSSIDAFEIW | SEQ ID NO: 68 |
| Anti-GRP78 (G2) | CARDPYYYDSSGYYYFDAFGIW | SEQ ID NO: 69 |
| Anti-GRP78 (G3) | CARDPYYYDSSGYYYFDAFDIW | SEQ ID NO: 70 |

SEQUENCE LISTING

<160> NUMBER OF SEQ ID NOS: 70

<210> SEQ ID NO 1
<211> LENGTH: 117
<212> TYPE: PRT
<213> ORGANISM: Homo Sapiens

<400> SEQUENCE: 1

Thr Gln Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Val Arg Gln Ala Pro Gly Lys Gly Leu Glu Trp
        35                  40                  45

Val Ser Ala Ile Ser Gly Ser Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Thr His Ala Ala Ala Gly Asp Tyr Trp Gly Gln Gly Thr Leu
            100                 105                 110

Val Thr Val Ser Ser
        115

<210> SEQ ID NO 2
<211> LENGTH: 108
<212> TYPE: PRT
<213> ORGANISM: Homo Sapiens

<400> SEQUENCE: 2

Ser Tyr Glu Leu Ile Gln Pro Pro Ser Val Ser Val Ala Pro Gly Gln
1               5                   10                  15

Thr Ala Arg Ile Thr Cys Gly Gly Ser Asn Ile Arg Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Arg Thr Lys Val Thr Val Leu
            100                 105

<210> SEQ ID NO 3
<211> LENGTH: 10
<212> TYPE: PRT
<213> ORGANISM: Homo sapiens

<400> SEQUENCE: 3

Gly Phe Thr Phe Ser Ser Tyr Ala Met Ser
1               5                   10

<210> SEQ ID NO 4
<211> LENGTH: 17
<212> TYPE: PRT
<213> ORGANISM: Homo Sapiens

<400> SEQUENCE: 4

Ala Ile Ser Gly Ser Gly Gly Ser Thr Tyr Tyr Ala Asp Ser Val Lys
1               5                   10                  15

Gly

<210> SEQ ID NO 5
<211> LENGTH: 7
<212> TYPE: PRT
<213> ORGANISM: Homo Sapiens

<400> SEQUENCE: 5

His Ala Ala Ala Gly Asp Tyr
1               5

<210> SEQ ID NO 6
<211> LENGTH: 11
<212> TYPE: PRT
<213> ORGANISM: Homo Sapiens

<400> SEQUENCE: 6

Gly Gly Ser Asn Ile Arg Ser Lys Ser Val His
1               5                   10

<210> SEQ ID NO 7
<211> LENGTH: 7
<212> TYPE: PRT

-continued

<213> ORGANISM: Homo Sapiens

<400> SEQUENCE: 7

Asp Asp Ser Asp Arg Pro Ser
1               5

<210> SEQ ID NO 8
<211> LENGTH: 11
<212> TYPE: PRT
<213> ORGANISM: Homo Sapiens

<400> SEQUENCE: 8

Gln Val Trp Asp Ser Ser Ser Asp His Trp Val
1               5                   10

<210> SEQ ID NO 9
<211> LENGTH: 116
<212> TYPE: PRT
<213> ORGANISM: Homo Sapiens

<400> SEQUENCE: 9

Thr Gln Val Gln Leu Val Glu Thr Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Val Arg Gln Ala Pro Gly Lys Gly Leu Glu Trp
        35                  40                  45

Val Ser Ala Ile Ser Gly Ser Gly Gly Ser Thr Tyr Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Val Ala Ala Gly Asp Tyr Trp Gly Gln Gly Thr Leu Val
            100                 105                 110

Thr Val Ser Ser
        115

<210> SEQ ID NO 10
<211> LENGTH: 110
<212> TYPE: PRT
<213> ORGANISM: Homo Sapiens

<400> SEQUENCE: 10

Ser Tyr Glu Leu Thr Gln Pro Pro Ser Val Ser Val Ala Pro Gly Lys
1               5                   10                  15

Thr Ala Arg Ile Thr Cys Glu Gly Asn Asn Ile Gly Ser Lys Gly Val
            20                  25                  30

His Trp Tyr Gln Gln Lys Pro Gly Gln Ala Pro Ala Leu Val Val Tyr
        35                  40                  45

Asp Gly Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Asn Tyr Val Phe Gly Thr Arg Thr Lys Leu Thr Val Leu
            100                 105                 110

```
<210> SEQ ID NO 11
<211> LENGTH: 10
<212> TYPE: PRT
<213> ORGANISM: Homo Sapiens

<400> SEQUENCE: 11

Gly Phe Thr Phe Ser Ser Tyr Ala Met Ser
1               5                   10

<210> SEQ ID NO 12
<211> LENGTH: 17
<212> TYPE: PRT
<213> ORGANISM: Homo Sapiens

<400> SEQUENCE: 12

Ala Ile Ser Gly Ser Gly Gly Ser Thr Tyr Tyr Ala Asp Ser Val Lys
1               5                   10                  15

Gly

<210> SEQ ID NO 13
<211> LENGTH: 6
<212> TYPE: PRT
<213> ORGANISM: Homo sapiens

<400> SEQUENCE: 13

Val Ala Ala Gly Asp Tyr
1               5

<210> SEQ ID NO 14
<211> LENGTH: 11
<212> TYPE: PRT
<213> ORGANISM: Homo Sapiens

<400> SEQUENCE: 14

Glu Gly Asn Asn Ile Gly Ser Lys Gly Val His
1               5                   10

<210> SEQ ID NO 15
<211> LENGTH: 7
<212> TYPE: PRT
<213> ORGANISM: Homo Sapiens

<400> SEQUENCE: 15

Asp Gly Ser Asp Arg Pro Ser
1               5

<210> SEQ ID NO 16
<211> LENGTH: 13
<212> TYPE: PRT
<213> ORGANISM: Homo Sapiens

<400> SEQUENCE: 16

Gln Val Trp Asp Asn Ser Ser Asp His Pro Asn Tyr Val
1               5                   10

<210> SEQ ID NO 17
<211> LENGTH: 117
<212> TYPE: PRT
<213> ORGANISM: Homo Sapiens

<400> SEQUENCE: 17

Thr Gln Val Gln Leu Val Glu Ser Gly Gly Gly Leu Val Gln Pro Gly
1               5                   10                  15
```

Gly Ser Leu Arg Leu Ser Cys Ala Ala Ser Gly Phe Ala Phe Ser Asn
            20                  25                  30

Tyr Ala Met Ser Trp Val Arg Gln Ala Pro Gly Lys Gly Leu Glu Trp
            35                  40                  45

Val Ser Gly Ile Ser Gly Ser Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Glu Gly Ala Phe Gly Gly Arg Lys Gly Gln Gly Thr Leu
            100                 105                 110

Val Thr Val Ser Ser
        115

<210> SEQ ID NO 18
<211> LENGTH: 112
<212> TYPE: PRT
<213> ORGANISM: Homo Sapiens

<400> SEQUENCE: 18

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Val Asp Trp Tyr Leu Gln Lys Pro Gly Gln Pro
            35                  40                  45

Pro His Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Asp Pro Arg Thr Phe Gly Gln Gly Thr Lys Val Glu Ile Lys
            100                 105                 110

<210> SEQ ID NO 19
<211> LENGTH: 10
<212> TYPE: PRT
<213> ORGANISM: Homo Sapiens

<400> SEQUENCE: 19

Gly Phe Ala Phe Ser Asn Tyr Ala Met Ser
1               5                   10

<210> SEQ ID NO 20
<211> LENGTH: 17
<212> TYPE: PRT
<213> ORGANISM: Homo Sapiens

<400> SEQUENCE: 20

Gly Ile Ser Gly Ser Gly Gly Ser Thr Tyr Tyr Ala Asp Ser Val Lys
1               5                   10                  15

Gly

<210> SEQ ID NO 21
<211> LENGTH: 8
<212> TYPE: PRT
<213> ORGANISM: Homo Sapiens

```
<400> SEQUENCE: 21

Glu Gly Ala Phe Gly Gly Arg Lys
1               5

<210> SEQ ID NO 22
<211> LENGTH: 16
<212> TYPE: PRT
<213> ORGANISM: Homo Sapiens

<400> SEQUENCE: 22

Arg Ser Ser Gln Ser Leu Leu His Ser Asn Gly Tyr Asn Tyr Val Asp
1               5                   10                  15

<210> SEQ ID NO 23
<211> LENGTH: 7
<212> TYPE: PRT
<213> ORGANISM: Homo Sapiens

<400> SEQUENCE: 23

Leu Gly Ser Asn Arg Ala Ser
1               5

<210> SEQ ID NO 24
<211> LENGTH: 10
<212> TYPE: PRT
<213> ORGANISM: Homo Sapiens

<400> SEQUENCE: 24

Met Gln Gly Leu Gln Asp Pro Arg Thr Phe
1               5                   10

<210> SEQ ID NO 25
<211> LENGTH: 121
<212> TYPE: PRT
<213> ORGANISM: Homo Sapiens

<400> SEQUENCE: 25

Thr Gln Val Gln Leu Val Gln Ser Gly Thr Glu Val Lys Lys Pro Gly
1               5                   10                  15

Ala Ser Val Lys Val Ser Cys Lys Val Ser Gly Tyr Ser Leu Ser Glu
                20                  25                  30

Leu Ser Met His Trp Val Arg Gln Ala Pro Gly Lys Gly Leu Glu Trp
            35                  40                  45

Met Gly Ser Phe Asp Pro Glu Asp Gly Glu Thr Thr Tyr Ala Gln Arg
    50                  55                  60

Phe Gln Gly Arg Val Thr Met Thr Glu Asp Thr Ser Thr Asp Thr Ala
65                  70                  75                  80

Tyr Met Glu Leu Arg Ser Leu Thr Ser Asp Asp Thr Ala Val Tyr Tyr
                85                  90                  95

Cys Ala Arg Glu Ile Trp Ser Gly Tyr Ala Tyr Phe Asp Leu Trp Gly
            100                 105                 110

Arg Gly Thr Leu Val Thr Val Ser Ser
            115                 120

<210> SEQ ID NO 26
<211> LENGTH: 115
<212> TYPE: PRT
<213> ORGANISM: Homo Sapiens

<400> SEQUENCE: 26
```

```
Gln Pro Val Leu Thr Gln Ser Ser Leu Ser Ala Ser Pro Gly Ala
1               5                   10                  15

Ser Val Ser Leu Thr Cys Thr Leu Arg Ser Gly Ile Asn Val Gly Pro
            20                  25                  30

Tyr Arg Met Tyr Trp Tyr Gln Gln Lys Pro Gly Ser Pro Gln Tyr
        35                  40                  45

Leu Leu Ser Tyr Lys Ser Asp Ser Asp Thr Gln Ala Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Asn Asn Ala Val Val Phe Gly Gly Gly Thr Lys Leu
            100                 105                 110

Thr Val Leu
        115
```

<210> SEQ ID NO 27
<211> LENGTH: 10
<212> TYPE: PRT
<213> ORGANISM: Homo Sapiens

<400> SEQUENCE: 27

```
Gly Tyr Ser Leu Ser Glu Leu Ser Met His
1               5                   10
```

<210> SEQ ID NO 28
<211> LENGTH: 17
<212> TYPE: PRT
<213> ORGANISM: Homo Sapiens

<400> SEQUENCE: 28

```
Ser Phe Asp Pro Glu Asp Gly Glu Thr Thr Tyr Ala Gln Arg Phe Gln
1               5                   10                  15

Gly
```

<210> SEQ ID NO 29
<211> LENGTH: 11
<212> TYPE: PRT
<213> ORGANISM: Homo Sapiens

<400> SEQUENCE: 29

```
Glu Ile Trp Ser Gly Tyr Ala Tyr Phe Asp Leu
1               5                   10
```

<210> SEQ ID NO 30
<211> LENGTH: 14
<212> TYPE: PRT
<213> ORGANISM: Homo Sapiens

<400> SEQUENCE: 30

```
Thr Leu Arg Ser Gly Ile Asn Val Gly Pro Tyr Arg Met Tyr
1               5                   10
```

<210> SEQ ID NO 31
<211> LENGTH: 7
<212> TYPE: PRT
<213> ORGANISM: Homo Sapiens

<400> SEQUENCE: 31

```
Lys Ser Asp Ser Asp Thr Gln
```

-continued

```
1               5
```

<210> SEQ ID NO 32
<211> LENGTH: 9
<212> TYPE: PRT
<213> ORGANISM: Homo Sapiens

<400> SEQUENCE: 32

```
Met Ile Trp His Asn Asn Ala Val Val
1               5
```

<210> SEQ ID NO 33
<211> LENGTH: 245
<212> TYPE: PRT
<213> ORGANISM: Homo Sapiens

<400> SEQUENCE: 33

```
Ser Tyr Glu Leu Ile Gln Pro Pro Ser Val Ser Val Ala Pro Gly Gln
1               5                   10                  15

Thr Ala Arg Ile Thr Cys Gly Gly Ser Asn Ile Arg Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Arg Thr Lys Val Thr Val Leu Ser Gly Gly Ser
            100                 105                 110

Thr Thr Thr Ser Tyr Asn Val Tyr Tyr Thr Lys Leu Ser Ser Ser Gly
        115                 120                 125

Thr Gln Val Gln Leu Val Glu Ser Gly Gly Gly Leu Val Gln Pro Gly
    130                 135                 140

Gly Ser Leu Arg Leu Ser Cys Ala Ala Ser Gly Phe Thr Phe Ser Ser
145                 150                 155                 160

Tyr Ala Met Ser Trp Val Arg Gln Ala Pro Gly Lys Gly Leu Glu Trp
                165                 170                 175

Val Ser Ala Ile Ser Gly Ser Gly Gly Ser Thr Tyr Tyr Ala Asp Ser
            180                 185                 190

Val Lys Gly Arg Phe Thr Ile Ser Arg Asp Asn Ser Lys Asn Thr Leu
        195                 200                 205

Tyr Leu Gln Met Asn Ser Leu Arg Ala Glu Asp Thr Ala Val Tyr Tyr
    210                 215                 220

Cys Ala Thr His Ala Ala Ala Gly Asp Tyr Trp Gly Gln Gly Thr Leu
225                 230                 235                 240

Val Thr Val Ser Ser
                245
```

<210> SEQ ID NO 34
<211> LENGTH: 246
<212> TYPE: PRT
<213> ORGANISM: Homo Sapiens

<400> SEQUENCE: 34

```
Ser Tyr Glu Leu Thr Gln Pro Pro Ser Val Ser Val Ala Pro Gly Lys
1               5                   10                  15
```

Thr Ala Arg Ile Thr Cys Glu Gly Asn Asn Ile Gly Ser Lys Gly Val
            20                  25                  30

His Trp Tyr Gln Gln Lys Pro Gly Gln Ala Pro Ala Leu Val Val Tyr
            35                  40                  45

Asp Gly Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Pro Asn Tyr Val Phe Gly Thr Arg Thr Lys Leu Thr Val Leu Ser Gly
            100                 105                 110

Gly Ser Thr Lys Thr Ser Tyr Asn Val Tyr Tyr Thr Lys Leu Ser Ser
            115                 120                 125

Ser Gly Thr Gln Val Gln Leu Val Glu Thr Gly Gly Gly Leu Val Gln
            130                 135                 140

Pro Gly Gly Ser Leu Arg Leu Ser Cys Ala Ala Ser Gly Phe Thr Phe
145                 150                 155                 160

Ser Ser Tyr Ala Met Ser Trp Val Arg Gln Ala Pro Gly Lys Gly Leu
                165                 170                 175

Glu Trp Val Ser Ala Ile Ser Gly Ser Gly Gly Ser Thr Tyr Tyr Ala
                180                 185                 190

Asp Ser Val Lys Gly Arg Phe Thr Ile Ser Arg Asp Asn Ser Lys Asn
            195                 200                 205

Thr Leu Tyr Leu Gln Met Asn Ser Leu Arg Ala Glu Asp Thr Ala Val
            210                 215                 220

Tyr Tyr Cys Ala Arg Val Ala Ala Gly Asp Tyr Trp Gly Gln Gly Thr
225                 230                 235                 240

Leu Val Thr Val Ser Ser
                245

<210> SEQ ID NO 35
<211> LENGTH: 249
<212> TYPE: PRT
<213> ORGANISM: Homo Sapiens

<400> SEQUENCE: 35

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Val Asp Trp Tyr Leu Gln Lys Pro Gly Gln Pro
            35                  40                  45

Pro His Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Asp Pro Arg Thr Phe Gly Gln Gly Thr Lys Val Glu Ile Lys
            100                 105                 110

Ser Gly Gly Ser Thr Ile Thr Ser Tyr Asn Val Tyr Tyr Thr Lys Leu
            115                 120                 125

Ser Ser Ser Gly Thr Gln Val Gln Leu Val Glu Ser Gly Gly Gly Leu

```
                130                 135                 140
Val Gln Pro Gly Gly Ser Leu Arg Leu Ser Cys Ala Ala Ser Gly Phe
145                 150                 155                 160

Ala Phe Ser Asn Tyr Ala Met Ser Trp Val Arg Gln Ala Pro Gly Lys
                165                 170                 175

Gly Leu Glu Trp Val Ser Gly Ile Ser Gly Ser Gly Ser Thr Tyr
                180                 185                 190

Tyr Ala Asp Ser Val Lys Gly Arg Phe Thr Ile Ser Arg Asp Asn Ser
                195                 200                 205

Lys Asn Thr Leu Tyr Leu Gln Met Asn Ser Leu Arg Ala Glu Asp Thr
                210                 215                 220

Ala Val Tyr Tyr Cys Ala Arg Glu Gly Ala Phe Gly Gly Arg Lys Gly
225                 230                 235                 240

Gln Gly Thr Leu Val Thr Val Ser Ser
                245

<210> SEQ ID NO 36
<211> LENGTH: 256
<212> TYPE: PRT
<213> ORGANISM: Homo Sapiens

<400> SEQUENCE: 36

Gln Pro Val Leu Thr Gln Ser Ser Ser Leu Ser Ala Ser Pro Gly Ala
1               5                   10                  15

Ser Val Ser Leu Thr Cys Thr Leu Arg Ser Gly Ile Asn Val Gly Pro
                20                  25                  30

Tyr Arg Met Tyr Trp Tyr Gln Gln Lys Pro Gly Ser Pro Pro Gln Tyr
                35                  40                  45

Leu Leu Ser Tyr Lys Ser Asp Ser Asp Thr Gln Ala Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Asn Asn Ala Val Val Phe Gly Gly Gly Thr Lys Leu
                100                 105                 110

Thr Val Leu Ser Gly Gly Ser Thr Ile Thr Ser Tyr Asn Val Tyr Tyr
                115                 120                 125

Thr Lys Leu Ser Ser Ser Gly Thr Gln Val Gln Leu Val Gln Ser Gly
                130                 135                 140

Thr Glu Val Lys Lys Pro Gly Ala Ser Val Lys Val Ser Cys Lys Val
145                 150                 155                 160

Ser Gly Tyr Ser Leu Ser Glu Leu Ser Met His Trp Val Arg Gln Ala
                165                 170                 175

Pro Gly Lys Gly Leu Glu Trp Met Gly Ser Phe Asp Pro Glu Asp Gly
                180                 185                 190

Glu Thr Thr Tyr Ala Gln Arg Phe Gln Gly Arg Val Thr Met Thr Glu
                195                 200                 205

Asp Thr Ser Thr Asp Thr Ala Tyr Met Glu Leu Arg Ser Leu Thr Ser
                210                 215                 220

Asp Asp Thr Ala Val Tyr Tyr Cys Ala Arg Glu Ile Trp Ser Gly Tyr
225                 230                 235                 240

Ala Tyr Phe Asp Leu Trp Gly Arg Gly Thr Leu Val Thr Val Ser Ser
                245                 250                 255
```

<210> SEQ ID NO 37
<211> LENGTH: 119
<212> TYPE: PRT
<213> ORGANISM: Homo Sapiens

<400> SEQUENCE: 37

Gln Val Arg Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Glu Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Tyr Ser Ser Ile Asp Ala Phe Glu Ile Trp Gly Gln Gly
            100                 105                 110

Thr Met Val Thr Val Ser Ser
        115

<210> SEQ ID NO 38
<211> LENGTH: 108
<212> TYPE: PRT
<213> ORGANISM: Homo Sapiens

<400> SEQUENCE: 38

Ser Tyr Val Leu Thr Gln Pro Pro Ser Val Ser Val Ala Pro Gly Lys
1               5                   10                  15

Thr Ala Thr Ile Thr Cys Gly Gly Asp Asp Ile Gly Ser Lys Ser Val
            20                  25                  30

His Trp Tyr Gln Gln Lys Pro Gly Gln Ala Pro Val Leu Val Val Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Ala Ile Ser Arg Val Glu Ala Gly
65                  70                  75                  80

Asp Glu Ala Asp Tyr Tyr Cys Gln Val Trp Asp Ser Ser Asp Gln
                85                  90                  95

Tyr Val Phe Gly Ser Gly Thr Lys Leu Thr Val Leu
            100                 105

<210> SEQ ID NO 39
<211> LENGTH: 10
<212> TYPE: PRT
<213> ORGANISM: Homo Sapiens

<400> SEQUENCE: 39

Gly Gly Ser Ile Ser Ser Gly Gly Tyr Tyr
1               5                   10

<210> SEQ ID NO 40
<211> LENGTH: 16
<212> TYPE: PRT
<213> ORGANISM: Homo Sapiens

<400> SEQUENCE: 40

```
Tyr Ile Tyr Tyr Ser Gly Ser Thr Tyr Asn Pro Ser Leu Glu Ser
1               5                   10                  15

<210> SEQ ID NO 41
<211> LENGTH: 10
<212> TYPE: PRT
<213> ORGANISM: Homo Sapiens

<400> SEQUENCE: 41

Arg Tyr Ser Ser Ile Asp Ala Phe Glu Ile
1               5                   10

<210> SEQ ID NO 42
<211> LENGTH: 11
<212> TYPE: PRT
<213> ORGANISM: Homo Sapiens

<400> SEQUENCE: 42

Gly Gly Asp Asp Ile Gly Ser Lys Ser Val His
1               5                   10

<210> SEQ ID NO 43
<211> LENGTH: 7
<212> TYPE: PRT
<213> ORGANISM: Homo Sapiens

<400> SEQUENCE: 43

Asp Asp Gly Asp Arg Pro Ser
1               5

<210> SEQ ID NO 44
<211> LENGTH: 11
<212> TYPE: PRT
<213> ORGANISM: Homo Sapiens

<400> SEQUENCE: 44

Gln Val Trp Asp Ser Ser Ser Asp Gln Tyr Val
1               5                   10

<210> SEQ ID NO 45
<211> LENGTH: 130
<212> TYPE: PRT
<213> ORGANISM: Homo Sapiens

<400> SEQUENCE: 45

Gln Val Gln Leu Gln Gln Ser Gly Pro Gly Leu Val Glu Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Arg Trp Tyr Asn Asp Tyr Ala
        50                  55                  60

Val Ser Val Glu Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Tyr Tyr Asp Ser Ser Gly Tyr Tyr
            100                 105                 110

Tyr Phe Asp Ala Phe Gly Ile Trp Gly Gln Gly Thr Met Val Thr Val
            115                 120                 125
```

Ser Ser
    130

<210> SEQ ID NO 46
<211> LENGTH: 109
<212> TYPE: PRT
<213> ORGANISM: Homo Sapiens

<400> SEQUENCE: 46

Ser Tyr Glu Leu Ile Gln Pro Pro Ser Val Ser Val Ala Pro Gly Gln
1               5                   10                  15

Thr Ala Arg Ile Ala Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Gly Val Phe Gly Thr Gly Thr Lys Leu Thr Val Leu
            100                 105

<210> SEQ ID NO 47
<211> LENGTH: 10
<212> TYPE: PRT
<213> ORGANISM: Homo Sapiens

<400> SEQUENCE: 47

Gly Asp Ser Val Ser Ser Asn Ser Ala Ala
1               5                   10

<210> SEQ ID NO 48
<211> LENGTH: 18
<212> TYPE: PRT
<213> ORGANISM: Homo Sapiens

<400> SEQUENCE: 48

Arg Thr Tyr Tyr Arg Ser Arg Trp Tyr Asn Asp Tyr Ala Val Ser Val
1               5                   10                  15

Glu Ser

<210> SEQ ID NO 49
<211> LENGTH: 18
<212> TYPE: PRT
<213> ORGANISM: Homo Sapiens

<400> SEQUENCE: 49

Asp Pro Tyr Tyr Tyr Asp Ser Ser Gly Tyr Tyr Tyr Phe Asp Ala Phe
1               5                   10                  15

Gly Ile

<210> SEQ ID NO 50
<211> LENGTH: 11
<212> TYPE: PRT
<213> ORGANISM: Homo Sapiens

<400> SEQUENCE: 50

Gly Gly Asn Asn Ile Gly Ser Lys Ser Val His

-continued

```
1               5                   10

<210> SEQ ID NO 51
<211> LENGTH: 7
<212> TYPE: PRT
<213> ORGANISM: Homo Sapiens

<400> SEQUENCE: 51

Asp Asp Ser Asp Arg Pro Ser
1               5

<210> SEQ ID NO 52
<211> LENGTH: 12
<212> TYPE: PRT
<213> ORGANISM: Homo Sapiens

<400> SEQUENCE: 52

Gln Val Trp Asp Ser Ser Ser Asp His Pro Gly Val
1               5                   10

<210> SEQ ID NO 53
<211> LENGTH: 130
<212> TYPE: PRT
<213> ORGANISM: Homo Sapiens

<400> SEQUENCE: 53

Gln Val Gln Leu Gln Gln Ser Gly Pro Gly Leu Val Lys Pro Pro Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Tyr Tyr Tyr Asp Ser Ser Gly Tyr Tyr
            100                 105                 110

Tyr Phe Asp Ala Phe Asp Ile Trp Gly Gln Gly Thr Met Val Thr Val
        115                 120                 125

Ser Ser
    130

<210> SEQ ID NO 54
<211> LENGTH: 108
<212> TYPE: PRT
<213> ORGANISM: Homo Sapiens

<400> SEQUENCE: 54

Ser Tyr Glu Leu Thr Gln Pro His Ser Val Ser Val Ala Pro Gly Gln
1               5                   10                  15

Thr Ala Arg Ile Thr Cys Gly Gly Asp Asn Ile Gly Ser Lys Ser Val
            20                  25                  30

His Trp Tyr Gln Gln Arg Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60
```

-continued

Asn Ser Glu Asn Thr Ala Thr Leu Thr Ile Ser Gly Val Glu Ala Gly
65                  70                  75                  80

Asp Glu Ala Asp Tyr Tyr Cys Gln Val Trp Asp Ser Thr Ser His His
            85                  90                  95

Val Val Phe Gly Gly Gly Thr Lys Leu Thr Val Leu
            100                 105

<210> SEQ ID NO 55
<211> LENGTH: 10
<212> TYPE: PRT
<213> ORGANISM: Homo Sapiens

<400> SEQUENCE: 55

Gly Asp Ser Val Ser Ser Asn Ser Ala Ala
1               5                   10

<210> SEQ ID NO 56
<211> LENGTH: 18
<212> TYPE: PRT
<213> ORGANISM: Homo Sapiens

<400> SEQUENCE: 56

Arg Thr Tyr Tyr Arg Ser Lys Trp Tyr Asn Asp Tyr Ala Val Ser Val
1               5                   10                  15

Lys Ser

<210> SEQ ID NO 57
<211> LENGTH: 18
<212> TYPE: PRT
<213> ORGANISM: Homo Sapiens

<400> SEQUENCE: 57

Asp Pro Tyr Tyr Tyr Asp Ser Ser Gly Tyr Tyr Tyr Phe Asp Ala Phe
1               5                   10                  15

Asp Ile

<210> SEQ ID NO 58
<211> LENGTH: 11
<212> TYPE: PRT
<213> ORGANISM: Homo Sapiens

<400> SEQUENCE: 58

Gly Gly Asp Asn Ile Gly Ser Lys Ser Val His
1               5                   10

<210> SEQ ID NO 59
<211> LENGTH: 7
<212> TYPE: PRT
<213> ORGANISM: Homo Sapiens

<400> SEQUENCE: 59

Asp Asp Ser Asp Arg Pro Ser
1               5

<210> SEQ ID NO 60
<211> LENGTH: 11
<212> TYPE: PRT
<213> ORGANISM: Homo Sapiens

<400> SEQUENCE: 60

Gln Val Trp Asp Ser Thr Ser His His Val Val
1               5                   10

```
<210> SEQ ID NO 61
<211> LENGTH: 248
<212> TYPE: PRT
<213> ORGANISM: Homo sapiens

<400> SEQUENCE: 61

Ser Tyr Val Leu Thr Gln Pro Pro Ser Val Ser Val Ala Pro Gly Lys
1               5                   10                  15

Thr Ala Thr Ile Thr Cys Gly Gly Asp Asp Ile Gly Ser Lys Ser Val
            20                  25                  30

His Trp Tyr Gln Gln Lys Pro Gly Gln Ala Pro Val Leu Val Val Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Ala Ile Ser Arg Val Glu Ala Gly
65                  70                  75                  80

Asp Glu Ala Asp Tyr Tyr Cys Gln Val Trp Asp Ser Ser Ser Asp Gln
                85                  90                  95

Tyr Val Phe Gly Ser Gly Thr Lys Leu Thr Val Leu Ser Gly Gly Ser
            100                 105                 110

Thr Ile Thr Ser Tyr Asn Val Tyr Thr Lys Leu Ser Ser Ser Gly
        115                 120                 125

Thr Gln Val Arg Leu Gln Glu Ser Gly Pro Gly Leu Val Lys Pro Ser
    130                 135                 140

Gln Thr Leu Ser Leu Thr Cys Thr Val Ser Gly Gly Ser Ile Ser Ser
145                 150                 155                 160

Gly Gly Tyr Tyr Trp Ser Trp Ile Arg Gln His Pro Gly Lys Gly Leu
                165                 170                 175

Glu Trp Ile Gly Tyr Ile Tyr Tyr Ser Gly Ser Thr Tyr Tyr Asn Pro
            180                 185                 190

Ser Leu Glu Ser Arg Val Thr Ile Ser Val Asp Thr Ser Lys Asn Gln
        195                 200                 205

Phe Ser Leu Lys Leu Ser Ser Val Thr Ala Ala Asp Thr Ala Val Tyr
    210                 215                 220

Tyr Cys Ala Arg Tyr Ser Ser Ile Asp Ala Phe Glu Ile Trp Gly Gln
225                 230                 235                 240

Gly Thr Met Val Thr Val Ser Ser
                245

<210> SEQ ID NO 62
<211> LENGTH: 260
<212> TYPE: PRT
<213> ORGANISM: Homo Sapiens

<400> SEQUENCE: 62

Ser Tyr Glu Leu Ile Gln Pro Pro Ser Val Ser Val Ala Pro Gly Gln
1               5                   10                  15

Thr Ala Arg Ile Ala Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80
```

```
Asp Glu Ala Asp Tyr Tyr Cys Gln Val Trp Asp Ser Ser Asp His
                85                  90                  95
Pro Gly Val Phe Gly Thr Gly Thr Lys Leu Thr Val Leu Ser Gly Gly
            100                 105                 110
Ser Thr Ile Thr Ser Tyr Asn Val Tyr Tyr Thr Lys Leu Ser Ser Ser
            115                 120                 125
Gly Thr Gln Val Gln Leu Gln Gln Ser Gly Pro Gly Leu Val Glu Pro
130                 135                 140
Ser Gln Thr Leu Ser Leu Thr Cys Ala Ile Ser Gly Asp Ser Val Ser
145                 150                 155                 160
Ser Asn Ser Ala Ala Trp Asn Trp Ile Arg Gln Ser Pro Ser Arg Gly
                165                 170                 175
Leu Glu Trp Leu Gly Arg Thr Tyr Tyr Arg Ser Arg Trp Tyr Asn Asp
            180                 185                 190
Tyr Ala Val Ser Val Glu Ser Arg Ile Thr Ile Asn Pro Asp Thr Ser
            195                 200                 205
Lys Asn Gln Phe Ser Leu Gln Leu Asn Ser Val Thr Pro Glu Asp Thr
        210                 215                 220
Ala Val Tyr Tyr Cys Ala Arg Asp Pro Tyr Tyr Tyr Asp Ser Ser Gly
225                 230                 235                 240
Tyr Tyr Tyr Phe Asp Ala Phe Gly Ile Trp Gly Gln Gly Thr Met Val
                245                 250                 255
Thr Val Ser Ser
            260

<210> SEQ ID NO 63
<211> LENGTH: 259
<212> TYPE: PRT
<213> ORGANISM: Homo Sapiens

<400> SEQUENCE: 63

Ser Tyr Glu Leu Thr Gln Pro His Ser Val Ser Val Ala Pro Gly Gln
1               5                   10                  15
Thr Ala Arg Ile Thr Cys Gly Gly Asp Asn Ile Gly Ser Lys Ser Val
            20                  25                  30
His Trp Tyr Gln Gln Arg Pro Gly Gln Ala Pro Val Leu Val Val Tyr
        35                  40                  45
Asp Asp Ser Asp Arg Pro Ser Gly Ile Pro Glu Arg Phe Ser Gly Ser
    50                  55                  60
Asn Ser Glu Asn Thr Ala Thr Leu Thr Ile Ser Gly Val Glu Ala Gly
65                  70                  75                  80
Asp Glu Ala Asp Tyr Tyr Cys Gln Val Trp Asp Ser Thr Ser His His
                85                  90                  95
Val Val Phe Gly Gly Thr Lys Leu Thr Val Leu Ser Gly Gly Ser
            100                 105                 110
Thr Ile Thr Ser Tyr Asn Val Tyr Tyr Thr Lys Leu Ser Ser Ser Gly
        115                 120                 125
Thr Gln Val Gln Leu Gln Gln Ser Gly Pro Gly Leu Val Lys Pro Pro
130                 135                 140
Gln Thr Leu Ser Leu Thr Cys Ala Ile Ser Gly Asp Ser Val Ser Ser
145                 150                 155                 160
Asn Ser Ala Ala Trp Asn Trp Ile Arg Gln Ser Pro Ser Arg Gly Leu
                165                 170                 175
Glu Trp Leu Gly Arg Thr Tyr Tyr Arg Ser Lys Trp Tyr Asn Asp Tyr
            180                 185                 190
```

Ala Val Ser Val Lys Ser Arg Ile Thr Ile Asn Pro Asp Thr Ser Lys
            195                 200                 205

Asn Gln Phe Ser Leu Gln Leu Asn Ser Val Thr Pro Glu Asp Thr Ala
        210                 215                 220

Val Tyr Tyr Cys Ala Arg Asp Pro Tyr Tyr Asp Ser Ser Gly Tyr
225                 230                 235                 240

Tyr Tyr Phe Asp Ala Phe Asp Ile Trp Gly Gln Gly Thr Met Val Thr
                245                 250                 255

Val Ser Ser

<210> SEQ ID NO 64
<211> LENGTH: 11
<212> TYPE: PRT
<213> ORGANISM: Homo Sapiens

<400> SEQUENCE: 64

Cys Ala Thr His Ala Ala Ala Gly Asp Tyr Trp
1               5                   10

<210> SEQ ID NO 65
<211> LENGTH: 11
<212> TYPE: PRT
<213> ORGANISM: Homo Sapiens

<400> SEQUENCE: 65

Cys Ala Arg Val Ala Ala Ala Gly Asp Tyr Trp
1               5                   10

<210> SEQ ID NO 66
<211> LENGTH: 11
<212> TYPE: PRT
<213> ORGANISM: Homo Sapiens

<400> SEQUENCE: 66

Cys Ala Arg Glu Gly Ala Phe Gly Gly Arg Lys
1               5                   10

<210> SEQ ID NO 67
<211> LENGTH: 15
<212> TYPE: PRT
<213> ORGANISM: Homo Sapiens

<400> SEQUENCE: 67

Cys Ala Arg Glu Ile Trp Ser Gly Tyr Ala Tyr Phe Asp Leu Trp
1               5                   10                  15

<210> SEQ ID NO 68
<211> LENGTH: 13
<212> TYPE: PRT
<213> ORGANISM: Homo Sapiens

<400> SEQUENCE: 68

Cys Ala Arg Tyr Ser Ser Ile Asp Ala Phe Glu Ile Trp
1               5                   10

<210> SEQ ID NO 69
<211> LENGTH: 22
<212> TYPE: PRT
<213> ORGANISM: Homo Sapiens

<400> SEQUENCE: 69

Cys Ala Arg Asp Pro Tyr Tyr Tyr Asp Ser Ser Gly Tyr Tyr Tyr Phe

-continued

```
                1               5                  10                  15
Asp Ala Phe Gly Ile Trp
            20

<210> SEQ ID NO 70
<211> LENGTH: 22
<212> TYPE: PRT
<213> ORGANISM: Homo Sapiens

<400> SEQUENCE: 70

Cys Ala Arg Asp Pro Tyr Tyr Tyr Asp Ser Ser Gly Tyr Tyr Tyr Phe
1               5                  10                  15

Asp Ala Phe Asp Ile Trp
            20
```

GRP78-BINDING ANTIBODIES AND USES THEREOF IN DETECTING OR NEUTRALIZING GRP78

CROSS-REFERENCE TO RELATED APPLICATIONS

This application is a continuation of, and claims priority to, U.S. patent application Ser. No. 17/592,828, filed Feb. 4, 2022, which is a divisional of, and claims priority to, U.S. application Ser. No. 16/333,898, filed Mar. 15, 2019, now issued as U.S. Pat. No. 11,254,751, which is a 35 U.S.C. § 371 national phase application from, and claims priority to, PCT International Application No. PCT/US2017/052661, filed Sep. 21, 2017, which claims the benefit of priority under 35 U.S.C. § 119(e) of U.S. Provisional Application Nos. 62/397,512, filed Sep. 21, 2016, and 62/397,521, filed Sep. 21, 2016, each of said applications being incorporated by reference in their entireties herein.

STATEMENT REGARDING FEDERALLY SPONSORED RESEARCH OR DEVELOPMENT

This invention was made with Government support under grant number DK093500 awarded by the National Institutes of Health and grant number DE-AC52-06NA25396 awarded by the Department of Energy. The Government has certain rights in the invention.

INCORPORATION-BY-REFERENCE OF MATERIAL SUBMITTED AS A TEXT FILE VIA THE OFFICE ELECTRONIC FILING SYSTEM

This invention contains one or more sequences in a computer readable format in an accompanying text file titled "370602-7050US3_Sequence_Listing," which is 40.0 KB in size and was created May 29, 2022, the contents of which are incorporated herein by reference in their entirety.

BACKGROUND OF THE INVENTION

Field of the Invention

The present invention relates generally to the field of cancer biology. More particularly, it concerns targeting antibodies for the treatment and detection of cancer. In additional embodiments,

Description of Related Art

The development of targeted tools for cancer therapy is a major focus in oncology. Monoclonal antibody based therapies can have promising beneficial results, but standard approaches to generate antibodies against targets of interest with therapeutic properties are time consuming and not always successful.

The concept of targeted cancer therapy is predicated on the assumption that tumors have unique and sustained genetic abnormalities, and that direct targeting of such distinctive biological features can only be accomplished through the identification and validation of certain specific molecular markers. These principles are particularly relevant to lung cancer, the leading cause of cancer-related death worldwide (Ferlay et al., 2010, *Int J Cancer* 127: 2893-2917; Jemal et al., 2010, *Cancer epidemiology, biomarkers & prevention* 19:1893-1907; Jemal et al, 2010, *Cancer J Clin* 60:277-300). The discovery of novel targets and the development of therapies and diagnostics (such as those based on monoclonal antibodies) promise to revolutionize anti-cancer therapy and cancer cell imaging techniques. However, there remains and urgent unmet need to identify cancer cell binding agents, such as antibodies that bind to EphA5, that are effective for therapy and/or imaging.

Ephrin type-A receptor 5 is a protein that is encoded by the EphA5 gene in humans. Ephrin receptors belong to a family of closely related proteins with diverse functions in both normal physiology and disease pathogenesis (Pasquale 2008; Pasquale 2010). EphA5 is mostly recognized for its critical role in axonal guidance during embryonic development (Taylor et al. 1994; Zhou 1997; Murai and Pasquale 2002); its involvement in cancer is only recently becoming evident (Fu et al. 2010; Giaginis et al. 2010; Pejovic et al. 2009).

GRP78, also known as heat shock protein-5 (Hspa5/BiP), is part of an evolutionarily conserved, ER-linked stress response mechanism that provides cellular survival signals during environmental and physiologic duress. As a molecular component of the ER chaperoning network, GRP78 is classically involved with the processing of unfolded proteins, however newer insights also place the protein at the cell surface with the potential to influence signal transduction (Lee, 2014, Nature Rev Cancer 14(4): 263-276). Retrospective IHC studies have demonstrated that GRP78 expression positively correlates with poor survival in advanced breast cancer (Lee et al., 2006, Cancer Research 66(16): 7849-7853) and recurrence in prostate cancer patients (Daneshmand et al., 2007, Human Pathology 38(10): 1547-1552). Upregulation of GRP78 promotes survival and chemoresistance in both proliferating and dormant breast cancer cells. Synthetic peptides composed of GRP78-binding motifs coupled to a cell death-inducing peptide to promote apoptosis in cancer cells, demonstrating its in vivo accessibility (Arap et al., 2004, Cancer Cell 6(3): 275-284).

Monoclonal antibody-based therapy of human cancers has emerged as a major advance in contemporary medical oncology. However, the identification of suitable cancer target candidates is merely the initial step towards the development of clinical applications. Cancer-specific targets are often abundantly present on the surface of cancer cells or non-malignant tumor-associated vascular endothelial and stromal cells, and are thereby accessible from the systemic circulation (Ozawa et al., 2008). Such targets usually consist of a broad array of proteins that are overexpressed, mutated, or abnormally located in the cell surface compared to normal tissues (Carter et al., 2004). Conventionally, once a target candidate is identified and validated, panels of antibodies are produced, and evaluated for biological activity and favorable immune profiles prior to drug lead optimization. The more recent use of in vitro technologies, such as phage- and yeast-display, to generate monoclonal antibody clones has some advantages over traditional immunization. These include the speed with which antibody clones can be selected and isolated, the ability to enrich for specific properties in high-throughput and, perhaps most importantly, the fact that human monoclonal antibodies can be selected directly.

SUMMARY OF THE INVENTION

EphA5 Binding Monoclonal Antibodies

Described herein are EphA5 monoclonal antibodies or GRP78 monoclonal antibodies that potently block or reduce EphA5 signaling and GRP78 signaling and inhibit cancer cell proliferation. Thus, in a first embodiment, there is provided an isolated or recombinant monoclonal antibody that specifically binds to a EphA5. In certain aspects, an antibody that competes for the binding of a EphA5 with the E31, F31, TW3, or T22 antibody is provided. In certain aspects, the antibody may comprise all or part of the heavy chain variable region and/or light chain variable region of the E31, F31, TW3, or T22 antibodies. In a further aspect, the antibody may comprise an amino acid sequence that corresponds to a first, second, and/or third complementarity determining region (CDR) from the light variable and/or heavy variable chain of the E31, F31, TW3, or T22 antibodies of the present embodiments.

In certain aspects, the isolated EphA5 antibody comprises CDR sequences at least 80%, 85%, 90%, 91%, 92%, 93%, 94%, 95%, 96%, 97%, 98%, 99% or 100% identical to the CDR regions of the E31, F31, TW3, or T22 heavy and light chain amino acid sequences. In further aspects, an antibody comprises CDR regions identical to E31, F31, TW3, or T22 CDR regions, except for one or two amino acid substitutions, deletions, or insertions at one or more of the CDRs. For example, the antibody can comprise CDRs wherein the CDR sequences comprise 1 or 2 amino acid substitutions in the $V_H$ CDR1, $V_H$ CDR2, $V_H$ CDR3, $V_L$ CDR1, $V_L$ CDR2 and/or $V_L$ CDR3 relative to the CDRs of a E31, F31, TW3, or T22 antibody. Thus, in some specific aspects, an antibody of the embodiments comprises (a) a first $V_H$ CDR at least 80%, 85%, 90%, 91%, 92%, 93%, 94%, 95%, 96%, 97%, 98%, 99% or 100% identical to $V_H$ CDR1 of E31 (SEQ ID NO: 3), F31 (SEQ ID NO: 11), TW3 (SEQ ID NO: 19), or T22 (SEQ ID NO: 27); (b) a second $V_H$ CDR at least 80%, 85%, 90%, 91%, 92%, 93%, 94%, 95%, 96%, 97%, 98%, 99% or 100% identical to $V_H$ CDR2 of E31 (SEQ ID NO: 4), F31 (SEQ ID NO: 12), TW3 (SEQ ID NO: 20), or T22 (SEQ ID NO: 28); (c) a third $V_H$ CDR at least 80%, 85%, 90%, 91%, 92%, 93%, 94%, 95%, 96%, 97%, 98%, 99% or 100% identical to $V_H$ CDR3 of E31 (SEQ ID NO: 5), F31 (SEQ ID NO: 13), TW3 (SEQ ID NO: 21), or T22 (SEQ ID NO: 29); (d) a first $V_L$ CDR at least 80%, 85%, 90%, 91%, 92%, 93%, 94%, 95%, 96%, 97%, 98%, 99% or 100% identical to $V_L$ CDR1 of E31 (SEQ ID NO: 6), F31 (SEQ ID NO: 14), TW3 (SEQ ID NO: 22), or T22 (SEQ ID NO: 30); (e) a second $V_L$ CDR at least 80%, 85%, 90%, 91%, 92%, 93%, 94%, 95%, 96%, 97%, 98%, 99% or 100% identical to $V_L$ CDR2 of E31 (SEQ ID NO: 7), F31 (SEQ ID NO: 15), TW3 (SEQ ID NO: 23), or T22 (SEQ ID NO: 31); and (f) a third $V_L$ CDR at least 80%, 85%, 90%, 91%, 92%, 93%, 94%, 95%, 96%, 97%, 98%, 99% or 100% identical to $V_L$ CDR3 of E31 (SEQ ID NO: 8), F31 (SEQ ID NO: 16), TW3 (SEQ ID NO: 24), or T22 (SEQ ID NO: 32). In certain aspects, such an antibody is a humanized or de-immunized antibody comprising the foregoing CDRs on a human IgGs (e.g., IgG1, IgG2, IgG4, or a genetically modified IgG) backbone.

In further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of the E31 antibody, which are represented by SEQ ID NOs: 3, 4, 5, 6, 7, and 8, respectively. In one aspect, the isolated antibody comprises CDR sequences that are identical to the CDR sequences of E31 antibody.

In still further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of the F31 antibody, which are represented by SEQ ID NOs: 11, 12, 13, 14, 15, and 16, respectively. In one aspect, the isolated antibody comprises CDR sequences that are identical to the CDR sequences of F31 antibody.

In other aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of the TW3 antibody, which are represented by SEQ ID NOs: 19, 20, 21, 22, 23, and 24, respectively. In one aspect, the isolated antibody comprises CDR sequences that are identical to the CDR sequences of TW3 antibody.

In yet still further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of the T22 antibody, which are represented by SEQ ID NOs: 27, 28, 29, 30, 31, and 32, respectively. In one aspect, the isolated antibody comprises CDR sequences that are identical to the CDR sequences of T22 antibody.

In another aspect, the isolated antibody comprises a $V_H$ domain at least about 80%, 85%, 90%, 91%, 92%, 93%, 94%, 95%, 96%, 97%, 98%, 99% or 100% identical to the $V_H$ domain of E31 (SEQ ID NO: 1), F31 (SEQ ID NO: 9), TW3 (SEQ ID NO: 17), or T22 (SEQ ID NO: 25); and a $V_L$ domain at least about 80%, 85%, 90%, 91%, 92%, 93%, 94%, 95%, 96%, 97%, 98%, 99% or 100% identical to the $V_L$ domain of E31 (SEQ ID NO: 2), F31 (SEQ ID NO: 10), TW3 (SEQ ID NO: 18), or T22 (SEQ ID NO: 26). For example, the antibody can comprise a $V_H$ domain at least 95% identical to the $V_H$ domain of the humanized E31 antibody and a $V_L$ domain at least 95% identical to the $V_L$ domain of the humanized E31 antibody. Thus, in some aspects, an antibody comprises a $V_H$ domain identical to the $V_H$ domain of humanized E31 antibody and a $V_L$ domain identical to the $V_L$ domain of the humanized E31 antibody. In a specific example, the isolated antibody can comprise $V_H$ and $V_L$ domains identical to those of the E31 antibody. In other aspects, the antibody comprises a $V_H$ domain at least 95% identical to the $V_H$ domain of the humanized F31 antibody clone and a $V_L$ domain at least 95% identical to the $V_L$ domain of the humanized F31 antibody. For instance the antibody can comprise a $V_H$ domain identical to the $V_H$ domain of the humanized F31 antibody and a $V_L$ domain identical to the $V_L$ domain of the humanized F31 antibody. In another specific example, the isolated antibody can comprise $V_H$ and $V_L$ domains identical to those of the F31 antibody. In still further aspects, the antibody comprises a $V_H$ domain at least 95% identical to the $V_H$ domain of the humanized TW3 antibody and a $V_L$ domain at least 95% identical to the $V_L$ domain of the humanized TW3 antibody. For instance the antibody can comprise a $V_H$ domain identical to the $V_H$ domain of the humanized TW3 antibody and a $V_L$ domain identical to the $V_L$ domain of the humanized TW3 antibody. In a particular example, the isolated antibody can comprise $V_H$ and $V_L$ domains identical to those of the TW3 antibody. In another aspect, the antibody comprises a $V_H$ domain at least 95% identical to the $V_H$ domain of the humanized T22 antibody and a $V_L$ domain at least 95% identical to the $V_L$ domain of the humanized T22 antibody. For instance the antibody can comprise a $V_H$ domain identical to the $V_H$ domain of the humanized T22 antibody and a $V_L$ domain identical to the $V_L$ domain of the humanized T22 antibody. In a certain aspect, the isolated antibody can comprise $V_H$ and $V_L$ domains identical to those of the T22 antibody.

In some aspects, an antibody of the embodiments may be an IgG (e.g., IgG1, IgG2, IgG3 or IgG4), IgM, IgA, genetically modified IgG isotype, or an antigen binding fragment thereof. The antibody may be a Fab', F(ab')$_2$, a F(ab')$_3$, a monovalent scFv, a bivalent scFv, a bispecific or a single domain antibody. The antibody may be a human, humanized, or de-immunized antibody. In a further aspect, the isolated antibody is the E31, F31, TW3, or T22 antibody.

In some aspects, the antibody may be conjugated to an imaging agent, a chemotherapeutic agent, a toxin, or a radionuclide. In specific aspects, the antibody may be conjugated to auristatin or to monomethyl auristatin E (MMAE) in particular.

In one embodiment, there is provided a recombinant polypeptide comprising an antibody $V_H$ domain comprising CDRs 1-3 of the $V_H$ domain of E31 (SEQ ID NOs: 3, 4, and 5), F31 (SEQ ID NOs: 11, 12, and 13), TW3 (SEQ ID NOs: 19, 20, and 21), or T22 (SEQ ID NOs: 27, 28, and 29). In another embodiment, there is provided a recombinant polypeptide comprising an antibody $V_L$ domain comprising CDRs 1-3 of the $V_L$ domain of E31 (SEQ ID NOs: 6, 7, and 8), F31 (SEQ ID NOs: 14, 15, and 16), TW3 (SEQ ID NOs: 22, 23, and 24), or T22 (SEQ ID NOs: 30, 31, and 32).

In some embodiments, there is provided an isolated polynucleotide molecule comprising nucleic acid sequence encoding an antibody or a polypeptide comprising an antibody $V_H$ or $V_L$ domain disclosed herein.

In further embodiments, a host cell is provided that produces a monoclonal antibody or recombinant polypeptide of the embodiments. In some aspects, the host cell is a mammalian cell, a yeast cell, a bacterial cell, a ciliate cell, or an insect cell. In certain aspects, the host cell is a hybridoma cell.

In still further embodiments, there is provided a method of manufacturing an antibody of the present invention comprising expressing one or more polynucleotide molecule(s) encoding a $V_L$ or $V_H$ chain of an antibody disclosed herein in a cell and purifying the antibody from the cell.

In additional embodiments, there are pharmaceutical compositions comprising an antibody or antibody fragment as discussed herein. Such a composition further comprises a pharmaceutically acceptable carrier and may or may not contain additional active ingredients.

In embodiments of the present invention, there is provided a method for treating a subject having a cancer comprising administering an effective amount of an antibody disclosed herein. In certain aspects, the antibody is a monoclonal antibody of the embodiments herein, such as the E31, F31, TW3, or T22 antibody or a recombinant polypeptide comprising antibody segment derived therefrom.

In certain aspects, the cancer may be a breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer or skin cancer. In specific aspects, the cancer is an epithelial cancer. In other aspects, cancer may be a colorectal adenocarcinoma, lung adenocarcinoma, lung squamous cell carcinoma, breast cancer, hepatocellular carcinoma, ovarian cancer, kidney renal clear cell carcinoma, lung cancer or kidney cancer.

In one aspect, the antibody may be administered systemically. In additional aspects, the antibody may be administered intravenously, intradermally, intratumorally, intramuscularly, intraperitoneally, subcutaneously, or locally. The method may further comprise administering at least a second anticancer therapy to the subject. Examples of the second anticancer therapy include, but are not limited to, surgical therapy, chemotherapy, radiation therapy, cryotherapy, hormonal therapy, immunotherapy, or cytokine therapy.

In further aspects, the method may further comprise administering a composition of the present invention more than one time to the subject, such as, for example, 1, 2, 3, 4, 5, 6, 7, 8, 9, 10, 15, 20 or more times.

In another embodiment, there is provided a method for detecting a cancer in a subject comprising testing for the presence of elevated EphA5 relative to a control in a sample from the subject, wherein the testing comprises contacting the sample with an antibody disclosed herein. For example, the method may be an in vitro or in vivo method.

Certain embodiments are directed to an antibody or recombinant polypeptide composition comprising an isolated and/or recombinant antibody or polypeptide that specifically binds EphA5. In certain aspects the antibody or polypeptide has a sequence that is, is at least, or is at most 80, 85, 90, 95, 96, 97, 98, 99, or 100% identical (or any range derivable therein) to all or part of any antibody provided herein. In still further aspects the isolated and/ or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids from any of the sequences provided herein or a combination of such sequences.

In still further aspects, an antibody or polypeptide of the embodiments comprises one or more amino acid segments of the any of the amino acid sequences disclosed herein. For example, the antibody or polypeptide can comprise 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 amino acids in length, including all values and ranges there between, that are at least 80, 85, 90, 95, 96, 97, 98, 99, or 100% identical to any of the amino acid sequences disclosed herein. In certain aspects the amino segment(s) are selected from one of the amino acid sequences of a EphA5-binding antibody as provided herein.

In still further aspects, an antibody or polypeptide of the embodiments comprises an amino acid segment of the any of the amino acid sequences disclosed herein, wherein the segment begins at amino acid position 1, 2, 3, 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 in any sequence provided herein and ends at amino acid position 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 in the same provided sequence. In certain aspects the amino segment(s), or portions thereof, are selected from one of the amino acid sequences of a EphA5-binding antibody as provided herein.

In yet further aspects, an antibody or polypeptide of the embodiments comprises an amino acid segment that is at least 80%, 85%, 90%, 91%, 92%, 93%, 94%, 95%, 96%, 97%, 98%, 99% or 100% identical (or any range derivable therein) to a V, VJ, VDJ, D, DJ, J or CDR domain of a EphA5-binding antibody (as provided in Table 1). For example, a polypeptide may comprise 1, 2 or 3 amino acid segment that are at least 80%, 85%, 90%, 91%, 92%, 93%, 94%, 95%, 96%, 97%, 98%, 99% or 100% identical (or any range derivable therein) to CDRs 1, 2, and/or 3 a EphA5-binding antibody as provided in Table 1.

GRP78 Binding Monoclonal Antibodies

Embodiments of the present disclosure provide antibodies and methods of treating cancer employing such antibodies. In some embodiments, there are provided GRP78 specific human monoclonal antibodies. A unique method of combining phage and yeast display selection in vitro with tumor xenograft selection in vivo is provided. This method identifies highly specific and tumor cell-localizing single chain antibodies, as exemplified herein. The present disclosure also provides therapeutic compositions comprising GRP78 specific antibodies or antigen binding fragments thereof In preferred applications, fully human GRP78 antibodies and antigen binding fragments thereof are provided and employed in the generation of antibody-drug conjugates suitable for therapeutic administration to cancer patients. Without limitation, GRP78 positive breast and prostate cancer patients are expected to be excellent candidates for therapy with the compositions and methods of the invention.

Described herein are monoclonal antibodies against GRP78. In further aspects, provided GRP78-binding antibodies reduce GRP78 signaling and can be used to inhibit cancer cell proliferation. Thus, in a first embodiment, there is provided an isolated or recombinant monoclonal antibody that specifically binds to a GRP78. In certain aspects, an antibody that competes for the binding of a GRP78 with the B4, D1, or F6 antibody is provided. In certain aspects, the antibody may comprise all or part of the heavy chain variable region and/or light chain variable region of the B4, D1, or F6 antibodies. In a further aspect, the antibody may comprise an amino acid sequence that corresponds to a first, second, and/or third complementarity determining region (CDR) from the light variable and/or heavy variable chain of the B4, D1, or F6 antibodies of the present embodiments.

In certain aspects, the isolated antibody comprises CDR sequences at least 80%, 85%, 90%, 91%, 92%, 93%, 94%, 95%, 96%, 97%, 98%, 99% or 100% identical to the CDR regions of the B4, D1, or F6 heavy and light chain amino acid sequences. In further aspects, an antibody comprises CDR regions identical to the B4, D1, or F6 CDR regions, except for one or two amino acid substitutions, deletions, or insertions at one or more of the CDRs. For example, the antibody can comprise CDRs wherein the CDR sequences comprise 1 or 2 amino acid substitutions in the $V_H$ CDR1, $V_H$ CDR2, $V_H$ CDR3, $V_L$ CDR1, $V_L$ CDR2 and/or $V_L$ CDR3 relative to the CDRs of a B4, D1, or F6 antibody. Thus, in some specific aspects, an antibody of the embodiments comprises (a) a first $V_H$ CDR at least 80%, 85%, 90%, 91%, 92%, 93%, 94%, 95%, 96%, 97%, 98%, 99% or 100% identical to $V_H$ CDR1 of B4 (SEQ ID NO: 39), D1 (SEQ ID NO: 47), or F6 (SEQ ID NO: 55); (b) a second $V_H$ CDR at least 80%, 85%, 90%, 91%, 92%, 93%, 94%, 95%, 96%, 97%, 98%, 99% or 100% identical to $V_H$ CDR2 of B4 (SEQ ID NO: 40), D1 (SEQ ID NO: 48), or F6 (SEQ ID NO: 56); (c) a third $V_H$ CDR at least 80%, 85%, 90%, 91%, 92%, 93%, 94%, 95%, 96%, 97%, 98%, 99% or 100% identical to $V_H$ CDR3 of B4 (SEQ ID NO: 41), D1 (SEQ ID NO: 49), or F6 (SEQ ID NO: 57); (d) a first $V_L$ CDR at least 80%, 85%, 90%, 91%, 92%, 93%, 94%, 95%, 96%, 97%, 98%, 99% or 100% identical to $V_L$ CDR1 of B4 (SEQ ID NO: 42), D1 (SEQ ID NO: 50), or F6 (SEQ ID NO: 58); (e) a second $V_L$ CDR at least 80%, 85%, 90%, 91%, 92%, 93%, 94%, 95%, 96%, 97%, 98%, 99% or 100% identical to $V_L$ CDR2 of B4 (SEQ ID NO: 43), D1 (SEQ ID NO: 51), or F6 (SEQ ID NO: 59); and (f) a third $V_L$ CDR at least 80%, 85%, 90%, 91%, 92%, 93%, 94%, 95%, 96%, 97%, 98%, 99% or 100% identical to $V_L$ CDR3 of B4 (SEQ ID NO: 44), D1 (SEQ ID NO: 52), or F6 (SEQ ID NO: 60). In certain aspects, such an antibody is a humanized or de-immunized antibody comprising the foregoing CDRs on a human IgGs (e.g., IgG1, IgG2, IgG4, or a genetically modified IgG) backbone.

In further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of the B4 antibody, which are represented by SEQ ID NOs: 3, 4, 5, 6, 7, and 8, respectively. In one aspect, the isolated antibody comprises CDR sequences that are identical to the CDR sequences of B4 antibody.

In still further aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of the D1 antibody, which are represented by SEQ ID NOs: 11, 12, 13, 14, 15, and 16, respectively. In one aspect, the isolated antibody comprises CDR sequences that are identical to the CDR sequences of D1 antibody.

In other aspects, the isolated antibody comprises a first $V_H$, a second $V_H$, a third $V_H$, a first $V_L$, a second $V_L$, and a third $V_L$ CDR sequence at least 80%, 85%, 90%, 91%, 92%, 93%, 94%, 95%, 96%, 97%, 98%, 99% or 100% identical to the corresponding CDR sequence of the F6 antibody, which are represented by SEQ ID NOs: 19, 20, 21, 22, 23, and 24, respectively. In one aspect, the isolated antibody comprises CDR sequences that are identical to the CDR sequences of F6 antibody.

In another aspect, the isolated antibody comprises a $V_H$ domain at least about 80%, 85%, 90%, 91%, 92%, 93%, 94%, 95%, 96%, 97%, 98%, 99% or 100% identical to the $V_H$ domain of B4 (SEQ ID NO: 1), D1 (SEQ ID NO: 9), or F6 (SEQ ID NO: 17); and a $V_L$ domain at least about 80%, 85%, 90%, 91%, 92%, 93%, 94%, 95%, 96%, 97%, 98%, 99% or 100% identical to the $V_L$ domain of B4 (SEQ ID NO: 2), D1 (SEQ ID NO: 10), or F6 (SEQ ID NO: 18). For example, the antibody can comprise a $V_H$ domain at least 95% identical to the $V_H$ domain of the humanized B4 antibody and a $V_L$ domain at least 95% identical to the $V_L$ domain of the humanized B4 antibody. Thus, in some aspects, an antibody comprises a $V_H$ domain identical to the $V_H$ domain of humanized B4 antibody and a $V_L$ domain identical to the $V_L$ domain of the humanized B4 antibody. In a specific example, the isolated antibody can comprise $V_H$ and $V_L$ domains identical to those of the B4 antibody. In other aspects, the antibody comprises a $V_H$ domain at least 95% identical to the $V_H$ domain of the humanized D1 antibody and a $V_L$ domain at least 95% identical to the $V_L$ domain of the humanized D1 antibody. For instance the antibody can comprise a $V_H$ domain identical to the $V_H$ domain of the humanized D1 antibody and a $V_L$ domain identical to the $V_L$ domain of the humanized D1 antibody. In another specific example, the isolated antibody can comprise $V_H$ and $V_L$ domains identical to those of the D1 antibody. In still further aspects, the antibody comprises a $V_H$ domain at least 95% identical to the $V_H$ domain of the humanized F6 antibody and a $V_L$ domain at least 95% identical to the $V_L$ domain of the humanized F6 antibody. For instance the antibody can comprise a $V_H$ domain identical to the $V_H$ domain of the humanized F6 antibody and a $V_L$ domain identical to the $V_L$ domain of the humanized F6 antibody. In a particular example, the isolated antibody can comprise $V_H$ and $V_L$ domains identical to those of the F6 antibody.

In some aspects, an antibody of the embodiments may be an IgG (e.g., IgG1, IgG2, IgG3 or IgG4), IgM, IgA, genetically modified IgG isotype, or an antigen binding fragment thereof. The antibody may be a Fab', F(ab')$_2$, a F(ab')$_3$, a monovalent scFv, a bivalent scFv, a bispecific or a single domain antibody. The antibody may be a human, humanized, or de-immunized antibody. In a further aspect, the isolated antibody is the B4, D1, or F6 antibody.

In some aspects, the antibody may be conjugated to an imaging agent, a chemotherapeutic agent, a toxin, or a radionuclide. In specific aspects, the antibody may be conjugated to auristatin or to monomethyl auristatin E (MMAE) in particular.

In one embodiment, there is provided a recombinant polypeptide comprising an antibody $V_H$ domain comprising CDRs 1-3 of the $V_H$ domain of B4 (SEQ ID NOs: 3, 4, and 5), D1 (SEQ ID NOs: 11, 12, and 13), or F6 (SEQ ID NOs: 19, 20, and 21). In another embodiment, there is provided a recombinant polypeptide comprising an antibody $V_L$ domain comprising CDRs 1-3 of the $V_L$ domain of B4 (SEQ ID NOs: 6, 7, and 8), D1 (SEQ ID NOs: 14, 15, and 16), or F6 (SEQ ID NOs: 22, 23, and 24).

In some embodiments, there is provided an isolated polynucleotide molecule comprising nucleic acid sequence encoding an antibody or a polypeptide comprising an antibody $V_H$ or $V_L$ domain disclosed herein.

In further embodiments, a host cell is provided that produces a monoclonal antibody or recombinant polypeptide of the embodiments. In some aspects, the host cell is a mammalian cell, a yeast cell, a bacterial cell, a ciliate cell, or an insect cell. In certain aspects, the host cell is a hybridoma cell.

In still further embodiments, there is provided a method of manufacturing an antibody of the present invention comprising expressing one or more polynucleotide molecule(s) encoding a $V_L$ or $V_H$ chain of an antibody disclosed herein in a cell and purifying the antibody from the cell.

In additional embodiments, there are pharmaceutical compositions comprising an antibody or antibody fragment as discussed herein. Such a composition further comprises a pharmaceutically acceptable carrier and may or may not contain additional active ingredients.

In embodiments of the present invention, there is provided a method for treating a subject having a cancer comprising administering an effective amount of an antibody disclosed herein. In certain aspects, the antibody is a monoclonal antibody of the embodiments herein, such as the B4, D1, or F6 antibody or a recombinant polypeptide comprising antibody segment derived therefrom.

In certain aspects, the cancer may be a breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer or skin cancer. In specific aspects, the cancer is an epithelial cancer. In other aspects, cancer may be a colorectal adenocarcinoma, lung adenocarcinoma, lung squamous cell carcinoma, breast cancer, hepatocellular carcinoma, ovarian cancer, kidney renal clear cell carcinoma, lung cancer or kidney cancer.

In one aspect, the antibody may be administered systemically. In additional aspects, the antibody may be administered intravenously, intradermally, intratumorally, intramuscularly, intraperitoneally, subcutaneously, or locally. The method may further comprise administering at least a second anticancer therapy to the subject. Examples of the second anticancer therapy include, but are not limited to, surgical therapy, chemotherapy, radiation therapy, cryotherapy, hormonal therapy, immunotherapy, or cytokine therapy.

In further aspects, the method may further comprise administering a composition of the present invention more than one time to the subject, such as, for example, 1, 2, 3, 4, 5, 6, 7, 8, 9, 10, 15, 20 or more times.

In another embodiment, there is provided a method for detecting a cancer in a subject comprising testing for the presence of elevated GRP78 relative to a control in a sample from the subject, wherein the testing comprises contacting the sample with an antibody disclosed herein. For example, the method may be an in vitro or in vivo method.

Certain embodiments are directed to an antibody or recombinant polypeptide composition comprising an isolated and/or recombinant antibody or polypeptide that specifically binds GRP78. In certain aspects the antibody or polypeptide has a sequence that is, is at least, or is at most 80, 85, 90, 95, 96, 97, 98, 99, or 100% identical (or any range derivable therein) to all or part of any antibody provided herein. In still further aspects the isolated and/or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids from any of the sequences provided herein or a combination of such sequences.

In still further aspects, an antibody or polypeptide of the embodiments comprises one or more amino acid segments of the any of the amino acid sequences disclosed herein. For example, the antibody or polypeptide can comprise 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 amino acids in length, including all values and ranges there between, that are at least 80, 85, 90, 95, 96, 97, 98, 99, or 100% identical to any of the amino acid sequences disclosed herein. In certain aspects the amino segment(s) are selected from one of the amino acid sequences of a GRP78-binding antibody as provided herein.

In still further aspects, an antibody or polypeptide of the embodiments comprises an amino acid segment of the any of the amino acid sequences disclosed herein, wherein the segment begins at amino acid position 1, 2, 3, 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 in any sequence provided herein and ends at amino acid position 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 in the same provided sequence. In certain aspects the amino segment(s), or portions thereof, are selected from one of the amino acid sequences of a GRP78-binding antibody as provided herein.

In yet further aspects, an antibody or polypeptide of the embodiments comprises an amino acid segment that is at least 80%, 85%, 90%, 91%, 92%, 93%, 94%, 95%, 96%, 97%, 98%, 99% or 100% identical (or any range derivable therein) to a V, VJ, VDJ, D, DJ, J or CDR domain of a GRP78-binding antibody (as provided in Table 1A). For example, a polypeptide may comprise 1, 2 or 3 amino acid segment that are at least 80%, 85%, 90%, 91%, 92%, 93%, 94%, 95%, 96%, 97%, 98%, 99% or 100% identical (or any range derivable therein) to CDRs 1, 2, and/or 3 a GRP78-binding antibody as provided in Table 1A.

Selection of Phage-Displayed Accessible Recombinant Targeted Antibodies

Embodiments of the present disclosure relate to a novel and robust antibody discovery methodology, termed Selection of Phage-Display Accessible Recombinant Targeted Antibodies (SPARTA). The method of the present invention combines an in vitro screening step of a naive human antibody library against known tumor targets, with in vivo selections based upon tumor-homing capabilities of the pre-enriched antibody pool. This approach overcomes several rate-limiting challenges in the generation of human antibodies amenable to rapid translation into medical applications.

To discover target-specific, biologically active antibodies to common human cancers, the inventors conceived of a two-step in tandem methodology: Selection of Phage-displayed Accessible Recombinant Targeted Antibodies (termed SPARTA). Unlike blind selection approaches in which there is no knowledge of the target, SPARTA starts with a previously identified tumor cell surface target, against which an enriched pool of recombinant human antibodies is first generated from a large naive human library using a high throughput combination of phage- and yeast-display (Ferrara et al., 2012). Antibodies from this pool are subsequently selected directly in vivo for their tumor targeting attributes. The present inventors have pioneered the experimental use of in vivo peptide phage-display (Arap et al., 2002; Arap et al., 1998; Driessen et al., 2010; Kolonin et al., 2004; Kolonin et al., 2006; Ozawa et al., 2008; Pasqualini and Ruoslahti, 1996; Rajotte et al., 1998; Staquicini et al., 2011a; Staquicini et al., 2010; Staquicini et al., 2011b) and documented extensively that this approach provides exquisite advantages in identifying accessible target receptors in the unique context of the native tumor microenvironment. The inventors and other investigators have attempted to extend the in vivo methodology to antibody phage-display libraries, but with only modest success (Deramchia et al., 2012; Krag et al., 2006; Sanchez-Martin et al., 2015; Shukla et al., 2013) likely due to inherent technical constraints such as the critical need for helper phage "rescue", which leads to extremely low antibody display levels. Moreover, the presence of truncated antibodies and associated exposure of hydrophobic interfaces generally increase non-specific binding to nearly prohibitive background levels.

In the present application, the inventors have focused their efforts on two established cancer cell surface targets, Ephrin A5 (EphA5), a molecular target in human lung cancer (Staquicini et al., 2015), and 78 kDa glucose-regulated protein (GRP78), a relatively promiscuous target on the tumor cell surface of several human cancers (Arap et al., 2004; Dobroff et al., 2016; Ferrara et al., 2016). Generation of an enriched pool of human recombinant antibodies screened against EphA5 and GRP78 in vitro, along with the functional selection in vivo of the monoclonal antibody pools in preclinical models of human lung cancer and breast cancer (respectively) enabled the identification of single monoclonal antibody clones with favorable tumor-targeting properties. The individual monoclonal antibody clones against EphA5 and GRP78 consistently recognized and localized to their cognate tumor targets in vivo, and showed effective killing activity as ADCs. The inventors conclude that SPARTA is a broadly enabling platform for the generic selection of tumor-specific antibodies from large human phage-display antibody libraries, and it may therefore become a method-of-choice to select monoclonal antibodies against human cancers, and perhaps also against certain non-malignant diseases.

Embodiments according relate to a method for selecting phage displayed accessible recombinant targeted antibodies (SPARTA) comprising the steps of:

1. Serially screening a bacteriophage human recombinant antibody library comprising about $10^{10}$ to $10^{13}$, often about $10^{11}$ transducing units ("TU"), in vitro against immobilized recombinant antigens to provide a phage output pool of approximately $10^5$-$10^7$, more often approximately $10^6$ TU;
2. Transferring genetic material from the phage output pool to a yeast display vector and serially screening the modified yeast display vector against the immobilized recombinant antigens from 1-5 times (often at least twice) and optionally against orthologous recombinant antigens to eliminate cross reactivity, to provide a yeast output pool containing from $10^3$-$10^5$, often about $10^4$ TU;
3. Displaying the yeast output pool in phage (preferably phagemid) particles, in either mono- or multivalent format;
4. Administering the phage particles into a tumor bearing laboratory test animal and allowing the phage particles sufficient time to bind to the tumor, wherein the tumor expresses or likely expresses the antigen to which antibodies displayed in the yeast output pool bind;
5. Recovering tumor tissue from the laboratory test animal, recovering the antibody genes within the phage, e.g. by amplifying the genetic material obtained from the phage particles which bind to the tumor tissue, or by infection, and repeating steps 3-5 at least one additional time (e.g. 1, 2, 3, 4, 5 or 6 times).
6. Determining clonal diversity and ranking of individual components of the display vector for identification of lead antibody candidates for monoclonal antibodies; and
7. Optionally obtaining and sequencing the genetic material from phages which express the lead candidate proteins or peptides, introducing the obtained genetic material into an expression vector and introducing the expression vector into a cell for expression of the proteins or peptides.

Embodiments according to the present invention relate to a method for selecting phage displayed accessible recombinant targeted antibodies (SPARTA) comprising the steps:
1. Serial screening a bacteriophage human recombinant antibody library comprising about $10^{10}$ to $10^{13}$, often about $10^{11}$ transducing units ("TU"), in vitro against immobilized recombinant antigens ("the screened antigen") to provide a phage output pool of approximately $10^5$-$10^7$, more often approximately $10^6$ TU;
2. Transferring genetic material from the phage output pool to a yeast display vector and serial screening the modified yeast display vector against the immobilized recombinant antigens from 1-5 times (often at least twice) to provide a yeast output pool containing from $10^3$-$10^5$, often about $10^4$ TU;
3. Optionally and preferably negatively screening the yeast output pool from step 2 from at least one positive screen conducted and preferably from each of the positive screens conducted against orthologous recombinant antigens to minimize cross reactivity with the orthologous antigens;
4. Cloning the genetic material from the yeast output pool and displaying the genetic material in single or multivalent display vector format in phage (preferably phagemid) particles;
5. Administering the phage particles into a tumor bearing laboratory test animal and allowing the phage particles sufficient time to localize and bind to the tumor, wherein the tumor expresses or likely expresses the antigen to which antibodies displayed in the yeast output pool bind;
6. Recovering tumor tissue from the laboratory test animal, recovering the antibody genes within the phage by amplifying the genetic material obtained from the phage particles which bind to the tumor tissue or by infection and repeating steps 3-5 at least one additional time (e.g. 1, 2, 3, 4, 5, 6 or more times);
7. Determining clonal diversity and ranking of individual components of the display vector for identification of lead antibody candidates for monoclonal antibodies;
8. Obtaining and sequencing the genetic material from phages which express the lead candidate proteins or peptides, introducing the obtained genetic material into an expression vector and introducing the expression vector into a cell for expression of the proteins or peptides.

In preferred embodiments of the general method, the phage library initially screened and the subsequent vectors which are screened express scFv, Fab, Fab', F(ab')$_2$, Fd, Fv, dAb, or isolated CDR antibody fragments, often scFv or Fab fragments, most preferably scFv fragments. In preferred embodiments the initial (naïve) bacteriophage antibody library comprises about 1011 TU and the phage output pool after serial screening comprises about $10^6$ TU. In preferred embodiments, the bacteriophage is screened from 2-7 times (2, 3, 4, 5, 6 or 7, preferably 3-5 times, most often 3 times). In preferred aspects the recombinant antigen is an antigen from a tumor surface protein or polypeptide. In preferred aspects, the yeast display vector is screened serially at least twice, more often twice. In preferred embodiments, the yeast output pool after serial screening comprises about $10^4$ TU. In preferred embodiments, the output pools from each serial screening (e.g., the yeast output pool or the phagemid output pool) is negatively screened against orthologous proteins or peptides (often, proteins or peptides from the same family of proteins as the recombinant antigen to which the libraries are screened) to minimize or eliminate cross-reactivity. In preferred embodiments, the genetic material from the yeast output pool is cloned into phagemid particles (step 4) which express the genetic material multivalently. In preferred embodiments, the genetic material from the yeast output pool is cloned and incorporated into phagemid particles which are expressed in cells (preferably, eukaryotic cells and more preferably E. Coli or other eukaryotic cells carrying a helper plasmid such as a M13cp-dg3, M13K07, R408, VCSM13, R408d3 or KM13).

In preferred embodiments, the phage (preferably phagemid) display particles are serially screened three times. In preferred embodiments, after the first two (or more) screens, the genetic material from the phage, preferably a phagemid display is recloned back into the original (umodified) phage display vector, expressed in multivalent format (preferably, the phage display vector is a phagemid display vector expressed in eurkaryotic cells containing a helper plasmid and the phage/phagemid display vector is again screened (final screen in the serial screening). After the final screen of the phage/phagemid display vector, In certain preferred embodiments, the results of a given screen (e.g. a first "homing" screen or a final screen step in a serial screening), especially a phage/phagemid in vivo screen of tumor tissue, are collected and the number of bound phage particles in the tumor is assessed and/or compared against control (unbound/naive) tumor tissue, preferably using PCR techniques, especially including real-time PCR. In certain embodiments, the final in vivo screened phage/phagemid particles are cloned into a phage vector and the cloned phage vector is further tested in vivo for their ability to home and localize into tumor tissue selectively and compared to a standard (using control phage without antibody modification).

It is unexpected that the method according to the present invention will provide high polyclonality which allows the selection of diverse specific antibodies. Accordingly, the present method can provide particularly useful monoclonal antibodies or antibody fragments which can be used to produce monoclonal antibodies exhibiting unexpected binding to tumor tissue as well as favorable homing characteristics allowing the rapid development of therapeutic monoclonal antibodies heretofore unknown in the art.

In additional, more specific embodiments, the present invention is directed to a method for selecting phage displayed accessible recombinant targeted antibodies (SPARTA) comprising the steps of
1. Immobilizing a target tumor surface antigen (generally a recombinant target protein or peptide, often a tumor surface protein) on a binding surface, often the wells of a microtiter plate to produce an immobilized protein or peptide;
2. Exposing said protein or peptide on said binding surface to a naive bacteriophage library comprising a plurality of bacteriophage, each bacteriophage displaying at least one (preferably a multivalent single protein) heterologous protein or protein fragment (peptide) on the viral surface wherein the bacteriophage comprises genetic material encoding for the heterologous protein or protein fragment;

3. Allowing the bacteriophage library sufficient time to bind with the tumor surface protein to produce protein binding bacteriophage;
4. Isolating the protein binding bacteriophage to provide a bacteriophage output pool comprising bacteriphage which bind to the antigen;
5. Optionally, repeating steps 2-4 at least once serially with the protein binding bacteriophage pool obtained after each successive isolation (up to 10 times, often 1, 2, 3, 4, 5 or 6 times) to obtain a bacteriphage output pool having about $10^6$ TU;
6. Optionally, growing (amplifying) said protein binding bacteriphage in said output pool in a bacterial host after step 4 or after the last isolation pursuant to step 5 to increase the number of protein binding bacteriophage from said output pool;
7. Obtaining and sequencing the DNA within said protein binding bacteriophage to identify the interacting heterologous proteins or protein fragments;
8. Cloning the DNA for the interacting heterologous proteins or protein fragments obtained from step 7 into a yeast display system to provide a cloned yeast display system which displays said interacting heterologous proteins or protein fragments, wherein said yeast comprises genetic material encoding for the heterologous proteins or protein fragments;
9. Exposing said immobilized protein to said cloned yeast display system and allowing said yeast sufficient time to bind to said immobilized protein to provide protein binding yeast;
10. Isolating the protein binding yeast;
11. Repeating steps 9-10 from 1 to 5 times (e.g. 1, 2, 3, 4 or 5) with the yeast output obtained after each screening step to provide a yeast output pool comprising about $10^3$-$10^5$, often about $10^4$ TU;
12. Obtaining and preferably sequencing the DNA within said protein binding yeast to identify the interacting heterologous proteins or protein fragments;
13. Cloning the DNA for the interacting heterologous proteins or protein fragments obtained from step 12 into a plasmid vector (preferably, a phagemid vector having a f1 origin of replication) to provide a polyclonal phage or phagemid vector pool and introducing/transforming a bacteria to provide a polyclonal multivalent phage display pool which displays said interacting heterologous proteins or protein fragments (in the case of the phagemid display vector the bacteria used to express the vector contains a helper plasmid, and is preferably *E. coli* carrying the M13cp-dg3 helper plasmid);
14. Administering said phage display pool obtained from step 13 into a tumor-bearing laboratory test animal having tumor tissue which expresses said target tumor surface protein and allowing sufficient time for said phage/phagemid pool to bind to said target tumor surface protein in said animal;
15. Collecting said tumor tissue from said laboratory test animal;
16. Isolating phage or phagemid particles bound to said tumor tissue;
17. Optionally, quantifying the binding of phage or phagemid particles to tumor tissue (e.g. by quantitative PCR) and comparing the binding of tumor tissue with a standard (e.g. binding of the phage particles to non-tumor tissue or to a monoclonal antibody with known tumor binding specificity);
18. Obtaining and optionally sequencing the DNA within said phage particles of step 16 to identify the heterologous proteins or protein fragments which bind to tumor tissue;
19. Amplifying the DNA provided in step 18, recloning the DNA into an unmodified display phage or phagemid display vector and repeating steps 12-17 at least one additional time (often 1, 2, 3, 4, 5 or 6 times, preferably at least two additional times- a serial screening);
20. Isolating the phage or phagemid particles from the final screen of step 19.
21. Determining the clonal diversity and ranking of individual components of the display vector for identification of lead protein or peptide candidates for monoclonal antibodies.
22. Obtaining DNA from phage or phagemid particles subjected to step 21 and producing antibodies (preferably antibody fusion proteins such as scFv-Fc fusions) by cloning the DNA into plasmid vectors, transfecting eukaryotic cells with said plasmid vectors and growing said eukaryotic cells; and
23. Isolating said antibodies from said eukaryotic cells and/or media in which said eurkaryotic cells are grown.

Embodiments further include an optional step of negatively selecting the antibody pools of steps 4, 5, 6, 10, 12, 16 and/or 19 and/or the antibodies of claim 21 to minimize or eliminate binding to orthologous non-target antigens.

Embodiments often include a human recombinant tumor surface antigen as target, a human scFv library as the bacteriophage library (preferably naive).

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 12A) A naive human scFv library (~$10^{11}$ TU) is first screened in vitro against immobilized recombinant antigens. The phage output pool (~$10^6$ TU) is subsequently transferred to a yeast display vector for two additional screening steps. After rounds of positive and negative sorting, the yeast output pool (~$10^4$ TU) is expressed multivalently in phage particles and administered i.v. into tumor-bearing mice. Tumor-homing phage particles are recovered, amplified by PCR and re-expressed in multivalent format for two additional rounds of in vivo selection. Clonal diversity and ranking are determined after NGS. (FIGS. 12B and 12C) Flow cytometry profiles and ELISA. Positive binders are shown for selected anti-EphA5 or anti-GRP78. Each dot in the FACS plot (top-right quadrant) represents an individual yeast antibody-displaying clone. ELISA carried out with the corresponding recombinant antigen confirmed binding specificity. Open circles represent individual data points. (FIGS. 12D and 12E) Following the screening steps in vitro, three rounds of selection in vivo were performed in mice bearing human lung cancer xenografts for EphA5, or isogenic mammary tumors for GRP78. Open circles represent individual data points.

(FIG. 15B) Binding to antigens expressed on the cell surface was tested by standard ELISA on cells. (FIG. 15B) EphA5-positive (H460) and EphA5-negative (H226) cells grown in 96-well plates were exposed to anti-EphA5 clones or to a control phage. All four monoclonal antibodies bound specifically to H460 lung cancer cells. (FIG. 15B, lower panel) Similarly, all anti-GRP78 clones bound to GRP78-expressing breast cancer cells (MCF7) whereas a control phage showed only background binding.

(FIG. 20, upper panel) The number of EphA5 molecules on the tumor cell surface was quantified on a representative panel of human lung cancer cell lines (n=4), as indicated. (FIG. 20, lower panel) Quantification of cell surface GRP78 was performed on Ef43.fgf4 breast cancer cells. GRP78-silenced Ef43.fgf4 cells served as control. Open circles represent individual data points.

FIG. 22. Sequences of selected anti-EphA5 and anti-GRP78 HCDR3.

DESCRIPTION OF ILLUSTRATIVE EMBODIMENTS

Figure 1:
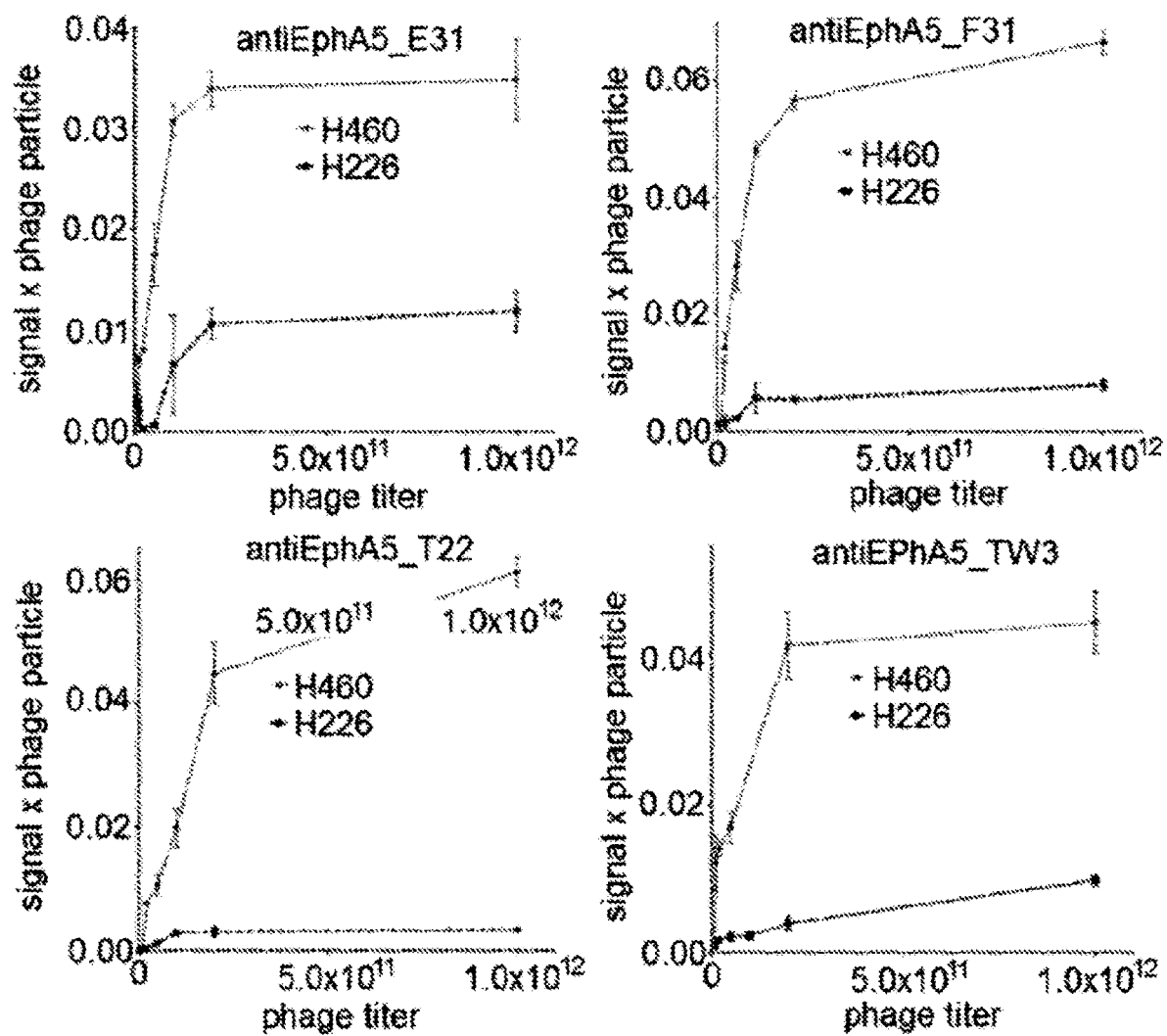
FIG. 1. Whole cell phage-ELISA assay to demonstrate specific binding of anti-EphA5 antibodies to native EphA5 target expressed on H460 human lung carcinoma cells in vitro. The binding to H460 cells was higher than H226 in all cases.

The present disclosure provides targeting antibodies, antigen binding fragments thereof, immunoconjugates comprising the foregoing, and therapeutic methods for the treatment of cancers. In some aspects, the antibodies are human monoclonal anti-EphA5 antibodies or scFvs thereof, such as for the treatment of cancers expressing EphA5. The disclosure also provides an effective strategy to generate highly specific antibodies which recognize the target antigen in its native conformation within the relevant physiological context.

I. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

The terms "antibody" and "immunoglobulin" are used interchangeably in the broadest sense and include monoclonal antibodies, polyclonal antibodies, multivalent antibodies, and multispecific antibodies, regardless of how they are produced (i.e., using immunization, recombinant, synthetic methodologies).

The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about sss25 kD) and one "heavy" chain (about 50-70 kD). The N-terminus of each chain defines a variable region of about 100 to 110 or more amino acids primarily responsible for antigen recognition. The terms "variable light" chain, domain, region and component are used interchangeably, are abbreviated by "VL" or "$V_L$" and refer to the light chain of an antibody or antibody fragment. Similarly, terms "variable heavy" chain, domain, region and component are used interchangeably, are abbreviated by "VH" or "$V_H$" and refer to the heavy chain of an antibody or antibody fragment.

The terms "anti-EphA5 antibody", "EphA5 antibody" and "EphA5-specific specific antibody" are used interchangeably and refer to antibodies that are specific for and bind specifically to EphA5. EphA5 antibodies of the invention may be of any type (e.g., IgG, IgE, IgM, IgD, IgA, and IgY), class (e.g., IgG1, IgG2, IgG3, IgG4, IgA1 and IgA2) or subclass of immunoglobulin molecule.

The terms "anti-GRP78 antibody", "GRP78 antibody" and "GRP78-specific antibody" are used interchangeably and refer to antibodies that are specific for and bind specifically to GRP78. GRP78 antibodies of the invention may be of any type (e.g., IgG, IgE, IgM, IgD, IgA, and IgY), class (e.g., IgG1, IgG2, IgG3, IgG4, IgA1 and IgA2) or subclass of immunoglobulin molecule.

As used herein, the terms "specific", "specifically reactive", "specific binding", "specifically binds" and "binds specifically" when used in connection with EphA5 or GRP78 antibodies and antigen binding fragments thereof refer to the selective binding to EphA5 or GRP78, respectively as determined using standard immunological detection assays, including without limitation ELISA, immunoblot, Western Blot, immunohistochemical and immunoprecipitation assays, under conditions typically employed for conducting such assays. EphA5 or GRP78 antibodies and antigen binding fragments thereof may be tested for such specificity using methods well known in the art and as described herein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity).

The terms "full length antibody," "intact antibody" and "whole antibody" are used herein interchangeably, to refer to an antibody in its substantially intact form, not as antibody fragments as defined below. The terms particularly refer to an antibody with heavy chains that contain the Fc region. A full length antibody can be a native sequence antibody or an antibody variant.

"Antigen binding fragments" of antibodies comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment which consists of a VH domain; (vii) isolated CDR regions; (viii) F(ab')$_2$ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) "linear antibodies" comprising a pair of tandem Fd, segments (VH-CH1-VH-CH1) which, together with complementary light chain polypeptides, form a pair of antigen binding regions.

As used herein, the term "single-chain Fv" or "scFv" or "single chain" antibody refers to antibody fragments comprising th VH and VL domains of antibody, wherein these domains are present in a single polypeptide chain. Generally, the Fv polypeptide further comprises a polypeptide linker between the VH and VL domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. The monoclonal antibodies of the invention may be generated by recombinant DNA methods, and are sometimes referred to as "recombinant antibodies" or "recombinant monoclonal antibodies" herein.

Recombinant antibody fragments may be isolated from phage antibody libraries using techniques well known in the art. See, for example, Clackson et al., 1991, Nature 352: 624-628; Marks et al., 1991, J. Mol. Biol. 222: 581-597. Recombinant antibody fragments may be derived from large phage antibody libraries generated by recombination in bacteria (Sblattero and Bradbury, 2000, Nature Biotechnology 18:75-80; and as described herein). Polynucleotides encoding the VH and VL components of antibody fragments (i.e., scFv) may be used to generate recombinant full length immunoglobulins using methods known in the art (see, for example, Persic et al., 1997, Gene 187: 9-18).

As used herein, "linker" or "spacer" refers to a molecule or group of molecules that connects two molecules, such as VH and VL genes or polypeptides (i.e., in a scFv), and serves to place the two molecules in a preferred configuration.

The terms "label" and "detectable label" refer to a detectable compound or composition which is conjugated directly or indirectly to the antibody so as to generate a "labeled" or "detectably labeled" antibody. The label may be detectable by itself (e.g. radioisotope labels or fluorescent labels) or, in the case of an enzymatic label, may catalyze chemical alteration of a substrate compound or composition which is detectable. A great number of such labels are known in the art, including without limitation protein tags, radioisotopes, metal chelators, enzymes, fluorescent compounds (dyes, proteins, chemicals), bioluminescent compounds, and chemiluminescent compounds.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

A "display vector" refers to a vector used to create a cell or virus that displays, i.e., expresses a display protein comprising a heterologous polypeptide, on its surface or in a cell compartment such that the polypeptide is accessible to test binding to target molecules of interest, such as antigens.

A "display library" refers to a population of display vehicles, often, but not always, cells or viruses. The "display vehicle" provides both the nucleic acid encoding a peptide as well as the peptide, such that the peptide is available for binding to a target molecule and further, provides a link between the peptide and the nucleic acid sequence that encodes the peptide. Various "display libraries" are known to those of skill in the art and include libraries such as phage, phagemids, yeast and other eukaryotic cells, bacterial display libraries, plasmid display libraries as well as in vitro libraries that do not require cells, for example ribosome display libraries or mRNA display libraries, where a physical linkage occurs between the mRNA or cDNA nucleic acid, and the protein encoded by the mRNA or cDNA.

A "phage expression vector" or "phagemid" refers to any phage-based recombinant expression system for the purpose of expressing a nucleic acid sequence in vitro or in vivo, constitutively or inducibly, in any cell, including prokaryotic, yeast, fungal, plant, insect or mammalian cell. A phage expression vector typically can both reproduce in a bacterial cell and, under proper conditions, produce phage particles. The term includes linear or circular expression systems and encompasses both phage-based expression vectors that remain episomal or integrate into the host cell genome.

A "phage display library" refers to a "library" of bacteriophages on whose surface is expressed exogenous peptides or proteins. The foreign peptides or polypeptides are displayed on the phage capsid outer surface. The foreign peptide can be displayed as recombinant fusion proteins incorporated as part of a phage coat protein, as recombinant fusion proteins that are not normally phage coat proteins, but which are able to become incorporated into the capsid outer surface, or as proteins or peptides that become linked, covalently or not, to such proteins. This is accomplished by inserting an exogenous nucleic acid sequence into a nucleic acid that can be packaged into phage particles. Such exogenous nucleic acid sequences may be inserted, for example, into the coding sequence of a phage coat protein gene. If the foreign sequence is "in phase" the protein it encodes will be expressed as part of the coat protein. Thus, libraries of nucleic acid sequences, such as a genomic library from a specific cell or chromosome, can be so inserted into phages to create "phage libraries." As peptides and proteins representative of those encoded for by the nucleic acid library are displayed by the phage, a "peptide-display library" is generated. While a variety of bacteriophages are used in such library constructions, typically, filamentous phage are used (Dunn, 1996 Curr. Opin. Biotechnol. 7:547-553). See, e.g., description of phage display libraries, below.

A "yeast display library" refers to a "library of yeast on whose surface is expressed exogenous peptides or proteins. A yeast surface display is an alternative method for isolating and engineering antibody fragments (scFv, Fab, Fab', F(ab')$_2$, Fd, Fv, dAb, preferably isolated scFv) from immune and non-immune libraries, and has been used to isolate recombinant antibodies with binding specificity to a variety of proteins and peptides. In the yeast display system, yeast display libraries are produced by cloning the pool of genes coding for antibody fragments into vectors that can be transformed into the yeast. The transformed antibody genes encoding for exogenous peptides or proteins are displayed on the surface of the yeast, often via fusion to an α-agglutinin yeast adhesion receptor, which is located in the yeast cell wall. Like phage display, yeast display provides a direct connection between genotype and phenotype. A plasmid containing the gene of interest is contained within yeast cells and the encoded antibody is expressed on the surface. The display level of each yeast cell is variable, with each cell displaying from approximately $1 \times 10^4$ to $1 \times 10^5$ copies of the scFv. There are usually 3-5 rounds of enrichment of target antigen-binding clones. The antibody expressed by a single yeast colony is evaluated for specificity and reproducibility. If the antibody has the required functionality, the antibody gene is sequenced as part of antibody validation. Screening of antibody variation of surface expression and avidity can be quantified using fluorescence activated cell sorting (FACS), which measures both the strength of antigen binding and amount of antibody expression on the yeast cell surface using separate tags on the antibody and antigen. FACS binding assays provide a much more quantitative way of assessing high binding affinity and selectivity for the antigens and offer the ability to accurately control selection parameters (binding population percentage, signal normalization, and desired binding affinities) by flow cytometry.

"Serial screening" or "screened serially" is a term used to describe the screening of a phage, yeast, phagemid or other library against an antigen, preferably an immobilized antigen pursuant to the SPART method described herein where the library is screened, bound particles of the library are then isolated and collected and the isolated particles are screened against the same antigen (which may be the same or preferably a different sample of the same antigen). This serial screening process will occur at least twice and in many instances as many as 3-10, often 3-6 times to provide a final pool of particles, the genetic material of which can be isolated, cloned and introduced into an alternative library for further screening. In most instances the serial screening process occurs without isolating the DNA from the particles which have been screened. In other instances, the DNA from the particles which have been screened are isolated and recloned into a naive display vector used in the first screen before each subsequent screening.

The term "cloning" is used to describe the methods of isolating, amplifying and transferring/inicorporating genetic material expressing exogenous proteins or peptides identified through screening from one display vector (e.g. a phage display vector) into an unmodified display vector (which may be same type of display vector or a different type of display vector) for further screening or an expression vector for expressing the identified protein or peptide (e.g., to produce antibody fragments identified through the screening methodology). Cloning techniques which are used in the present invention are well known in the art. See, for example the following references, which are incorporated by reference herein. Andris-Widhopf, et al., (2011); Barbas, et a;. (2001); Ferrara, et al., (2012); Hoogenboom, et a.1, (1991); Huston, etal., (1988); Krebber, etal., (1997); Marks, J. D., & Bradbury, A. (2004); and Schaefer, et al., (2010).

IIA. EphA5 Antibodies

Eph receptor tyrosine kinases and their ligands (ephrin) regulate a wide range of cell contact-dependent signaling that can effect cell proliferation, migration, morphology, adhesion, and invasion (Pitulescu et al. Genes & Dev., 24:2480-2492, 2010). However, elevated EphA5 has also been found in variety of cancer cell types, such as lung cancer and brain cancer. Studies herein demonstrate that inhibition of EphA5 activity is effective for inhibiting cancer cell proliferation and angiogenesis in tumor tissues. Moreover, EphA5-binding antibodies provided here were found to be effective for inhibiting EphA5 activity and cancer cell growth. Thus, antibodies of the embodiments provide new effective methods for treating cancers and inhibiting angiogenesis.

In some embodiments, the present disclosure provides anti-EphA5 human monoclonal antibodies. These antsibodies are selected from extremely large recombinant naive human antibody libraries by using a combination of phage and yeast display. This combined approach allows for the selection of populations of high affinity binders as well as the elimination of antibodies with undesired cross-reactivities. In addition, the in vitro selected population is further selected by means of a in vivo selection strategy in mice bearing xenograft tumors using both mono- and multivalent phage display.

The phage antibody clones recovered from the tumor tissue have two desirable properties. First, they have tumor homing capacity. Second, they recognize the target in its in vivo conformation and physiological context. Tumor homing antibody clones generated using the methods of the invention are identified through their HCDR3 using next generation sequencing and a tailored bioinformatics analysis. Antibody clones are ranked by abundance and the top ranking clones are then rescued by an inverse-PCR based strategy and produced as single clones. Selected clones may then be evaluated for cell binding and cell internalization properties, and ultimately for cytotoxicity.

Among the various aspects of the invention, anti-EphA5 antibodies are provided. The anti-EphA5 antibodies of the invention are specific for EphA5. Preferred anti-EphA5 antibodies are isolated, purified or semi-purified such that they retain specificity in the desired application. Most preferred for therapeutic applications in the treatment of cancers expressing EphA5 are fully human monoclonal antibodies.

Another aspect of the invention relates to antigen binding fragments of EphA5 antibodies which are specific for EphA5. Such fragments may be generated from intact antibodies or through the use of recombinant technology. For example, an EphA5 antibody antigen binding fragment may be a single chain antibody, or scFv. In one embodiment, an EphA5 human monoclonal antibody or antigen binding fragment thereof comprises the HCDR3 amino acid sequence of SEQ ID NOs: 5, 13, 21, or 29. In another embodiment, an EphA5 human monoclonal antibody or antigen binding fragment thereof comprises a heavy chain variable region having an amino acid sequence that is at least 80%, preferably about 90%, 91%, 92%, 93% or 94%, and most preferably about 95% or more, identical to SEQ ID NOs: 1, 9, 17, or 25. In another embodiment, an EphA5 human monoclonal antibody of the invention comprises a light chain variable region having an amino acid sequence that is at least 80%, preferably about 90%, 91%, 92%, 93% or 94%, and most preferably about 95% or more, identical to SEQ ID NOs: 2, 10, 18, or 26. The EphA5 antibodies of the invention may be of the immunoglobulin classes IgA, IgD, IgE, IgG and IgM and subclasses thereof.

In one embodiment, phage display systems are used to select single chain antibodies specific for EphA5. Once isolated, polynucleotides encoding the EphA5 scFvs may be cloned into expression vectors designed to express full length immunoglobulins as well as fragments thereof having the same specificity. Briefly, to generate a full length antibody, the VH and VL genes of the single chain antibody are cloned into an immunoglobulin scaffold (i.e., IgG) vector, expressed, and dimerized in order to convert the single chain into a full antibody. The immunoglobulin scaffold may be selected from any of the five major classes of immunoglobulins (IgA, IgD, IgE, IgG and IgM), and subclasses thereof (i.e., IgG-1). Exemplary selection and screening strategies are described in the Examples, EphA5 antibodies and antigen binding fragment thereof may be detectably labeled as is generally known. The label may be detectable by itself (e.g. radioisotope labels or fluorescent labels) or, in the case of an enzymatic label, may catalyze chemical alteration of a substrate compound or composition which is detectable. A great number of such labels are known in the art, including without limitation protein tags, radioisotopes, metal chelators, enzymes, fluorescent compounds (dyes, proteins, chemicals), bioluminescent compounds, and chemiluminescent compounds. Such labeled EphA5 antibodies and antigen binding fragments thereof may be used, for example, to immunologically detect or image EphA5 expressing cells and tumors.

IIB. GRP78 Antibodies

In some embodiments, the present disclosure concerns anti-GRP78 human monoclonal antibodies. These antibodies are selected from extremely large recombinant naive human antibody libraries by using a combination of phage and yeast display. This combined approach allows for the selection of populations of high affinity binders as well as the elimination of antibodies with undesired cross-reactivities. In addition, the in vitro selected population is further selected by means of an in vivo selection strategy in mice bearing xenograft tumors using both mono- and multivalent phage display.

The phage antibody clones recovered from the tumor tissue have two desirable properties. First, they have tumor homing capacity. Second, they recognize the target in its in vivo conformation and physiological context. Tumor homing antibody clones generated using the methods of the invention are identified through their HCDR3 using next generation sequencing and a tailored bioinformatics analysis. Antibody clones are ranked by abundance and the top ranking clones are then rescued by an inverse-PCR based strategy and produced as single clones. Selected clones may then be evaluated for cell binding and cell internalization properties, and ultimately for cytotoxicity.

Among the various aspects of the invention, anti-GRP78 antibodies are provided. The anti-GRP78 antibodies of the invention are specific for GRP78. Preferred anti-GRP78 antibodies are isolated, purified or semi-purified such that they retain specificity in the desired application. Most preferred for therapeutic applications in the treatment of cancers expressing GRP78 are fully human monoclonal antibodies.

Another aspect of the invention relates to antigen binding fragments of GRP78 antibodies which are specific for GRP78. Such fragments may be generated from intact antibodies or through the use of recombinant technology. For example, an GRP78 antibody antigen binding fragment may be a single chain antibody, or scFv. In one embodiment, an GRP78 human monoclonal antibody or antigen binding fragment thereof comprises the HCDR3 of SEQ ID NO: 41, SEQ ID NO: 49, or SEQ ID NO: 57. In another embodiment, an GRP78 human monoclonal antibody or antigen binding fragment thereof comprises a heavy chain variable region having an amino acid sequence that is at least 80%, preferably about 90%, 91%, 92%, 93% or 94%, and most preferably about 95% or more, identical to SEQ ID NO: 37, SEQ ID NO: 45, or SEQ ill) NO: 53. In another embodiment, an GRP78 human monoclonal antibody of the invention comprises a light chain variable region having an amino acid sequence that is at least 80%, preferably about 90%, 91%, 92%, 93% or 94%, and most preferably about 95% or more, identical to SEQ ID NO: 38, SEQ ID NO: 46, or SEQ LD NO: 54. The GRP78 antibodies of the invention may be of the immunoglobulin classes IgA, IgD, IgE, IgG and IgM and sub classes thereof.

In one embodiment, phage display systems are used to select single chain antibodies specific for GRP78. Once isolated, polynucleotides encoding the GRP78 scFvs may be cloned into expression vectors designed to express full length immunoglobulins as well as fragments thereof having the same specificity. Briefly, to generate a full length antibody, the VH and VL genes of the single chain antibody are cloned into an immunoglobulin scaffold (i.e., IgG) vector, expressed, and dimerized in order to convert the single chain into a full antibody. The immunoglobulin scaffold may be selected from any of the five major classes of immunoglobulins (IgA, IgD, IgE, IgG and IgM), and subclasses thereof (i.e., IgG-1). Exemplary selection and screening strategies are described in the Examples, infra.

GRP78 antibodies and antigen binding fragment thereof may be detectably labeled as is generally known. The label may be detectable by itself (e.g. radioisotope labels or fluorescent labels) or, in the case of an enzymatic label, may catalyze chemical alteration of a substrate compound or composition which is detectable. A great number of such labels are known in the art, including without limitation protein tags, radioisotopes, metal chelators, enzymes, fluorescent compounds (dyes, proteins, chemicals), bioluminescent compounds, and chemiluminescent compounds. Such labeled GRP78 antibodies and antigen binding fragments thereof may be used, for example, to immunologically detect or image GRP78 expressing cells and tumors.

Another aspect of the invention relates to polyriucloetides encoding the EphA5 or GRP78 antibodies and antigen binding fragments of the invention, and includes vectors comprising such polynucleotides as well as host cells comprising such vectors.

In yet another aspect, the invention provides therapeutic compositions, including without limitation immunoconjugates, such as antibody-drug conjugates (ADC), which comprise an anti-EphA5 or anti-GRP78 antibody or antigen binding fragment thereof conjugated to a cytotoxic agent such as a chemotherapeutic agent, a drug, a growth inhibitory agent, a toxin, or a radioactive isotope. In related aspect, the invention further provides methods of using the immunoconjugates for the treatment of patients with neoplasms expressing EphA5 or GRP78 respectively. Antibody-drug conjugates are a new class of highly potent biopharmaceutical drugs designed as a targeted therapy for the treatment of patients with cancer. ADCs are complex molecules comprising an antibody or an antibody fragment linked via a stable linker to a biological active cytotoxic payload or drug. By combining the unique targeting capabilities of monoclonal antibodies with the cancer-killing ability of cytotoxic drugs, antibody-drug conjugates allow sensitive discrimination between healthy and diseased tissue.

In certain embodiments, an antibody or a fragment thereof that binds to at least a portion of EphA5 or GPR78 protein and inhibits EphA5 or GPR78 signaling and cancer cell proliferation are contemplated. The antibody may be any immunologic binding agent, such as IgG, IgM, IgA, IgD, IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-EphA5 or anti-GRP78 antibody is a monoclonal antibody or a humanized antibody.

Thus, by known means and as described herein, polyclonal or monoclonal antibodies, antibody fragments, and binding domains and CDRs (including engineered forms of any of the foregoing) may be created that are specific to EphA5 or GRP78 protein, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of VL, VH, CL, and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')$_2$ fragments, a bivalent fragment comprising two linked Fab fragments; (vii) single chain Fv molecules ("scFv"), wherein a VH domain and a VL domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (U.S. Patent App. Pub. 20050214860). Fv, scFv, or diabody molecules may be stabilized by the incorporation of disulphide bridges linking the VH and VL domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen, such as a EphA5 or GRP78 extracellular domain (ECD) protein, in order to produce antibodies specific for EphA5 or GRP 78 protein. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a EphA5 or GRP78 antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

Plasma B cells (CD45+CD5−CD19+) may be isolated from freshly prepared mouse peripheral blood mononuclear cells of immunized mice and further selected for EphA5 or GRP78 binding cells. After enrichment of antibody producing B cells, total RNA may be isolated and cDNA synthesized. DNA sequences of antibody variable regions from both heavy chains and light chains may be amplified, constructed into a phage display Fab expression vector, and transformed into E. coli. EphA5 or GRP78 specific binding Fab may be selected out through multiple rounds enrichment panning and sequenced. Selected EphA5 or GRP78 binding hits may be expressed as full length IgG in mouse and mouse/human chimeric forms using a mammalian expression vector system in human embryonic kidney (HEK293)

cells (Invitrogen) and purified using a protein G resin with a fast protein liquid chromatography (FPLC) separation unit.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in: Marks (1992); Stemmer (1994); Gram et al. (1992); Barbas et al. (1994); and Schier et al. (1996).

It is fully expected that antibodies to EphA5 or GRP78 will have the ability to neutralize or counteract the effects of EphA5 or GRP78 respectively regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro, although in most embodiments, the proteins are recombinant. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds EphA5 or GRP78.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against EphA5 or GRP78, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabel s, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

III. Treatment of Diseases

Certain aspects of the present embodiments can be used to prevent or treat a disease or disorder associated with EphA5 or GRP78 signaling. Signaling of EphA5 or GRP78 may be reduced by any suitable drugs to prevent cancer cell proliferation. Preferably, such substances would be an anti-EphA5 antibody.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that inhibits the EphA5 or FRP78 signaling.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

A. Pharmaceutical Preparations

Where clinical application of a therapeutic composition containing an inhibitory antibody is undertaken, it will generally be beneficial to prepare a pharmaceutical or therapeutic composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 ug/kg/body weight to about 1000 mg/kg/body weight (this such range includes intervening doses) or more per administration, and any range derivable therein. In non-limiting examples of a derivable range from the numbers listed herein, a range of about 5 μg/kg/body weight to about 100 mg/kg/body weight, about 5 μg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, intravaginal or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. clp B. Combination Treatments In certain embodiments, the compositions and methods of the present embodiments involve an antibody or an antibody fragment against EphA5 and/or GRP78 to inhibit its activity in cancer cell proliferation, in combination with a second or additional therapy. Such therapy can be applied in the treatment of any disease that is associated with EphA5- or GRP78-mediated cell proliferation. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

---
A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A
---

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

i. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and angui dine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine,plicomycin, gemcitabien, navelbine, farnesyl-protein tansferase inhibitors, transplatinum, and pharmaceutically acceptable salts, acids, or derivatives of any of the above, ii. Radiotherapy Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

iii. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody—drug conjugates (ADCs) comprise monoclonal antibodies (MAbs) that are covalently linked to cell-killing drugs (FIG. 1). This approach combines the high specificity of MAbs against their antigen targets with highly potent cytotoxic drugs, resulting in "armed" MAbs that deliver the payload (drug) to tumor cells with enriched levels of the antigen (Carter et al., 2008; Teicher 2014; Leal et al., 2014). Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach (Teicher 2009) and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., Mycobacterium bovis, Plasmodium falciparum, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

iv. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. Kits and Diagnostics

In various aspects of the embodiments, a kit is envisioned containing therapeutic agents and/or other therapeutic and delivery agents. In some embodiments, the present embodiments contemplates a kit for preparing and/or administering a therapy of the embodiments. The kit may comprise one or more sealed vials containing any of the pharmaceutical compositions of the present embodiments. The kit may include, for example, at least one EphA5 antibody as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate

Example 1— Generation of Anti-EphA5 Specific scFv Antibodies

In vitro scFv antibody selection: Recombinant human EphA5 antigen (R&D Biosystems) was biotinylated (EZ-Link™ Sulfo-NHS-LC-LC-Biotin, Life Technologies), according to the manufacturer instructions. Biotinylated EphA5 antigen was used for the in vitro phage and yeast display selections. Briefly, the scFv naive library cloned into the pDNA5 vector was expressed on phage particles. Approximately $10^{12}$ phage particles were incubated with streptavidin-coated magnetic beads (Dynabeads, Life Technologies) saturated with the biotinylated antigen, and 2 rounds of selection were performed. The selected scFv population was subcloned into the pDNL6 yeast vector and transformed into yeast.

After induction of the yeast culture, the scFvs were displayed on the yeast cell surface. The cells were incubated with the biotinylated antigen at 100 nM concentration and the cells displaying the higher affinity binders were sorted by flow cytometry. After the 2nd round, 10,000 antigen-binding yeast cells were sorted and the corresponding displayed scFv genes were amplified from the pDNL6 vector by PCR. The selected scFv genes were cloned back into the phagemid pDAN5 vector and displayed on multivalent phage particles (3-5 copies of the scFv were displayed per particle).

In vivo scFv antibody selection: The anti-EphA5 scFv phage population ($10^{11}$ phage particles from the in vitro pre-selected multivalent phage population) was injected intravenously in 3 nude mice bearing xenograft H460 human lung cancer derived tumors. After 3h from the injection, the mice were sacrificed and the tumor and control tissues were harvested. The tumor homing phage rescued from the tumor tissue of the 3 mice were amplified and mixed in equimolar amounts. The in vivo selection was reiterated for 2 additional cycles. At the end of the $3^{rd}$ cycle, the scFv genes were amplified by PCR from the pDAN5 plasmid DNA extracted from the tissue and prepared for next generation sequencing (NGS). MiSeq (Illumina) paired-end sequencing, combined with a bioinformatic analysis based on the in house developed AbMining Toolbox software were used to identify the unique $V_H$ domains of the tumor homing scFv genes.

Identification of scFv gene candidates and rescue: The AbMining Toolbox software analysis relies on the recognition of the HCDR3 sequence of each scFv gene, a signature element in all antibodies. The sequenced tumor homing clones were identified based on their HCDR3 and ranked according to their relative abundance in the tissue. The most abundant clones identified in each round of in vivo selection were chosen as candidates for further characterization. Once identified, the clones of interest were rescued from the selection output by means of an inverse PCR-based strategy (D'Angelo et al., 2014, mAbs 6(1): 160-172). Briefly, 2 back-to-back primers were designed on the scFv-specific HCDR3 DNA sequence and used for an inverse PCR using the pDAN5 plasmid DNA extracted from the tumor tissue harvested after each selection round. The amplicon obtained are collections of selected HCDR3-specific scFv genes in the context of the phagemid vector pDAN5. After DNA purification, the amplicons were ligated and transformed into bacteria. Upon sequencing confirmation, the clones were produced as mono- or multi-valent phage or as Ig-like minibodies (Di Niro et al., 2007, BMC Biotechnology 7:46) into CHO-S cells for further characterization.

Various anti-EphA5 scFv clones were further characterized. Three of the most abundant scFv clones identified were sequenced to determine their full length amino acid sequences, presented below. The VL and VH domains are listed below in Table 1, along with the CDRs.

```
antiEphA5_E31 scFv amino acid sequence
                              (SEQ ID NO: 33)
SYELIQPPSVSVAPGQTARITCGGSNIRSKSVHWY

QQKPGQAPVLVVYDDSDRPSGIPERFSGSNSGNTA

TLTISRVEAGDEADYYCQVWDSSSDHWVFGGRTKV

TVLSGGSTTTSYNVYYTKLSSSGTQVQLVESGGGL

VQPGGSLRLSCAASGFTFSSYAMSWVRQAPGKGLE

WVSAISGSGGSTYYADSVKGRFTISRDNSKNTLYL

QMNSLRAEDTAVYYCATHAAAGDYWGQGTLVTVSS antiEphA5_F31 scFv amino acid sequence
                              (SEQ ID NO: 34)
SYELTQPPSVSVAPGKTARITCEGNNIGSKGVHWY

QQKPGQAPALVVYDGSDRPSGIPERFSGSNSGNTA

TLTISRVEAGDEADYYCQVWDNSSDHPNYVFGTRT

KLTVLSGGSTKTSYNVYYTKLSSSGTQVQLVETGG

GLVQPGGSLRLSCAASGFTFSSYAMSWVRQAPGKG

LEWVSAISGSGGSTYYADSVKGRFTISRDNSKNTL

YLQMNSLRAEDTAVYYCARVAAGDYWGQGTLVTVS

S antiEphA5_TW3 scFv amino acid sequence
                              (SEQ ID NO: 35)
DIVMTQTPLSLPVTPGEPASISCRSSQSLLHSNGY

NYVDWYLQKPGQPPHLLIYLGSNRASGVPDRFSGS

GSGTDFTLKISRVEAEDVGVYYCMQGLQDPRTFGQ

GTKVEIKSGGSTITSYNVYYTKLSSSGTQVQLVES

GGGLVQPGGSLRLSCAASGFAFSNYAMSWVRQAPG

KGLEWVSGISGSGGSTYYADSVKGRFTISRDNSKN

TLYLQMNSLRAEDTAVYYCAREGAFGGRKGQGTLV

TVSS antiEphA5_T22 scFv amino acid sequence
                              (SEQ ID NO: 36)
QPVLTQSSSLSASPGASVSLTCTLRSGINVGPYRM

YWYQQKPGSPPQYLLSYKSDSDTQQASGVPSRFSG

SKDASANAGILLISGLQSEDEADYYCMIWHNNAVV

FGGGTKLTVLSGGSTITSYNVYYTKLSSSGTQVQL

VQSGTEVKKPGASVKVSCKVSGYSLSELSMHWVRQ

APGKGLEWMGSFDPEDGETTYAQRFQGRVTMTEDT

STDTAYMELRSLTSDDTAVYYCAREIWSGYAYFDL

WGRGTLVTVSS
```

TABLE 1

Amino acid sequences and CDRs of scFv clones.

| | Heavy Chain Sequence | | | Light Chain Sequence | | |
|---|---|---|---|---|---|---|
| | CDR1 | CDR2 | CDR3 | CDR1 | CDR2 | CDR3 |
| | Amino acid sequence | | | Amino acid sequence | | |
| E31 | GFTFSSYA MS (SEQ ID NO: 3) | AISGSGGST YYADSVKG (SEQ ID NO: 4) | HAAAGDY (SEQ ID NO: 5) | GGSNIRSK SVH (SEQ ID NO: 6) | DDSDRPS (SEQ ID NO: 7) | QVWDSSSD HWV (SEQ ID NO: 8) |
| | TQVQLVESGGGLVQPGGSLRLSCAASG FTFSSYAMSWVRQAPGKGLEWVSAISG SGGSTYYADSVKGRFTISRDNSKNTLY LQMNSLRAEDTAVYYCATHAAAGDYWG QGTLVTVSS (SEQ ID NO : 1) | | | SYELIQPPSVSVAPGQTARITCGGSNI RSKSVHWYQQKPGQAPVLWYDDSDRP SGIPERFSGSNSGNTATLTISRVEAGD EADYYCQVWDSSSDHWVFGGRTKVTVL (SEQ ID NO: 2) | | |
| F31 | GFTFSSYA MS (SEQ ID NO: 11) | AISGSGGST YYADSVKG (SEQ ID NO: 12) | VAAGDY (SEQ ID NO: 13) | EGNNIGSK GVH (SEQ ID NO: 14) | DGSDRPS (SEQ ID NO: 15) | QVWDNSSD HPNYV (SEQ ID NO: 16) |
| | TQVQLVETGGGLVQPGGSLRLSCAASG FTFSSYAMSWVRQAPGKGLEWVSAISG SGGSTYYADSVKGRFTISRDNSKNTLY LQMNSLRAEDTAVYYCARVAAGDYWGQ GTLVTVSS (SEQ ID NO: 9) | | | SYELTQPPSVSVAPGKTARITCEGNNI GSKGVHWYQQKPGQAPALVVYDGSDRP SGIPERFSGSNSGNTATLTISRVEAGD EADYYCQVWDNSSDHPNYVFGTRTKLT VL (SEQ ID NO: 10) | | |
| TW3 | GFAFSNYA MS (SEQ ID NO: 19) | GISGSGGST YYADSVKG (SEQ ID NO: 20) | EGAFGGR K (SEQ ID NO: 21) | RSSQSLLH SNGYNYVD (SEQ ID NO: 22) | LGSNRAS (SEQ ID NO: 23) | MQGLQDPR TF (SEQ ID NO: 24) |
| | TQVQLVESGGGLVQPGGSLRLSCAASG FAFSNYAMSWVRQAPGKGLEWVSGISG SGGSTYYADSVKGRFTISRDNSKNTLY LQMNSLRAEDTAVYYCAREGAFGGRKG QGTLVTVSS (SEQ ID NO : 17) | | | DIVMTQTPLSLPVTPGEPASISCRSSQ SLLHSNGYNYVDWYLQKPGQPPHLLIY LGSNRASGVPDRFSGSGSGTDFTLKIS RVEAEDVGVYYCMQGLQDPRTFGQGTK VEIK (SEQ ID NO: 18) | | |
| T22 | GYSLSELS MH (SEQ ID NO: 27) | SFDPEDGET TYAQRFQG (SEQ ID NO: 28) | EIWSGYA YFDL (SEQ ID NO: 29) | TLRSGINV GPYRMY (SEQ ID NO: 30) | KSDSDTQ (SEQ ID NO: 31) | MIWHNNAV V (SEQ ID NO: 32) |
| | TQVQLVQSGTEVKKPGASVKVSCKVSG YSLSELSMHWVRQAPGKGLEWMGSFDP EDGETTYAQRFQGRVTMTEDTSTDTAY MELRSLTSDDTAVYYCAREIWSGYAYF DLWGRGTLVTVSS (SEQ ID NO: 25) | | | QPVLTQSSSLSASPGASVSLTCTLRSG INVGPYRMYWYQQKPGSPPQYLLSYKS DSDTQQASGVPSRFSGSKDASANAGIL LISGLQSEDEADYYCMIWHNNAVVFGG GTKLTVL (SEQ ID NO: 26) | | |

A whole cell phage-ELISA was used to demonstrate specific binding of the selected anti-EphA5 scFv antibodies to EphA5 target on a human lung carcinoma cell line in vitro. Single scFv clones were produced as monovalent phage and tested for binding on H460 human lung carcinoma (EphA5 positive) and H226 human lung squamous cell carcinoma (EphA5 negative) cell lines in vitro. Briefly, cells were seeded on 96-well plate, blocked and incubated with phage displaying the scFv of interest at different concentrations. After washing, cell surface bound phage were detected with the antiM13-HRP conjugated mAb (GE).

The results of the binding assay are presented in FIG. 1, and show that all four of the scFv clones specifically bound to EphA5 positive H460 cells.

A whole cell phage-internalization assay was used to characterize the internalization properties of the selected anti-EphA5 scFv antibodies. Single scFv clones were produced as monovalent phage and tested for binding and internalization on H460 human lung carcinoma (EphA5 positive) and H226 human lung squamous cell carcinoma (EphA5 negative) cell lines in vitro. An irrelevant scFv displayed on phage was used as negative control. Briefly, the cells were seeded on microscope slides, blocked and incubated with phage for 4 h to allow binding and internalization. After washing, the surface bound phage were stripped, and the cells were fixed and permeabilized. The phage were detected with a mouse antiM13 mAb (GE) and a Cy3-conjugated antiMouse secondary Ab (Dako). The slides were mounted with VECTASHIELD® anti-fade mounting medium containing DAPI staining for nuclei and visualized by immunofluorescence.

Figure 2:
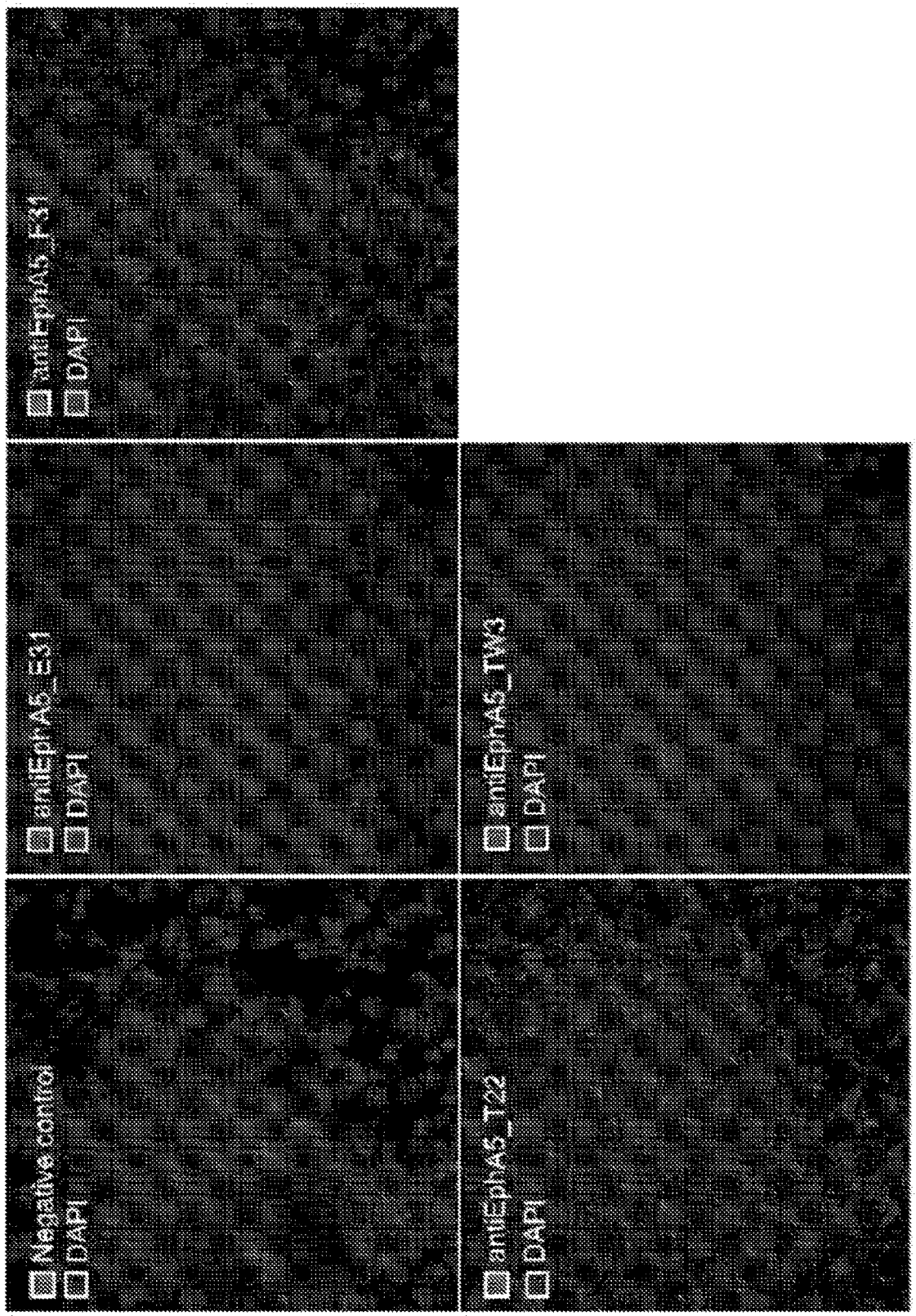
FIG. 2. Immunofluorescence cellular imaging, showing intracellular location of selected anti-EphA5 scFv antibodies in human carcinoma cells. There is moderate staining of E31 and TW3, with stronger staining of F31 and T22.

The results are presented in FIG. 2, which shows the immunofluorescence images of the internalization assay. Two of the tested scFv antibodies (T22 and F31) showed significant internalization properties, with one showing very high levels of internalization (T22).

In order to evaluate the therapeutic effectiveness of anti-EphA5 antibody-drug conjugates (ADCs), the four anti-EphA5 scFv antibodies were expressed as minibodies and utilized in a secondary antibody-drug conjugate cell-based cytotoxic assay. More specifically, minibodies comprising scFv-human Fc fusions were expressed in CHO-S cells (Life Technologies) and tested on the EphA5 positive H460 human lung carcinoma cell line.

Briefly, supernatant containing minibodies at an unknown concentration were added to cells cultured in 96-wells plates. After a 10 minute incubation on ice, secondary antibody-drug conjugates were added to each well at a final concentration of 20 nM. Cell survival was assessed in real time for 72 h with the automated xCELLigence System (ACEA Biosciences). The following secondary antibody-drug conjugates obtained from Moradec LLC, San Diego were evaluated in the cytotoxic assay.
1. Fab-aHFc-CL-MMAF: Fab anti-human IgG Fc-MMAF (monomethyl auristatin F) antibody with cleavable linker.
2. Fab-aHFc-CL-DMDM: Fab anti-human IgG Fc-duocarmycin antibody with cleavable linker.
3. Fab-aHFc-NC-DM1: Fab anti-human IgG Fc-maytansinoid antibody with non-cleavable linker.
4. Fab-aHFc-NC-AAMT: Fab anti-human IgG Fc-amanitin antibody with non-cleavable linker.
5. Fab-aHFc-NC-AAMF: Fab anti-human IgG Fc-AAMF antibody with non-cleavable linker.

Figure 3A:
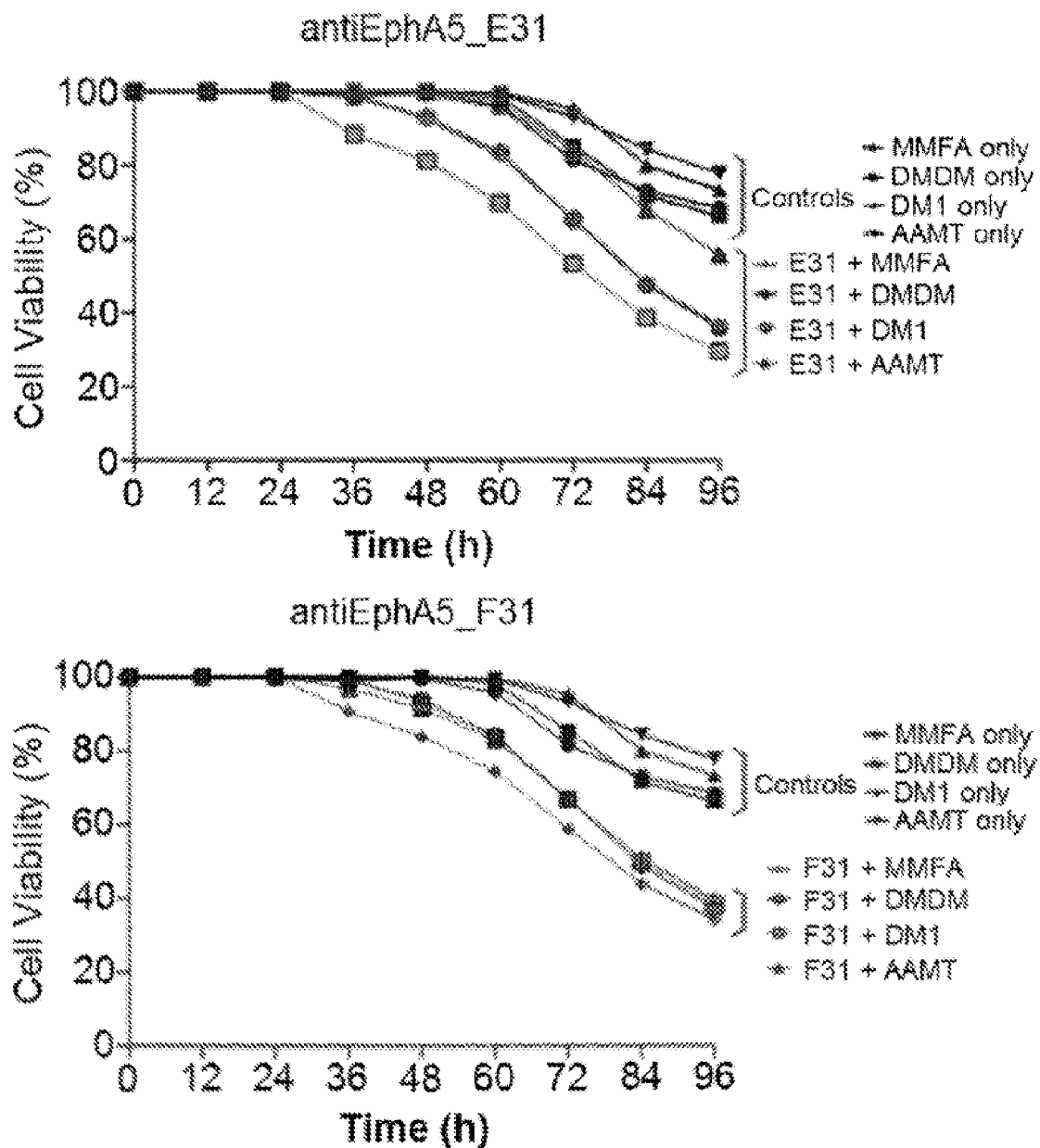
FIGS. 3A-3B. Cell viability assay showing that anti-EphA5 minibody—secondary antibody-drug conjugates are more effective at killing human carcinoma cells compared to drug alone.
Figure 3B:
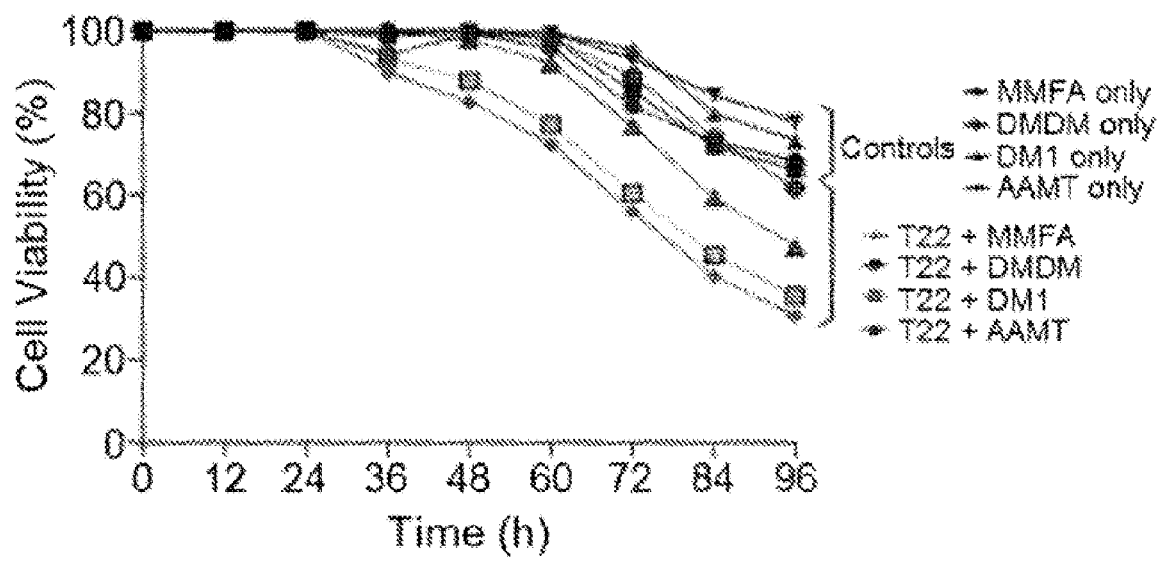
Figure 3B:
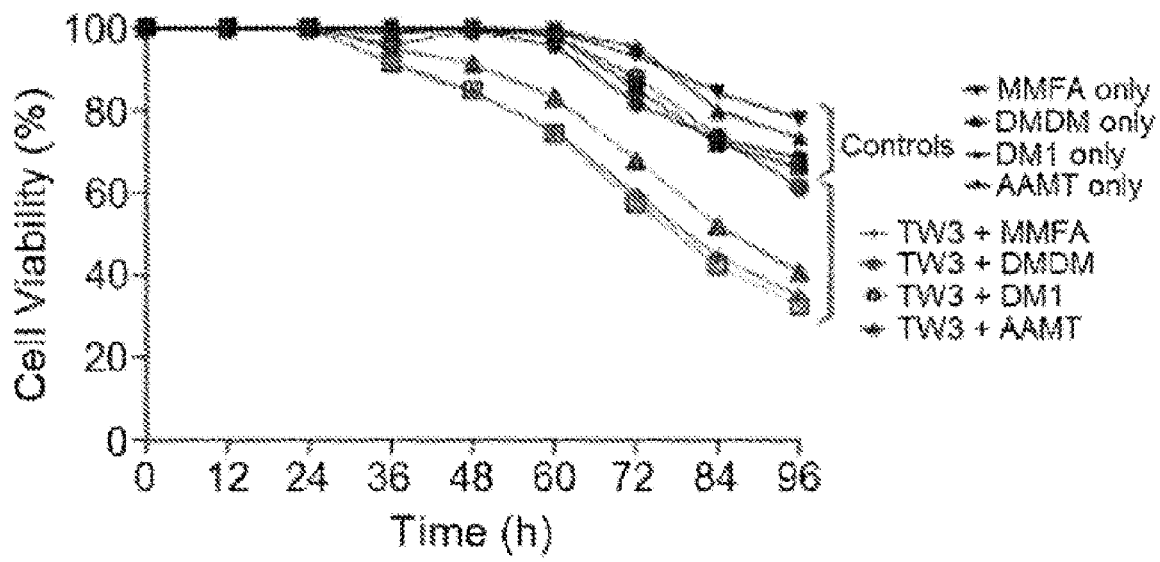
Figure 4A:
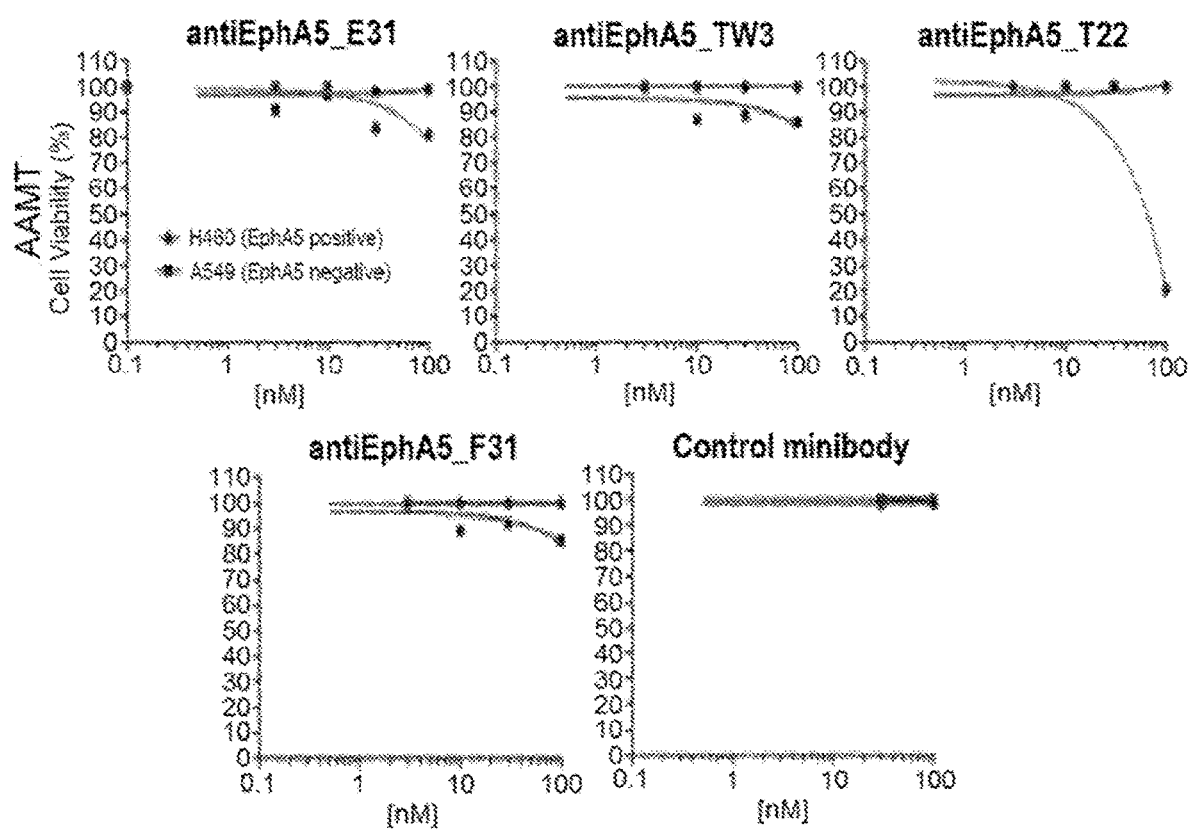
FIGS. 4A-4D. Secondary Antibody-drug conjugate. Protein G purified minibodies were added to cells cultured in 96-wells plates. After a 10 minute incubation on ice, secondary antibody-drug conjugates were added to each well at a final concentration of 20 nM. Cell survival was assessed in real time for 72 h with the automated xCELLigence System (ACEA Biosciences).
Figure 4B:
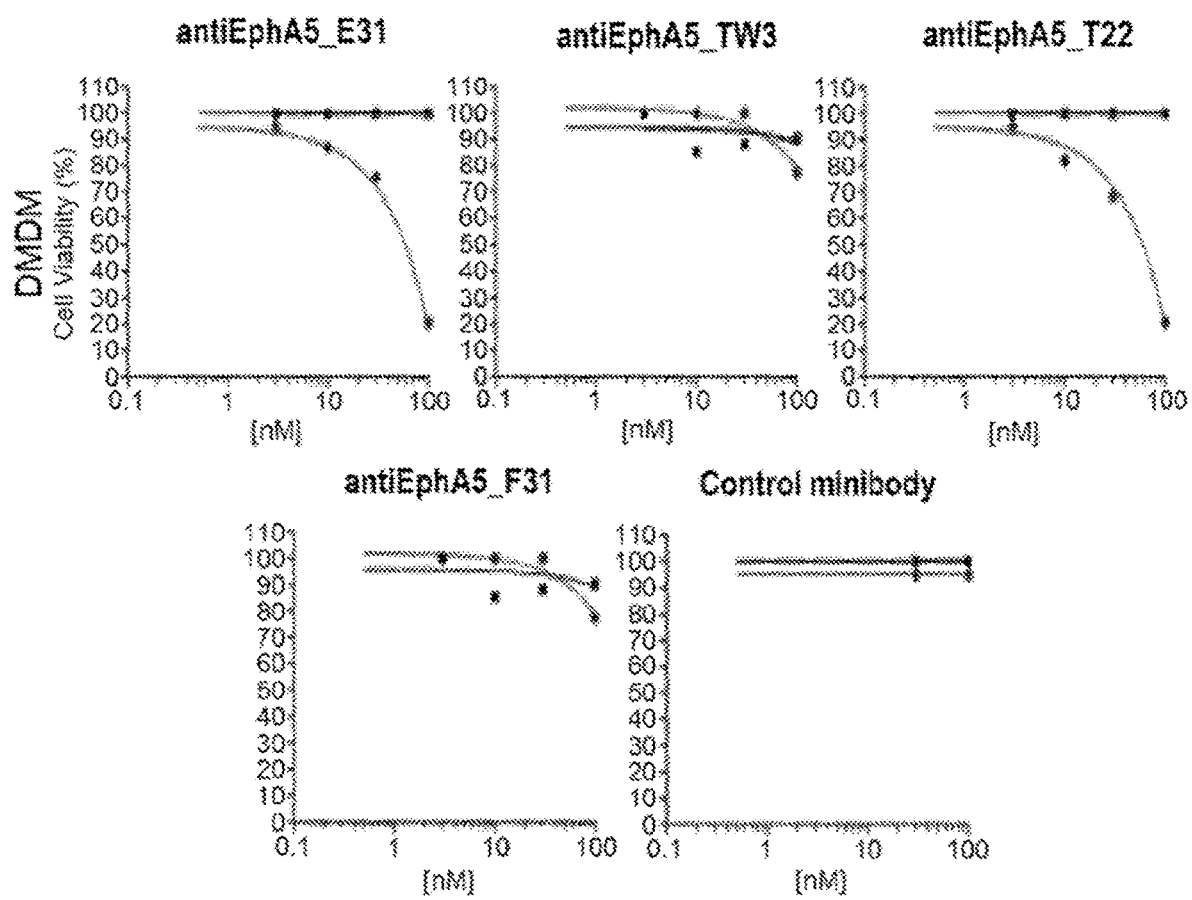
Figure 4C:
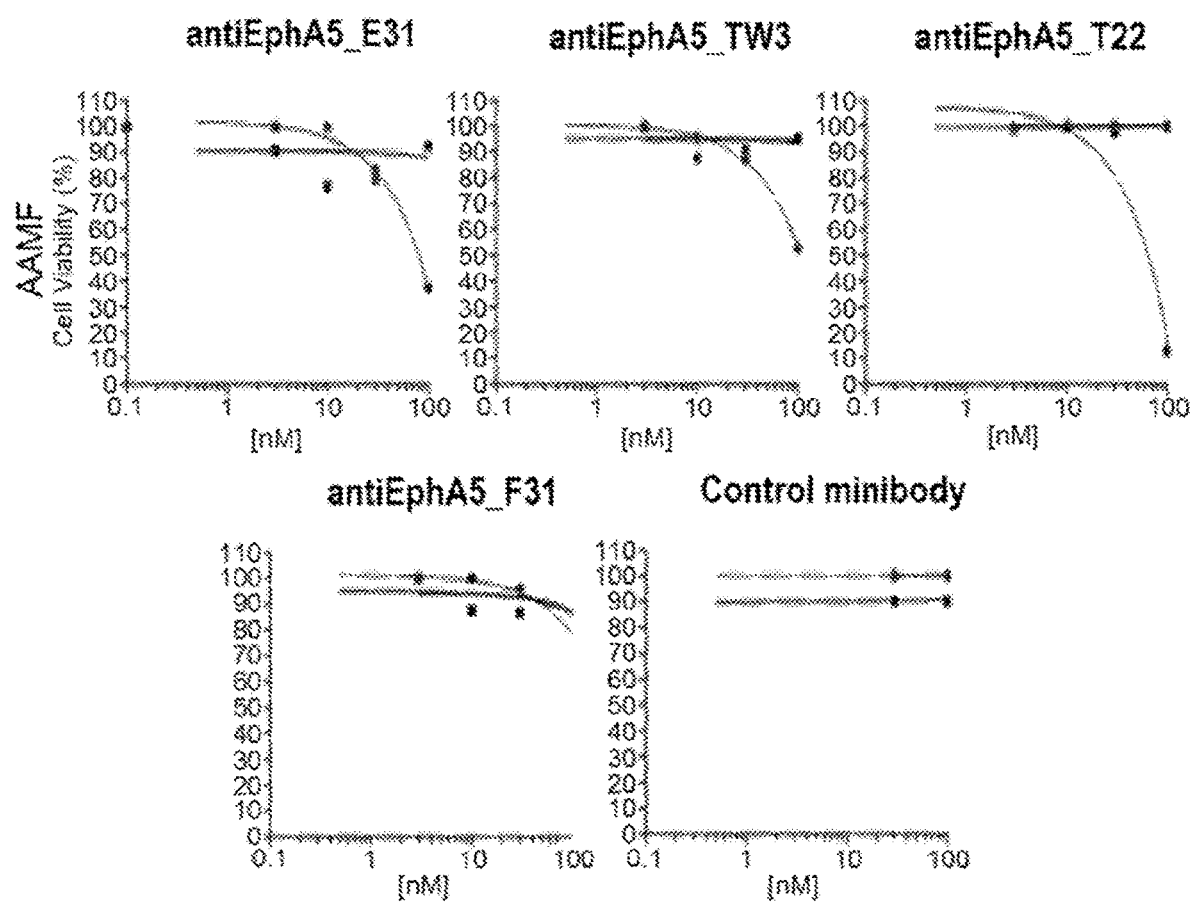
Figure 4D:
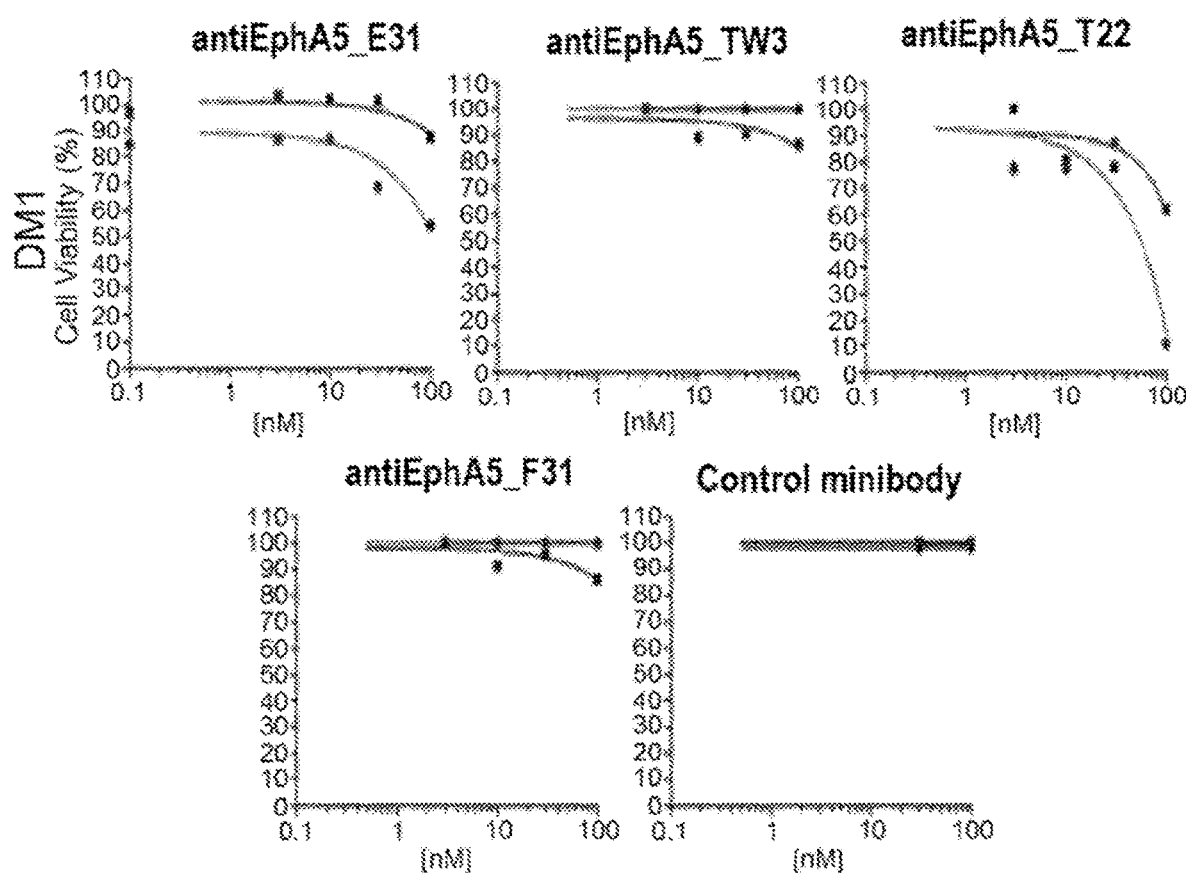

The results are reported in FIGS. 3A-3B, wherein cell viability was plotted over time in presence of the minibody in combination with the secondary ADC or in presence of the secondary ADC alone, and in FIG. 4, wherein cell viability was plotted over concentration. For all minibodies, an enhanced cell killing effect was observed when compared to the secondary drug conjugates alone. A generally better performance was observed when the minibodies were used with the DM1 maytansinoid secondary conjugate, a cytotoxic small molecule which inhibits cell division by blocking the polymerization of tubulin.

Figure 5:
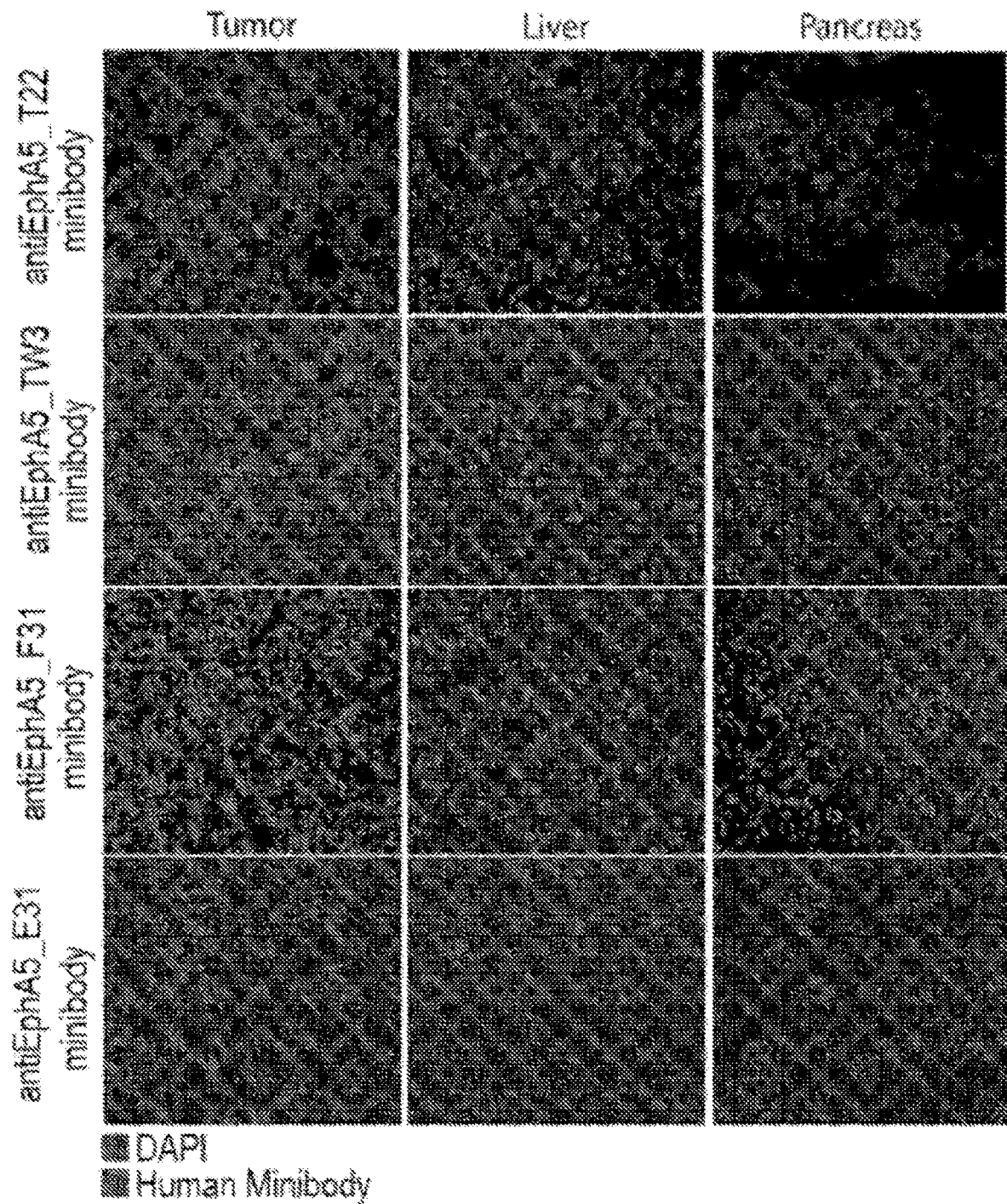
FIG. 5. Tumor targeting of minibodies. Protein G purified minibodies were injected into mice bearing tumors and allowed to circulate for 6 min. After perfusion with PBS and with PFA, tumor tissue and controls were harvested, embedded and sectioned. Minibody detection in tumor and selected control tissues (liver and pancreas) is shown.
Figure 6A:
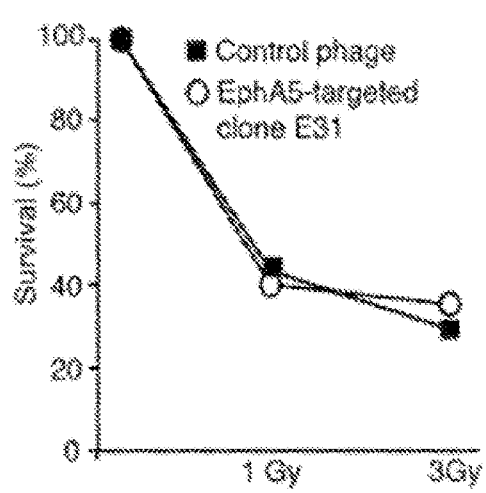
FIGS. 6A-6D. Radiosensitization activity of anti-EphA5 clones. Surviving fractions of H460 cells exposed to increasing doses of IR after administration of phage displaying selected anti-EphA5 scFvs. A phage library was used as control. Two out of four tested clones (B and D) showed radiosensitizing properties.
Figure 6B:
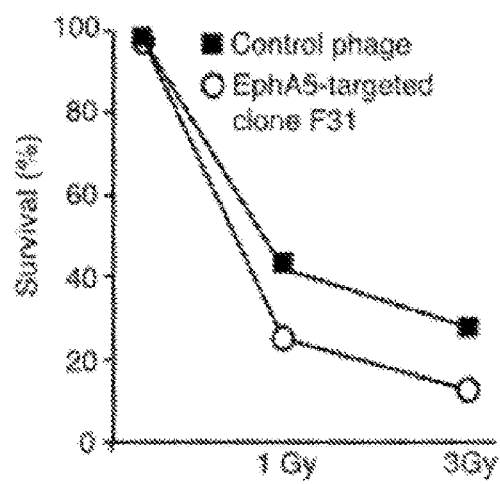
Figure 6C:
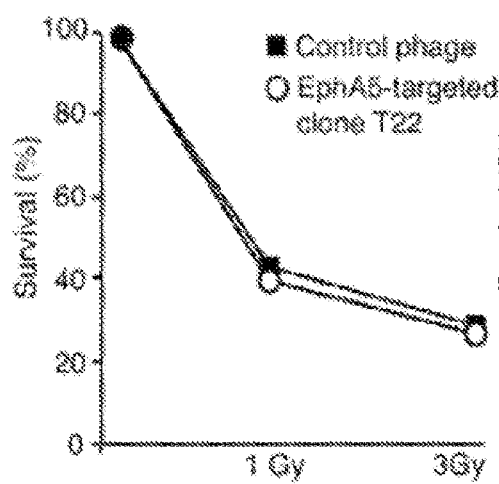
Figure 6D:
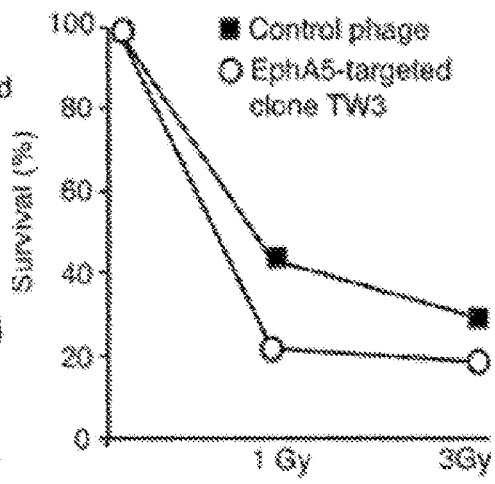

Tumor targeting properties of the minibodies was also analyzed. Protein G purified minibodies were injected into mice bearing tumors and allowed to circulate for 6 min. After perfusion with PBS and with PFA, tumor tissue and controls were harvested, embedded and sectioned. Minibody detection in tumor and selected control tissues (liver and pancreas) is shown in FIG. 5.

Additionally, the radiosensitization activity of anti-EphA5 clones was studied. Surviving fractions of H460 cells exposed to increasing doses of IR after administration of phage displaying selected anti-EphA5 scFvs. A phage library was used as control. Results are shown in FIGS. 6A-6D. Two out of the four tested clones (F31 (FIG. 6B) and TW3 (FIG. 6D) showed radiosensitizing properties.

Example 2 — Generation of Anti-GRP78 Specific scFv Antibodies

In vitro scFv antibody selection: Recombinant human GRP78 antigen (Abcam) was biotinylated (EZ-Link™ Sulfo-NHS-LC-LC-Biotin, Life Technologies), according to the manufacturer instructions. Biotinylated GRP78 antigen was used for the in vitro phage and yeast display selections. Briefly, the scFv naive library cloned into the pDNA5 vector was expressed on phage particles. Approximately $10^{12}$ phage particles were incubated with streptavidin-coated magnetic beads (Dynabeads, Life Technologies) saturated with the biotinylated antigen, and 2 rounds of selection were performed. The selected scFv population was subcloned into the pDNL6 yeast vector and transformed into yeast.

After induction of the yeast culture, the scFvs were displayed on the yeast cell surface. The cells were incubated with the biotinylated antigen at 100 nM concentration and the cells displaying the higher affinity binders were sorted by flow cytometry. After the 2nd round, 10,000 antigen-binding yeast cells were sorted and the corresponding displayed scFv genes were amplified from the pDNL6 vector by PCR. The selected scFv genes were cloned back into the phagemid pDAN5 vector and displayed on multivalent phage particles (3-5 copies of the scFv were displayed per particle).

In vivo scFv antibody selection: The anti-GRP78 scFv phage population ($10^{11}$ phage particles from the in vitro pre-selected multivalent phage population) was injected intravenously in 3 Balb/c mice bearing EF43.fgf4 murine breast cancer derived xenograft tumors. After 3h from the injection, the mice were sacrificed and the tumor and control tissues were harvested. The tumor homing phage rescued from the tumor tissue of the 3 mice were amplified and mixed in equimolar amounts. The in vivo selection was reiterated for 2 additional cycles. At the end of the $3^{rd}$ cycle, the scFv genes were amplified by PCR from the pDAN5 plasmid DNA extracted from the tissue and prepared for next generation sequencing (NGS). MiSeq (Illumina) paired-end sequencing, combined with a bioinformatic analysis based on the in house developed AbMining Toolbox software were used to identify the unique $V_H$ domains of the tumor homing scFv genes.

Identification of scFv gene candidates and rescue: The AbMining Toolbox software analysis relies on the recognition of the HCDR3 sequence of each scFv gene, a signature element in all antibodies. The sequenced tumor homing clones were identified based on their HCDR3 and ranked according to their relative abundance in the tissue. The most abundant clones identified in each round of in vivo selection were chosen as candidates for further characterization. Once identified, the clones of interest were rescued from the selection output by means of an inverse PCR-based strategy (D'Angelo et al., 2014, mAbs 6(1): 160-172). Briefly, 2 back-to-back primers were designed on the scFv-specific HCDR3 DNA sequence and used for an inverse PCR using the pDAN5 plasmid DNA extracted from the tumor tissue harvested after each selection round. The amplicon obtained are collections of selected HCDR3-specific scFv genes in the context of the phagemid vector pDAN5. After DNA purification, the amplicons were ligated and transformed into bacteria. Upon sequencing confirmation, the clones were produced as mono- or multi-valent phage or as Ig-like minibodies (Di Niro et al., 2007, *BMC Biotechnology* 7:46) into CHO-S cells for further characterization.

Various anti-GRP78 scFv clones were further characterized. Three of the most abundant scFv clones identified were sequenced to determine their full length amino acid sequences, presented below. The VL and VH domains are listed below in Table 1, along with the CDRs.

```
antiGRP78_B4 scFv amino acid sequence
                                  (SEQ ID NO: 61)
SYVLTQPPSVSVAPGKTATITCGGDDIGSKSVHWYQQKPG

QAPVLVVYDDGDRPSGIPERFSGSNSGNTATLAISRVEAG

DEADYYCQVWDSSSDQYVFGSGTKLTVLSGGSTITSYNVY

YTKLSSSGTQVRLQESGPGLVKPSQTLSLTCTVSGGSISS

GGYYWSWIRQHPGKGLEWIGYIYYSGSTYYNPSLESRVTI

SVDTSKNQFSLKLSSVTAADTAVYYCARYSSIDAFEIWGQ

GTMVTVSS antiGRP78_D1 scFv amino acid sequence
                                  (SEQ ID NO: 62)
SYELIQPPSVSVAPGQTARIACGGNNIGSKSVHWYQQKPG

QAPVLVVYDDSDRPSGIPERFSGSNSGNTATLTISRVEAG

DEADYYCQVWDSSSDHPGVFGTGTKLTVLSGGSTITSYNV

YYTKLSSSGTQVQLQQSGPGLVEPSQTLSLTCAISGDSVS

SNSAAWNWIRQSPSRGLEWLGRTYYRSRWYNDYAVSVESR
```

-continued
ITINPDTSKNQFSLQLNSVTPEDTAVYYCARDPYYYDSSG

YYYFDAFGIWGQGTMVTVSS antiGRP78_F6 scFv amino acid sequence
                                    (SEQ ID NO: 63)
SYELTQPHSVSVAPGQTARITCGGDNIGSKSVHWYQQRPG

QAPVLVVYDDSDRPSGIPERFSGSNSENTATLTISGVEAG

DEADYYCQVWDSTSHHVVFGGGTKLTVLSGGSTITSYNVY

YTKLSSSGTQVQLQQSGPGLVKPPQTLSLTCAISGDSVSS

NSAAWNWIRQPSPSRGLEWLGRTYYRSKWYNDYAVSVKSRI

TINPDTSKNQFSLQLNSVTPEDTAVYYCARDPYYYDSSGY

Figure 7:
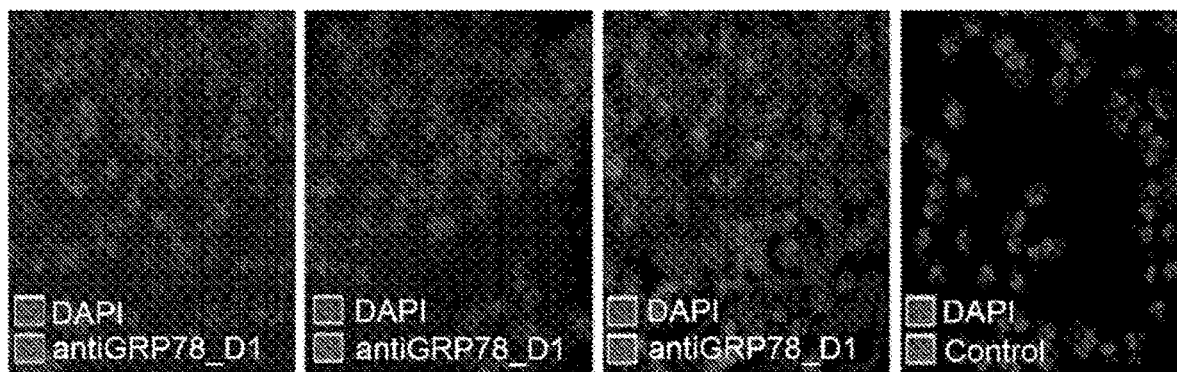
FIG. 7. Phage internalization. Single scFv clones were produced as monovalent phage and tested for binding and internalization on MCF-7 human breast cancer (GRP78 positive) cell line in vitro. An irrelevant scFv displayed on phage was used as negative control. Briefly, the cells were seeded on microscope slides, blocked and incubated with phage for 4 h to allow binding and internalization. After washing, the surface bound phage were stripped, and the cells were fixed and permeabilized. The phage were detected with a mouse antiM13 mAb (GE) and a Cy3-conjugated antiMouse secondary Ab (Dako). The slides were mounted with VECTASHIELD® anti-fade mounting medium.

YYFDAFDIWGQGTMVTVSS with VECTASHIELD® anti-fade mounting medium. The results are presented in FIG. 7, which shows the immunofluorescence images of the internalization assay. Internalized phage is shown are red dots inside the cells. Nuclei are stained in blue.

Figure 8:
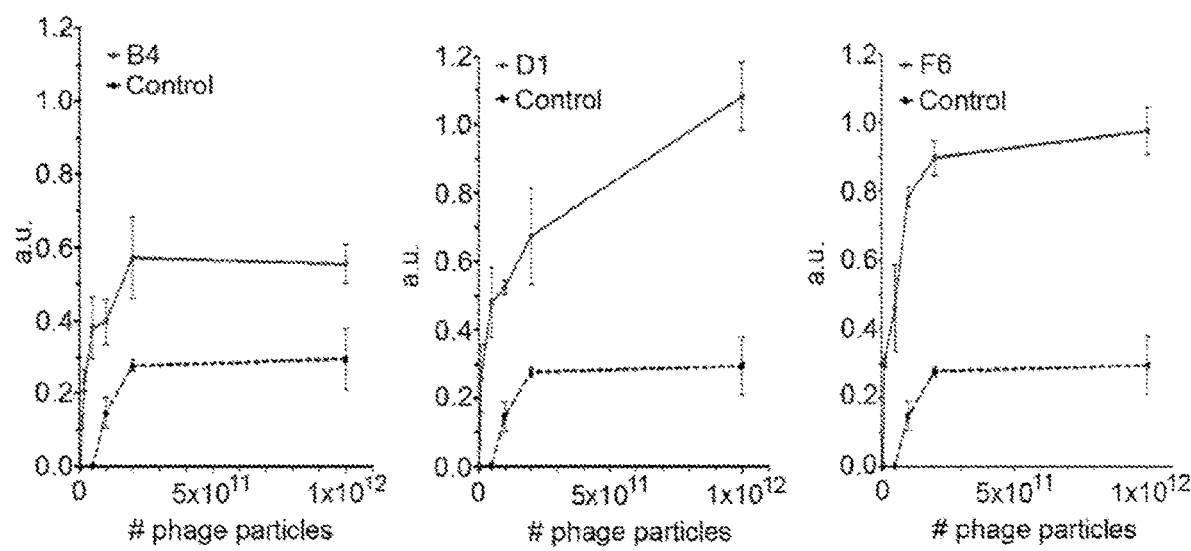
FIG. 8. Phage binding on cells. A whole cell phage-ELISA was used to demonstrate specific binding of the selected anti-GRP78 scFv antibodies to GRP78 target on a human breast carcinoma cell line in vitro. Single scFv clones were produced as monovalent phage and tested for binding on MCF-7 in vitro. Briefly, cells were seeded on 96-well plate, blocked and incubated with phage displaying the scFv of interest at different concentrations. After washing, cell surface bound phage were detected with the antiM13-HRP conjugated mAb (GE). An irrelevant scFv displayed on phage was used as negative control.

A whole cell phage-ELISA was used to demonstrate specific binding of the selected anti-GRP78 scFv antibodies to GRP78 target on a human breast carcinoma cell line in vitro. Single scFv clones were produced as monovalent phage and tested for binding on MCF-7 in vitro. Briefly, cells were seeded on 96-well plate, blocked and incubated with phage displaying the scFv of interest at different concentrations. After washing, cell surface bound phage were detected with the antiM13-HRP conjugated mAb (GE). An irrelevant scFv displayed on phage was used as negative control. The results are shown in FIG. 8. Anti-GRP78 phage bind specifically to cells expressing surface GRP78. Negative control shows background binding.

TABLE 1A

Amino acid sequences and CDRs of scFv clones.

| | Heavy Chain Sequence | | | Light Chain Sequence | | |
|---|---|---|---|---|---|---|
| | CDR1 | CDR2 | CDR3 | CDR1 | CDR2 | CDR3 |
| | Amino acid sequence | | | Amino acid sequence | | |
| B4 | GGSISSGGYY (SEQ ID NO: 39) | YIYYSGSTYYNPSLES (SEQ ID NO: 40) | RYSSIDAFEI (SEQ ID NO: 41) | GGDDIGSKSVH (SEQ ID NO: 42) | DDGDRPS (SEQ ID NO: 43) | QVWDSSSDQYV (SEQ ID NO: 44) |
| | QVRLQESGPGLVKPSQTLSLTCTVSGGSISSGGYYWSWIRQHPGKGLEWIGYIYYSGSTYYNPSLESRVTISVDTSKNQFSLKLSSVTAADTAVYYCARYSSIDAFEIWGQGTMVTVSS (SEQ ID NO: 37) | | | SYVLTQPPSVSVAPGKTATITCGGDDIGSKSVHWYQQKPGQAPVLVVYDDGDRPSGIPERFSGSNSGNTATLAISRVEAGDEADYYCQVWDSSSDQYVFGSGTKLTVL (SEQ ID NO: 38) | | |
| D1 | GDSVSSNSAA (SEQ ID NO: 47) | RTYYRSRWYNDYAVSVES (SEQ ID NO: 48) | DPYYYDSGYYYFDAFGI (SEQ ID NO: 49) | GGNNIGSKSVH (SEQ ID NO: 50) | DDSDRPS (SEQ ID NO: 15) | QVWDSSSDHPGV (SEQ ID NO: 51) |
| | QVQLQQSGPGLVEPSQTLSLTCAISGDSVSSNSAAWNWIRQPSPSRGLEWLGRTYYRSRWYNDYAVSVESRITINPDTSKNQFSLQLNSVTPEDTAVYYCARDPYYYDSGYYYFDAFGIWGQGTMVTVSS (SEQ ID NO: 45) | | | SYELIQPPSVSVAPGQTARIACGGNNIGSKSVHWYQQKPGQAPVLVVYDDSDRPSGIPERFSGSNSGNTATLTISRVEAGDEADYYCQVWDSSSDHPGVFGTGTKLTVL (SEQ ID NO: 46) | | |
| F6 | GDSVSSNSAA (SEQ ID NO: 55) | RTYYRSKWYNDYAVSVKS (SEQ ID NO: 56) | DPYYYDSGYYYFDAFDI (SEQ ID NO: 57) | GGDNIGSKSVH (SEQ ID NO: 58) | DDSDRPS (SEQ ID NO: 59) | QVWDSTSHHVV (SEQ ID NO: 60) |
| | QVQLQQSGPGLVKPPQTLSLTCAISGDSVSSNSAAWNWIRQPSPSRGLEWLGRTYYRSKWYNDYAVSVKSRITINPDTSKNQFSLQLNSVTPEDTAVYYCARDPYYYDSGYYYFDAFDIWGQGTMVTVSS (SEQ ID NO: 53) | | | SYELTQPHSVSVAPGQTARITCGGDNIGSKSVHWYQQRPGQAPVLVVYDDSDRPSGIPERFSGSNSENTATLTISGVEAGDEADYYCQVWDSTSHHVVFGGGTKLTVL (SEQ ID NO: 54) | | |

Figure 9:
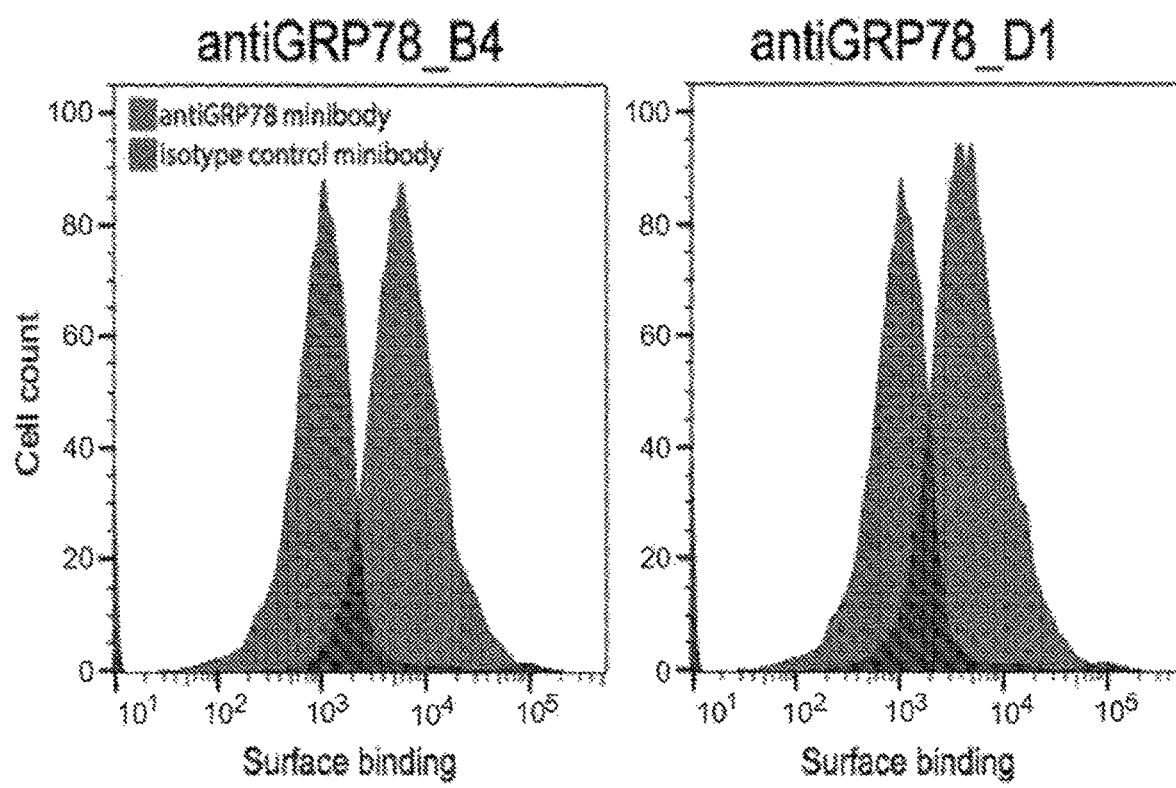
FIG. 9. Cell surface binding. Cell surface binding of anti-GRP78 minibodies was assessed by flow cytometry on Ef43 murine breast cancer cell line. Briefly, Ef43 cells were harvested and incubated for 30 min with the fluorescently labeled minibodies (antiGRP78, right peak in both panels, and isotype control). After extensive washings, the cells were analyzed by flow cytometry.
Figure 10A:
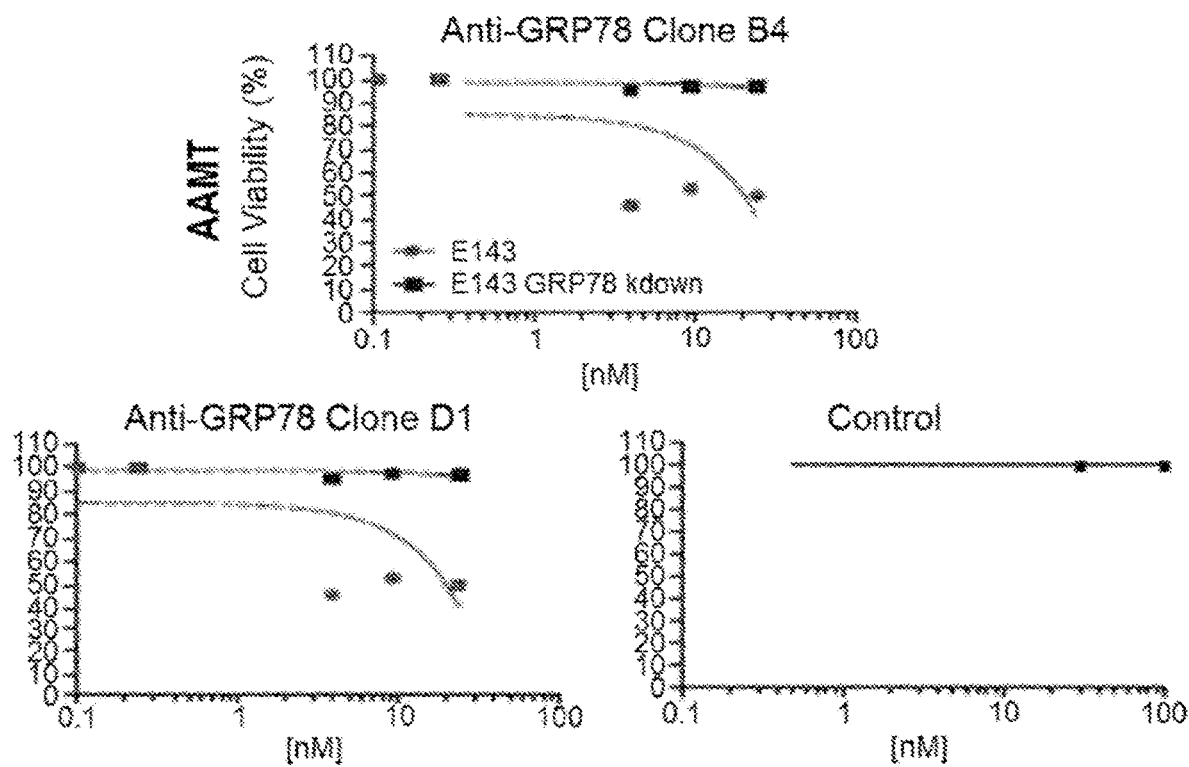
FIGS. 10A-10D. Secondary Antibody-drug conjugate. Protein G purified minibodies were added to cells cultured in 96-wells plates. After a 10 minute incubation on ice, secondary antibody-drug conjugates were added to each well at a final concentration of 20 nM. Cell survival was assessed in real time for 72 h with the automated xCELLigence System (ACEA Biosciences).
Figure 10B:
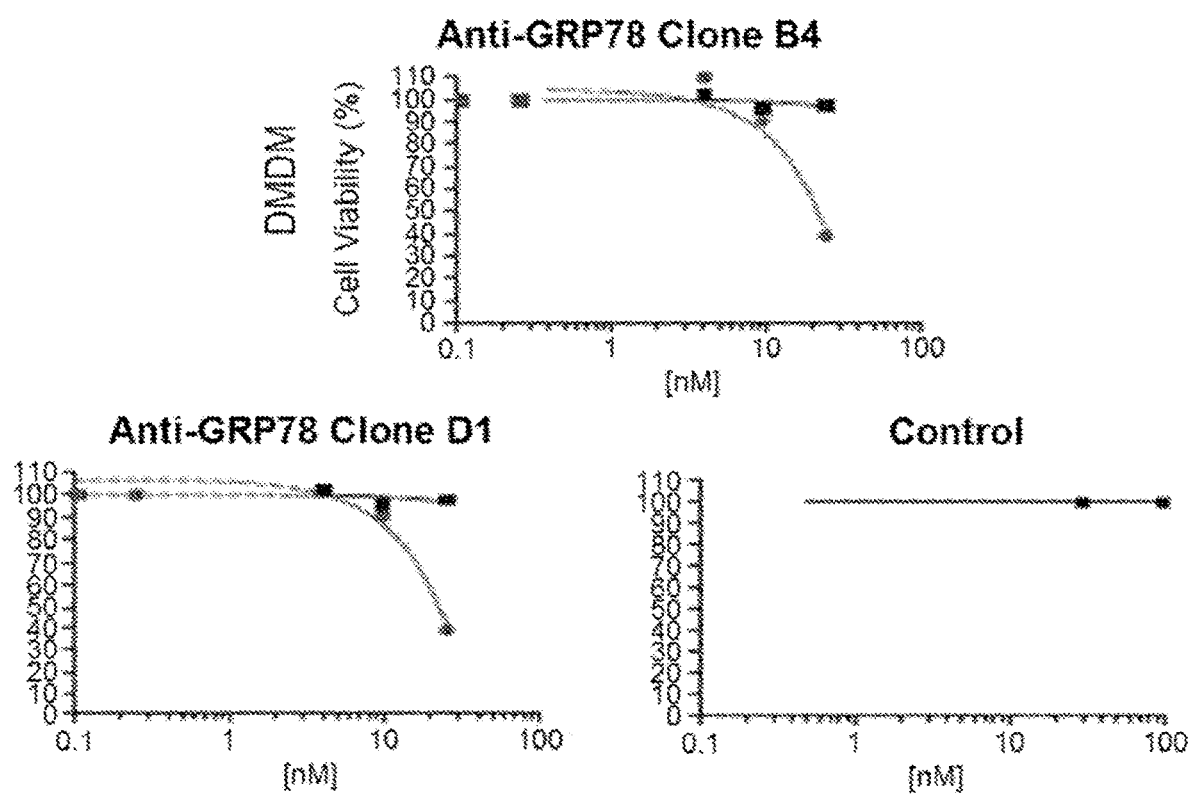
Figure 10C:
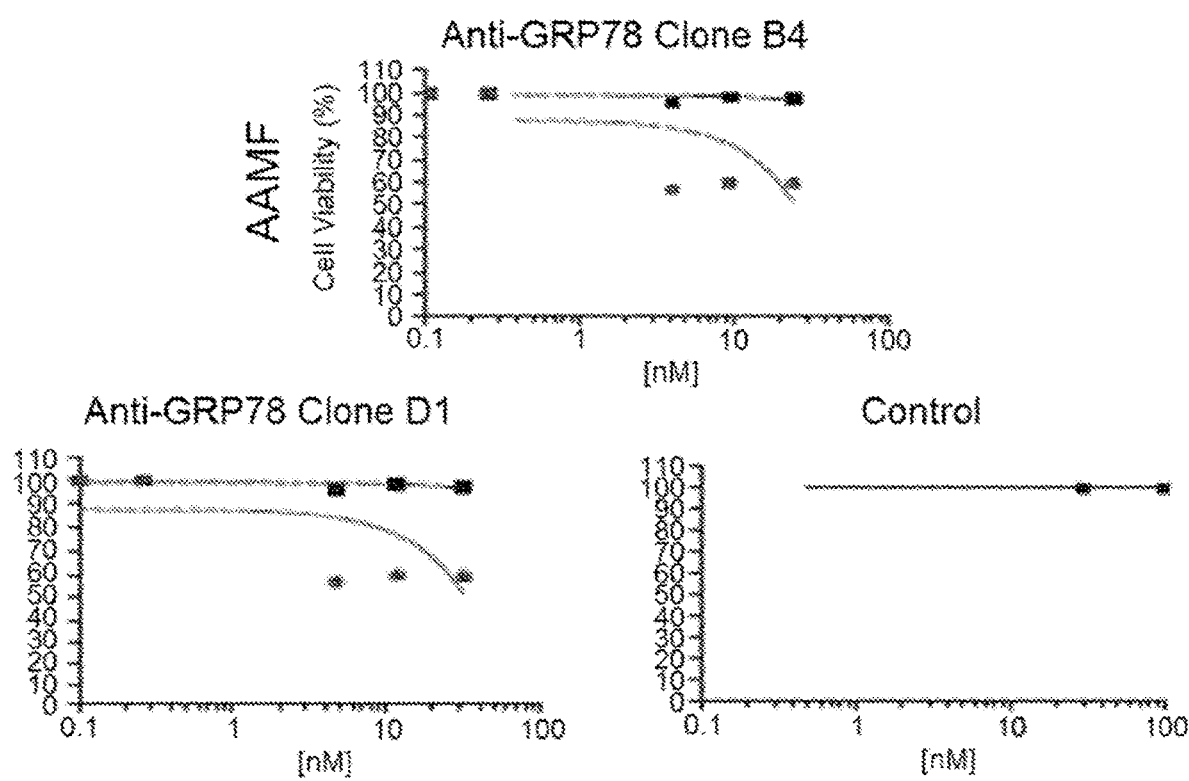
Figure 10D:
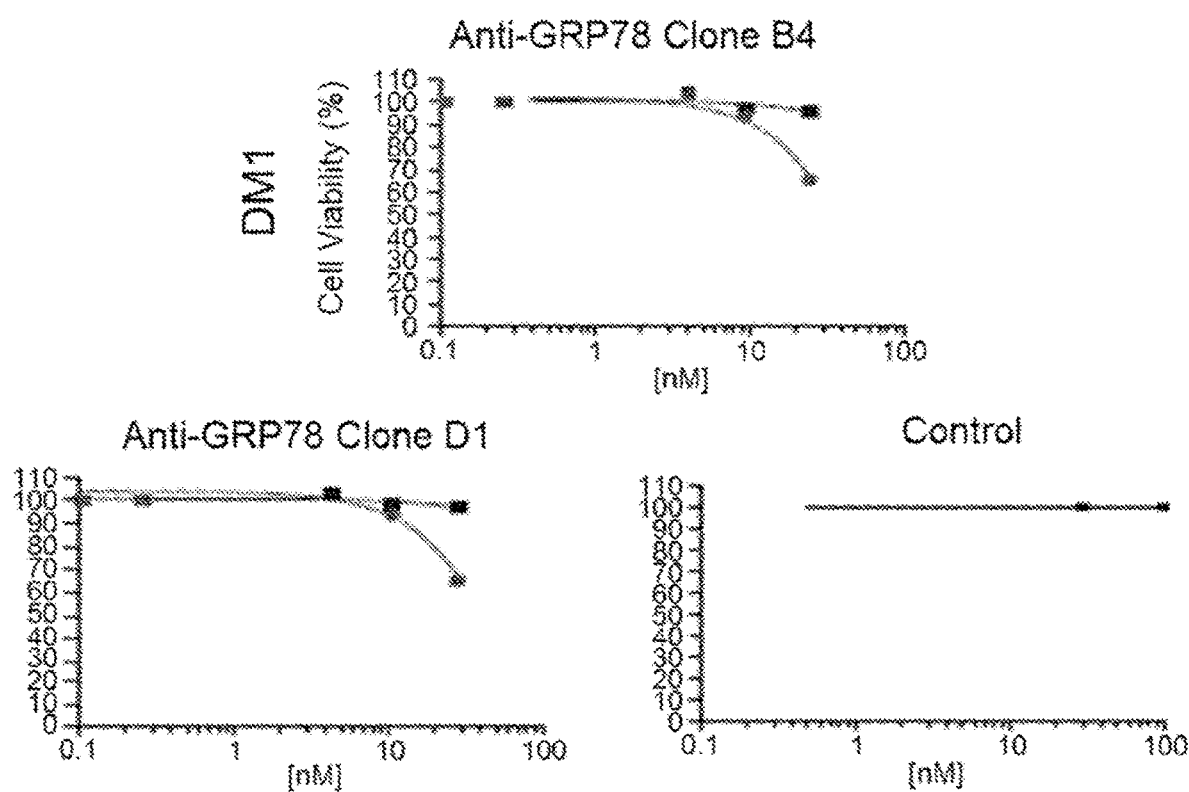
Figure 11:
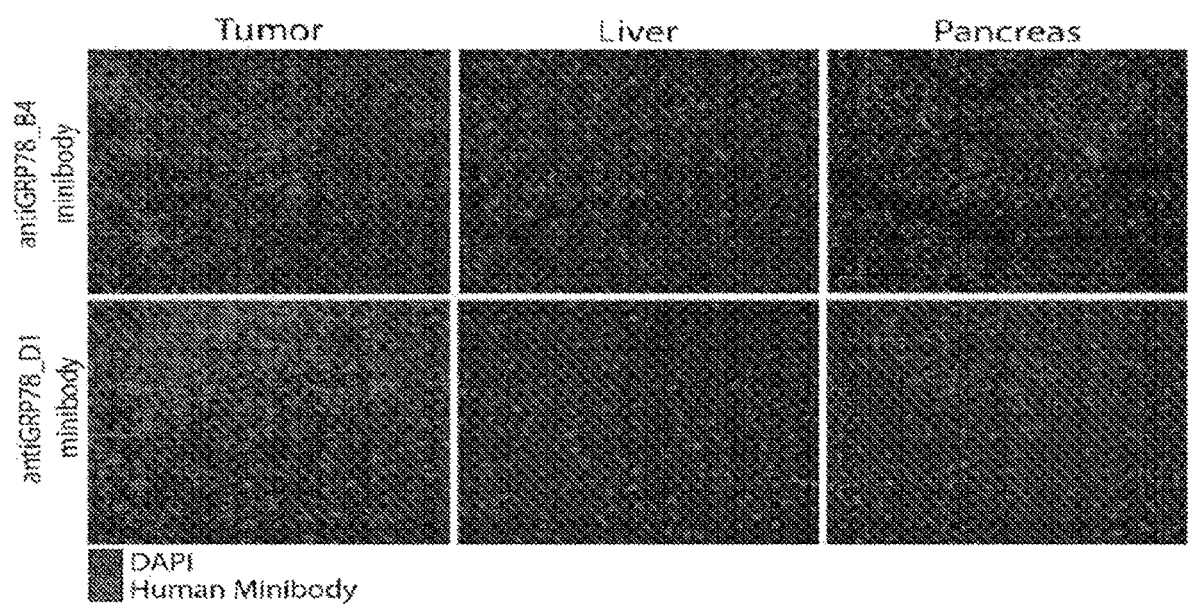
FIG. 11. Tumor targeting of minibodies. Protein G purified minibodies were injected into mice bearing tumors and allowed to circulate for 6 min. After perfusion with PBS and with PFA, tumor tissue and controls were harvested, embedded and sectioned. Minibody detection in tumor and selected control tissues (liver and pancreas) is shown.

A whole cell phage-internalization assay was used to characterize the internalization properties of the selected anti-GRP78 scFv antibodies. Single scFv clones were produced as monovalent phage and tested for binding and internalization on MCF-7 human breast cancer (GRP78 positive) cell line in vitro. An irrelevant scFv displayed on phage was used as negative control. Briefly, the cells were seeded on microscope slides, blocked and incubated with phage for 4h to allow binding and internalization. After washing, the surface bound phage were stripped, and the cells were fixed and permeabilized. The phage were detected with a mouse antiM13 mAb (GE) and a Cy3-conjugated antiMouse secondary Ab (Dako). The slides were mounted Cell surface binding of anti-GRP78 minibodies was assessed by flow cytometry on Ef43 murine breast cancer cell line. Briefly, Ef43 cells were harvested and incubated for 30 min with the fluorescently labeled minibodies (anti-GRP78 and isotype control). After extensive washings, the cells were analyzed by flow cytometry. The results are shown in FIG. 9. Anti-GRP78 minibodies bind to the surface of breast cancer cells.

In order to evaluate the therapeutic effectiveness of anti-GRP78 antibody-drug conjugates (ADCs), the anti-GRP78 scFv antibodies were expressed as minibodies and utilized in a secondary antibody-drug conjugate cell-based cytotoxic assay. Briefly, protein G purified minibodies were added to cells cultured in 96-wells plates. After a 10 minute incubation on ice, secondary antibody-drug conjugates were added to each well at a final concentration of 20 nM. Cell survival was assessed in real time for 72 h with the automated xCELLigence System (ACEA Biosciences). The results are shown in FIGS. 10A-10D. Cell killing occurs in the presence of B4 and D1 minibodies and the drugs AAMT (Alfa-amanitin) and (duocarmycin DM).

Tumor targeting properties of the minibodies was also analyzed. Protein G purified minibodies were injected into mice bearing tumors and allowed to circulate for 6 min. After perfusion with PBS and with PFA, tumor tissue and controls were harvested, embedded and sectioned. Minibody detection in tumor and selected control tissues (liver and pancreas) is shown in FIG. 8. Minibodies target tumors specifically. Liver and pancreas were used a control organs and showed minimal staining.

Example 3- SPARTA Methodology

Experimental Procedures

Animals

Female wild-type Balb/c and female Balb/c Nu/Nu mice (Harlan Laboratories) were housed in the animal facility at the University of New Mexico Comprehensive Cancer Center (UNMCCC). All animal procedures were formally reviewed and approved by the Institutional Animal Care and Use Committee (IACUC) at the UNMCCC. Cell Culture NCI-H460, A549 and NCI-H226 human lung cancer-derived cell lines were purchased from the American Type Culture Collection (ATCC) and maintained in Dulbecco's Modified Eagle's Medium (DMEM) containing 10% fetal bovine serum (FBS) plus 1% penicillin G/streptomycin SO4. Human MCF7 breast cancer-derived cells were purchased from ATCC and maintained in Eagle's Medium, supplemented with 0.01 mg/mL human recombinant insulin and 10% FBS. Mouse mammary Ef43.fgf4 cells were maintained in DMEM supplemented with 10% FBS, 5 ng/ml mouse epithelial growth factor (EGF), 1 µg/ml bovine insulin plus 1% penicillin G/streptomycin SO4. SUM190PT human inflammatory breast cancer cells were maintained in Ham F12 medium, supplemented with 5% FBS, 5 µg/mL insulin, 1 µg/mL hydrocortisone, 10 mM HEPES, and 1% penicillin G/streptomycin SO4. CHO-S cells were purchased from Life Technologies and maintained in serum-free FreeStyle™ CHO Expression Medium. Ef43.fgf4 GRP78-knockdown cells were obtained by lentivirus infection, stably transfected and maintained in selection media containing antibiotics. The QUANTUM™ SIMPLY CELLULAR® Microspheres (Bangs Laboratories) were used to quantitate the number of targeted molecules on the surface of cells.

Phage-And Yeast-Display Antibody Screening In Vitro scFv antibody clones were isolated by integrating phage- and yeast-display methodologies as described (Ferrara et al., 2015). Briefly, a naïve human phage antibody library (Sblattero and Bradbury, 2000) was used in two rounds of screening in vitro either on recombinant human EphA5 (R&D Systems) or GRP78 (Abcam). The binding pools of scFv clones were subcloned into a yeast display vector as described (Ferrara et al., 2012), and the yeast mini-libraries were further enriched for target-specific binders applying two rounds of sorting by using standard flow cytometry protocols (FACSAria, Becton Dickinson) as described (Boder and Wittrup, 1998).

Experimental Tumor Xenograft And Isogenic Models

Tumor targeting properties of the minibodies was also analyzed. Protein G puri Mouse mammary Ef43.fgf4 isogenic tumor cells and SUM19OPT human inflammatory breast cancer cells were collected at 70% confluency and administered subcutaneously (s.c.) in the mammary fat pad of either immunocompetent female Balb/c mice (Ef43.fgf4), or female Balb/c nude mice (SUM190PT) as indicated. SUM190PT cells were administered s.c. in 1:1 (vol/vol) with Matrigel™ (Corning) as described (Dobroff et al., 2016). NCI-H460 human lung cancer cells were administered s.c. in the right flanks of Balb/c female nude mice. After approximately 10 d, tumors reached —200-300 mm$^3$ and were separated into size-matched tumor-bearing mouse cohorts for experimentation.

Phage-Display In Vivo

In vivo phage selections were performed as described (Kolonin et al., 2006; Pasqualini and Ruoslahti, 1996; Rajotte et al., 1998; Staquicini et al., 2011b). Animals received $10^{10}$ phage particles i.v. and tumors and negative control organs were collected after 3 h of systemic circulation. Tumor-homing phage were retrieved by PCR amplification, and full-length scFv products (~800 bp) were re-cloned to produce multivalent functional phage particles for subsequent rounds of selection. Phage quantification was performed by quantitative phage PCR (Dias-Neto et al., 2009) and host bacterial infection as described (Kolonin et al., 2006; Rajotte et al., 1998; Staquicini et al., 2011a; Staquicini et al., 2011b).

Phage Binding Assays And Enzyme-Linked Immunosorbent Assay (ELISA)

Serial dilutions of individual phage particles in phosphate-buffered saline (PBS) containing 2% non-fat milk were placed in microtiter wells previously coated with 0.5 µg of either EphA5 or GRP78, as indicated. After extensive washes, remaining bound phage particles were detected with an anti-M13 peroxidase-conjugated mouse monoclonal antibody (GE-Amersham Biosciences).

Phage binding to the surface of cells was tested by whole-cell ELISA. Briefly, exponentially growing cells were fixed in 96-well microtitration plates (Nunc) at $3 \times 10^5$ cells/well and exposed to serial dilutions of either targeted or control phage particles for 2 h at room temperature (RT). Wells were extensively washed with PBS containing 0.1% TWEEN-20 (polysorbate 20), and bound particles were detected with an anti-M13 peroxidase-conjugated mouse monoclonal antibody. A non-targeted helper phage (termed M13KO7 (Ferrara et al., 2012)) and unrelated scFv served as negative controls, as indicated.

Cell Internalization Assay

Cell internalization assays were performed as described (Arap et al., 2004). In brief, cells plated in eight-chamber slides were blocked with DMEM containing 2% FBS for 1 h at RT, and incubated with $10^9$ TU of phage. After 2 h of incubation at 37° C., cell membrane-bound phage were removed by washes with 20 mM glycine (pH 2.3), and fixed with PBS containing 4% paraformaldehyde (PFA). Fixed cells were permeabilized with PBS containing 0.1% TRITON X-100 (octoxinol), blocked with PBS containing 1% bovine serum albumin (BSA), and incubated with a mouse anti-M13 phage monoclonal antibody for 1 h at RT. After incubation with a rabbit anti-mouse IgG Cy3-conjugated secondary antibody (Jackson Immunoresearch), cells were washed with PBS, and re-fixed in PBS containing 4% PFA. Internalized phage particles were visualized with a standard fluorescence microscope (Nikon Ti-E Inverted Microscope, Nikon).

NGS And Data Analysis

Sample preparation for NGS was performed as described (D'Angelo et al., 2014a). Briefly, plasmid DNA recovered from the selection outputs was amplified with a specific set of primers designed for the MiSeq paired-end sequencing of the scFv VH domains. The amplicons were sequenced with the MiSeqV2 kit for 500 cycles. Sequencing results were analyzed with the aid of the AbMining toolbox software package with default settings for quality filtering (D'Angelo et al., 2014a; D'Angelo et al., 2014b). The identified HCDR3s were clustered at Hamming distance 1 and analyzed further in MS Excel (D'Angelo et al., 2014a; D'Angelo et al., 2014b).

Scfv-Fc Production

Monoclonal scFv antibody genes were subcloned either into the pHygro vector for scFv-Fc expression in CHO cells, or into the yeast expression vector pDNL9 for expression into YVH10 S. cerevisiae yeast cells as indicated (Ferrara et al., 2012), both containing a human Fc sequence (Ferrara et al., 2015). All cloning steps were monitored and verified by DNA restriction enzyme digestion analysis and sequencing. scFv-Fc fusions were purified from the culture supernatant by affinity purification on Protein-G agarose (Roche). ELISA with the corresponding target was performed to test binding specifity of individually purified scFv-Fc.

In Vivo Scfv-Fc Targeting

Tumor homing was assessed by i.v. administration of the scFv-Fc pool into tumor-bearing mice. Two doses of a 2.5 µM solution (100 and 200 µL) were administered i.v. into the tail vein of anesthesized tumor-bearing mice. The scFv-Fcs were allowed to circulate for 6 min, prior to full-body cardiac perfusion with PBS. Immunofluorescence staining was performed on tissue sections with a Cy3-conjugated goat anti-human Fcγ IgG (Jackson Immunoresearch) and DAPI for nuclei staining. Images were acquired with an Nikon Ti-E Inverted fluorescence microscope.

In Vitro Cytotoxicity Assays

Cell killing activity was measured in real-time with the Xcelligence system (ACEA Biosciences). Freshly split tumor cells (25,000 cells/well) were cultured overnight (ON) in a 96-well electronic microtiter plate (E-PLATE® 96) (ACEA Biosciences) in 100 µL of complete culture medium. After 24 h, increasing concentrations of the primary monoclonal scFv-Fcs were added to each microwell followed by addition of 20 nM of secondary ADC reagents (Moradec LLC) linked to monomethyl auristatin F (MMAF) (Fab-αHFc-CL-MMAF), duocarmycin (DMDM) (Fab-αHFc-CL-DMDM), emtansine (DM1) (Fab-aHFc-NC-DM1), or amanitin (AAMT) (Fab-aHFc-NC-AAMT). Cell index was measured every 30 min for 96 h. Controls included primary scFv-Fc alone, drug-conjugated secondary alone, and non-treated cells as indicated.

RESULTS

Figure 12A:
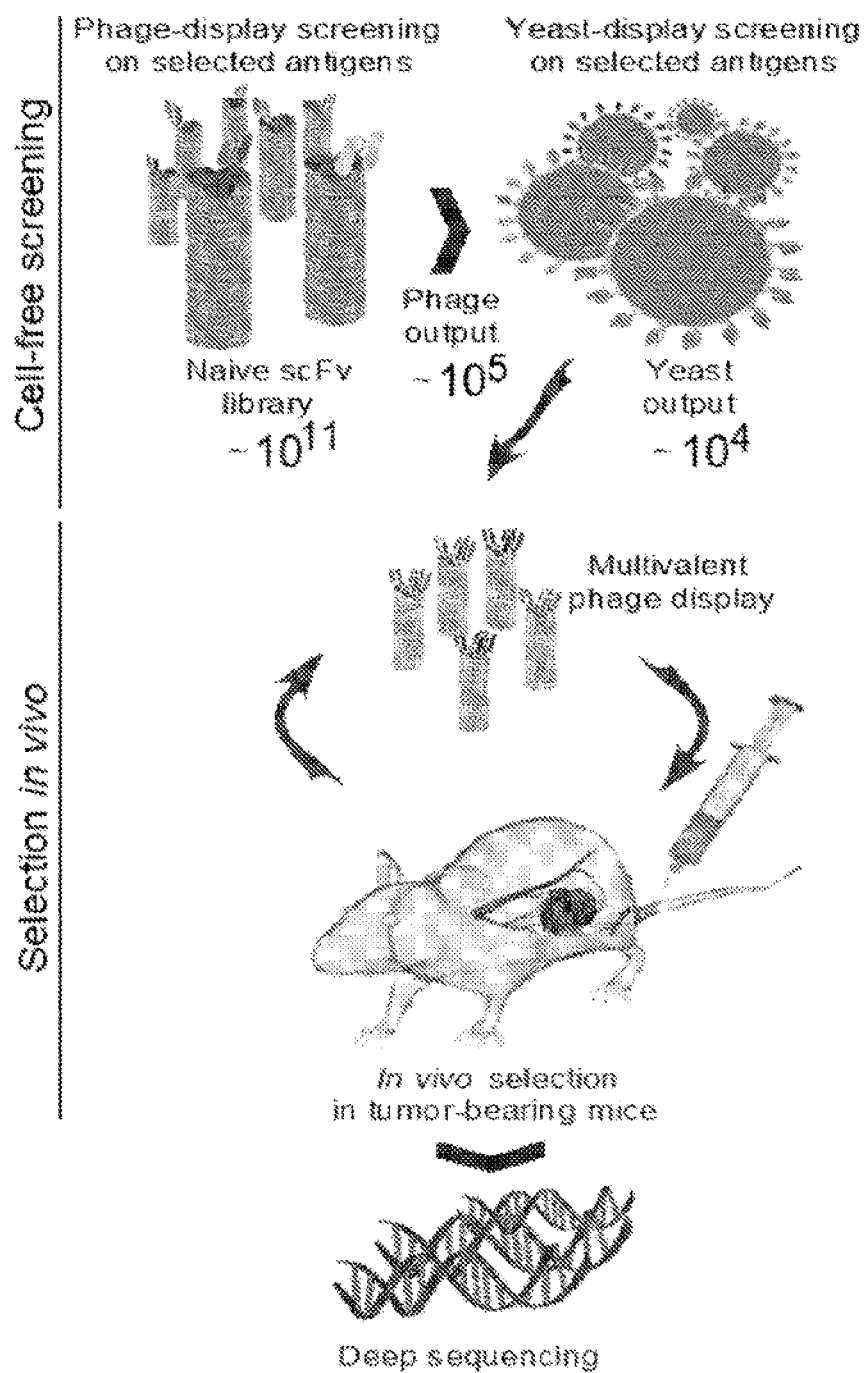
FIGS. 12A-12E. SPARTA Methodology.
Figure 12B:
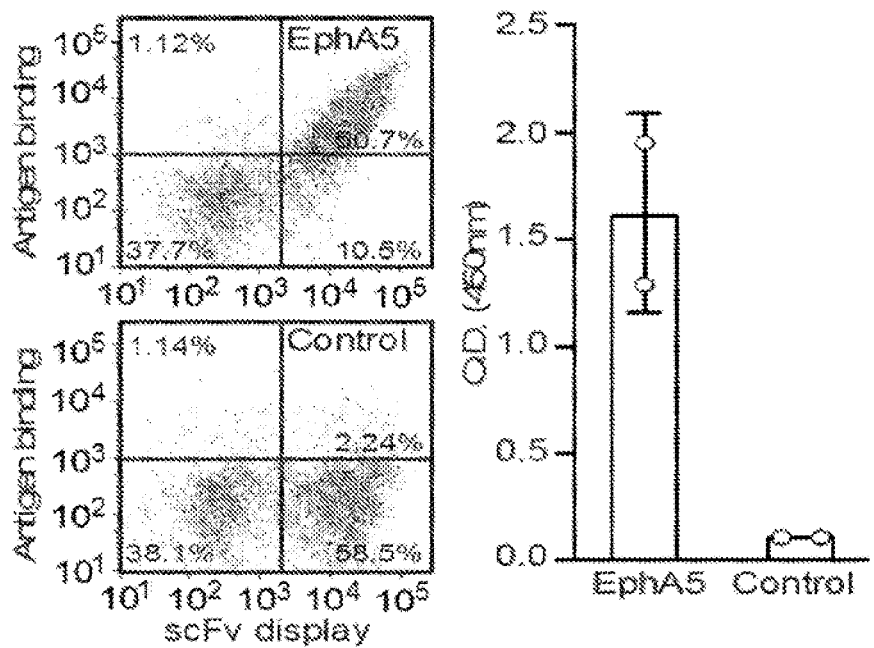
Figure 12C:
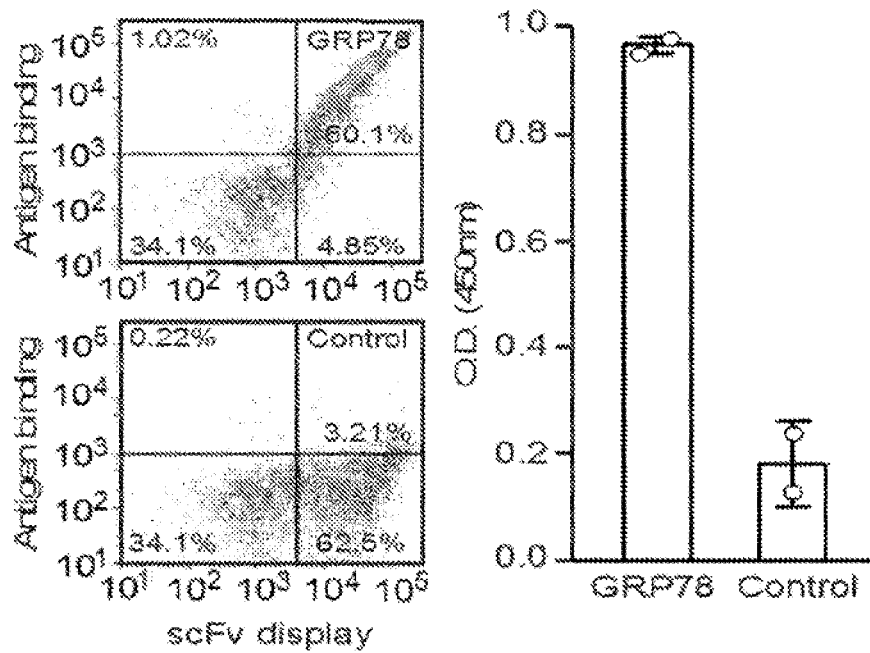
Figure 16:
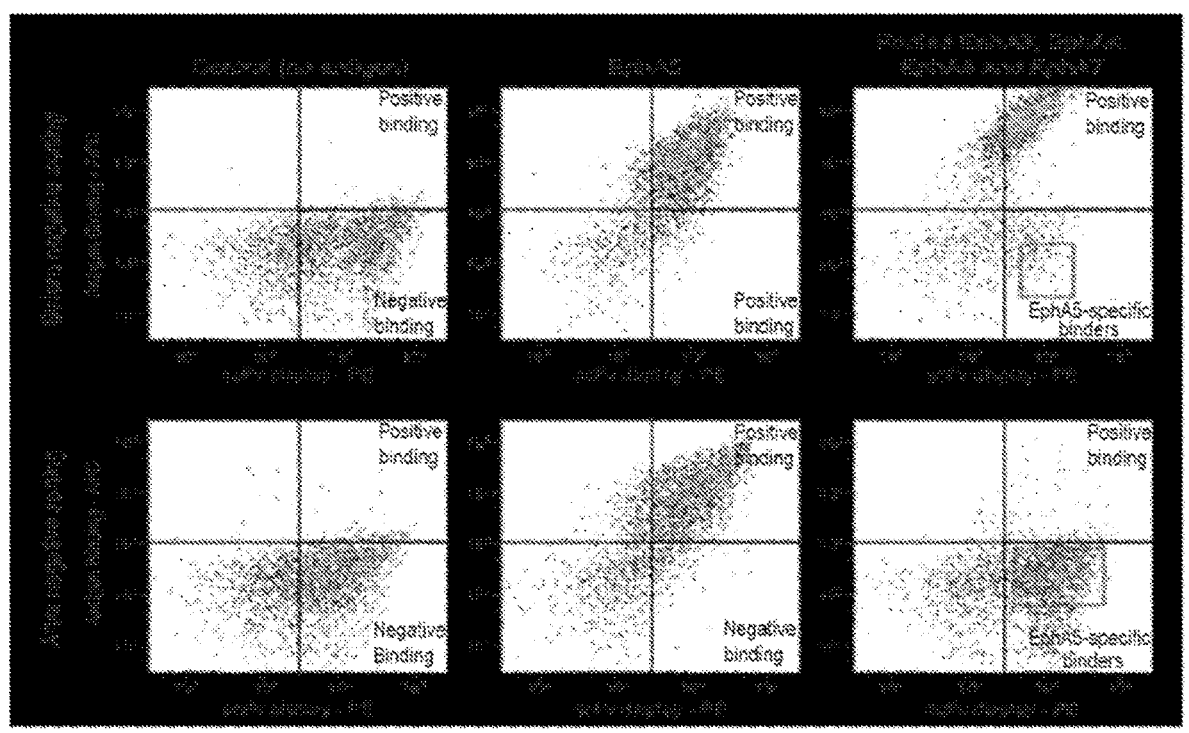
FIG. 16. Negative Selection of a Polyclonal Pool of Anti-Epha5 Antibodies against the Family Member Proteins EphA3, EphA4, EphA6 And EphA7 Clones that showed no binding to the pooled EphA family proteins were enriched by flow cytometry sorting. The resulting population revealed an antibody pool highly specific to EphA5, and not other family members.

Serial In Vitro Screening and In Vivo Selection for the Discovery of Human Recombinant Monoclonal Antibodies A schematic representation of SPARTA is depicted in FIGS. 12A-12C. We first carried out an in vitro unbiased library screening against immobilized human recombinant EphA5 and GRP78 from a large human naïve phage-displayed single chain variable fragment (scFv) library (Sblattero and Bradbury, 2000). After two rounds of library screening in vitro, diversity was reduced five orders of magnitude (from ~1011 unique scFv sequences to <10$^6$). The total phage pool output was subsequently cloned into a yeast-display system. This maneuver allows precise fluorescence activated cell sorting to restrict reactivity to those clones recognizing the target (Ferrara et al., 2015). After two additional rounds of yeast cell sorting, a diverse highly enriched antibody population was obtained for each target (FIGS. 12B and 12C). Antibody clones bound specifically to the corresponding antigens, in both yeast- and phage-display contexts (FIGS. 12B and 12C). The anti-EphA5 antibody pools were negatively selected to minimize or eliminate anti-EphA5 antibodies that would also recognize orthologous ephrin-family members (namely EphA3, 4, 6, and 7) (FIG. 16). Next-generation sequencing (NGS) plus AbMining Toolbox analysis (D'Angelo et al., 2014a) confirmed highly diverse antibody populations, as assessed by the sizable number of individual heavy chain complementarity-determining region 3 (HCDR3) variants obtained for EphA5 (n=207) and GRP78 (n=125). The relatively high polyclonality observed underscores the power of the combined phage/yeast display approach to select diverse specific antibodies.

Figure 12D:
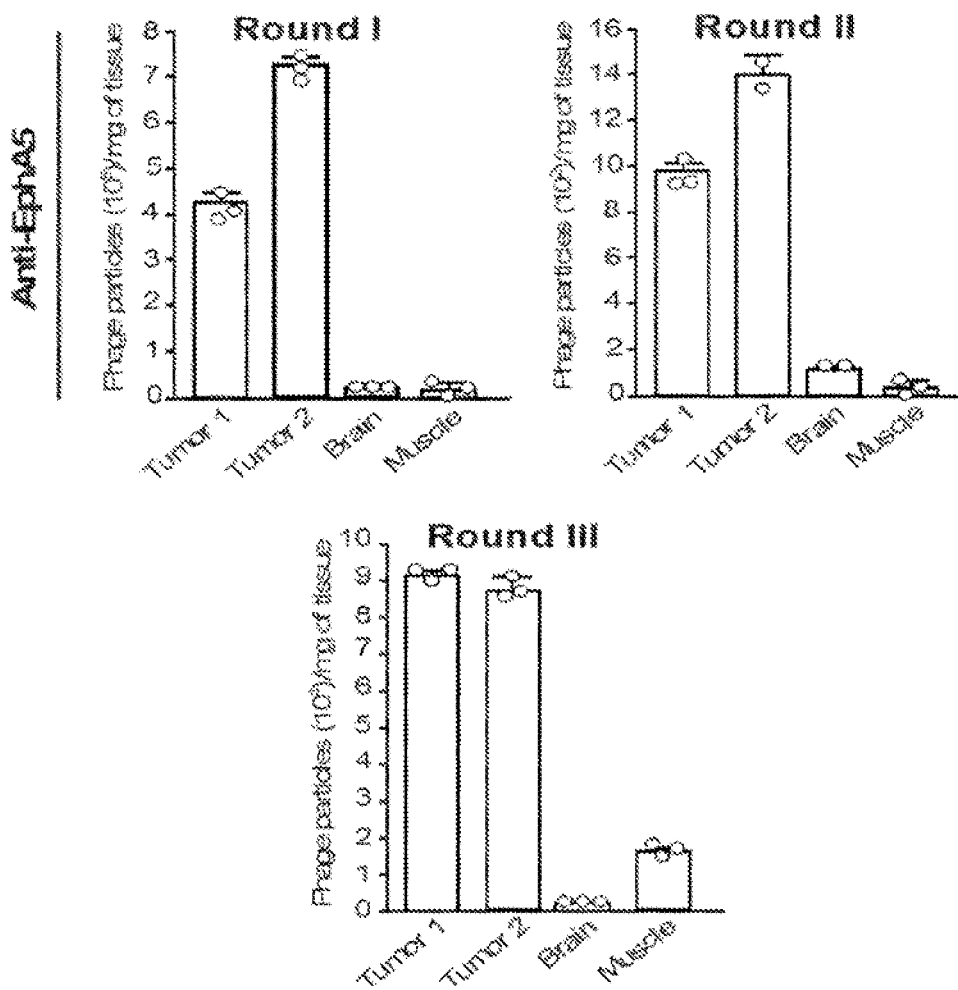
Figure 12E:
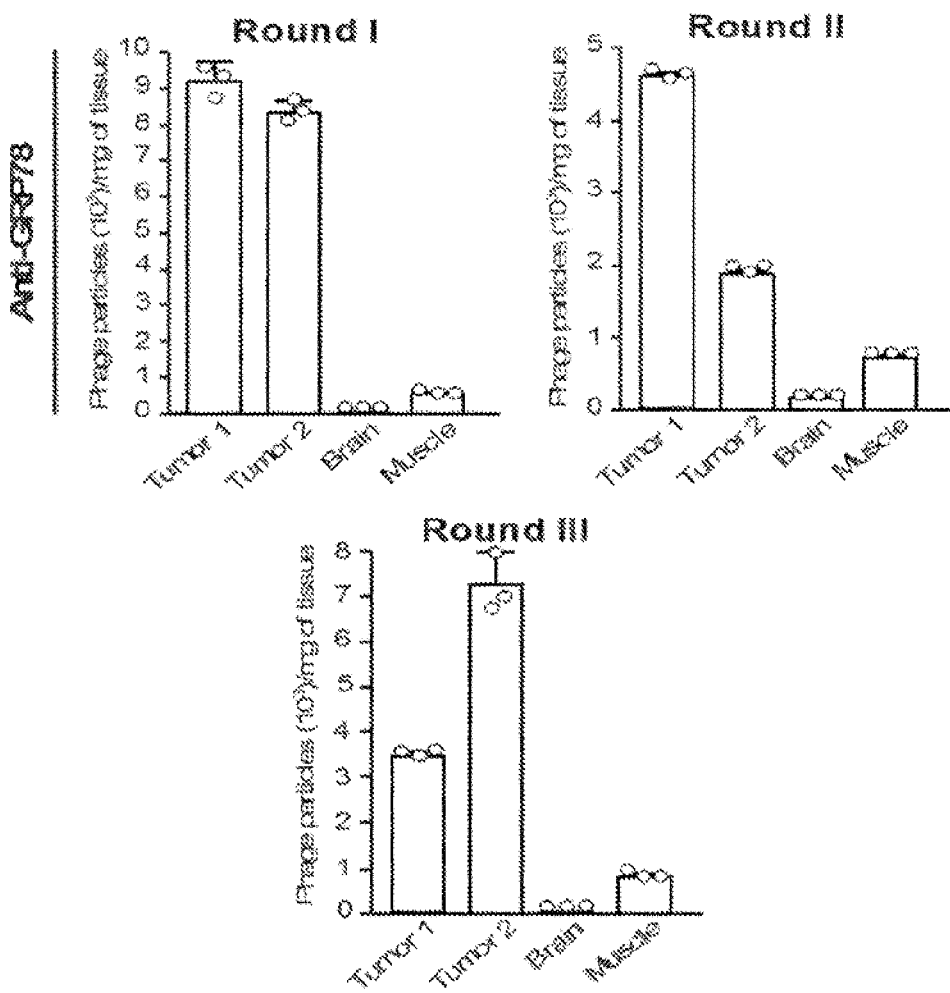

Based on the current understanding of the importance of multivalency in in vivo peptide phage-display originally developed by our group (Arap et al., 2002; Arap et al., 1998; Barnhart et al., 2011; Christianson et al., 2007; Dias-Neto et al., 2009; Hajitou et al., 2006; Kolonin et al., 2001; Kolonin et al., 2004; Kolonin et al., 2006; Ozawa et al., 2008; Pasqualini and Arap, 2002; Pasqualini and Ruoslahti, 1996; Rajotte et al., 1998; Staquicini et al., 2011a; Staquicini et al., 2011b), we generated multivalent antibody phage displaying anti-EphA5 and anti-GRP78 scFv populations using a helper plasmid technology (Chasteen et al., 2006). As opposed to traditional helper phage-mediated monovalent antibody display, helper plasmids provide all the required viral packaging functions but without helper phage contamination in a multivalent form, thereby reducing background binding during in vivo selections, and increasing specific binding of targeted phage through improved avidity (Chasteen et al., 2006). While it has proved somewhat challenging to use helper plasmids with large naïve antibody libraries, applications to peptide libraries and small targeted antibody libraries by contrast have been much more successful (Phipps et al., 2016). The recombinant scFv genes previously sorted by yeast-display were cloned back into the phagemid display vector pDAN5 (Sblattero and Bradbury, 2000), as a polyclonal pool, and transformed into E. coli carrying the M13cp-dg3 helper plasmid (Chasteen et al., 2006; Phipps et al., 2016). The polyclonal multivalent phage pools were then administered intravenously (i.v.) into breast tumor-or lung tumor-bearing mice. Tumor xenografts (NCI-H460 human lung cancer cells for EphA5) or isogenic tumors (Ef43.fgf4 murine breast cancer cells for GRP78), and control organs were collected after 3 hours to enrich for phage clones that exclusively localized to tumors in vivo (FIGS. 12D and 12E). The relative number of phage particles in tumor and control tissue samples was assessed by quantitative real-time PCR. Amplified scFv genes isolated from the tumors were recloned back into the original phage-display vector and used for serial rounds of selection in vivo. After three rounds, specific targeting of EphA5 (FIG. 12D) and GRP78-expressing tumors (FIG. 12E), compared to several negative control organs, was observed. Two non-mutually exclusive approaches were used to identify lead monoclonal antibody candidates: for GRP78-targeting antibodies, phage clones from the final round of in vivo selection were evaluated for binding to the cognate recombinant antigen. For EphA5-targeting antibodies, the enrichment of the tumor-homing clones was assessed by NGS and the top-ranking clones determined by frequency were chosen as the lead monoclonal antibody candidates. In both cases, monoclonal antibodies were verified by DNA sequencing and restriction enzyme digestion to be confirmed full-length scFvs, with no rearrangements, stop codons or frameshifts.

Validation of Tumor-Homing In Vivo

Figure 13:
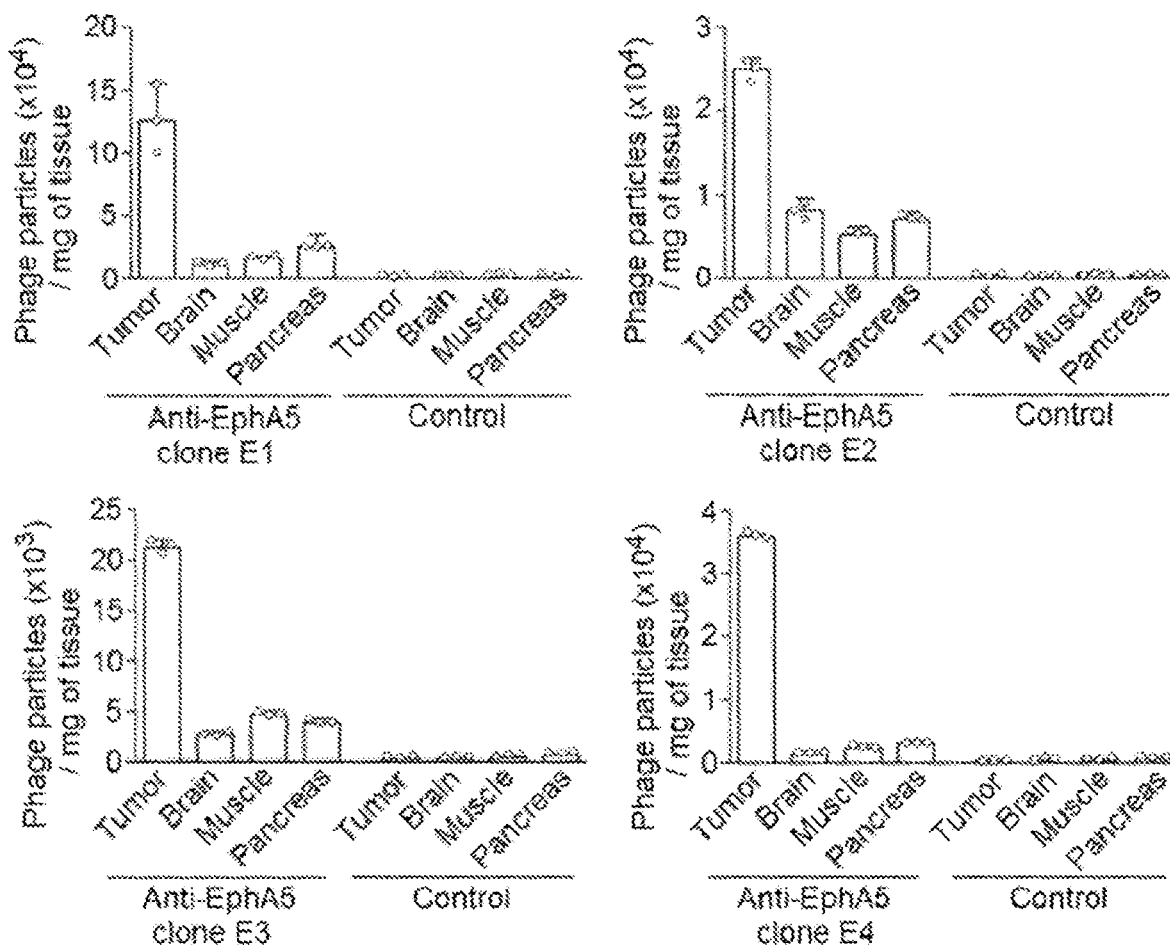
FIG. 13. Anti-Epha5 Monoclonal Antibodies Home To Human Lung Cancer Xenografts In Vivo. Selected anti-EphA5 antibody clones (termed E1-4) were tested individually for their ability to target EphA5-expressing tumors in a xenograft model of lung cancer (n=2). A representative graph is shown for each targeted phage clone. Phage displaying an antibody fragment against the viral protein M2 was used as negative control. Experiments were performed at least twice with similar results. A representative experiment is shown. Open circles represent individual data points.
Figure 14:
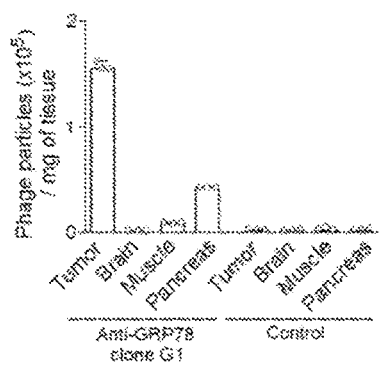
FIG. 14. Anti-GRP78 Monoclonal Antibodies Home To Isogenic Breast Tumors In Vivo. Selected anti-GRP78 antibody clones (termed G1-3) were tested individually for their ability to target an isogenic model of mammary cancer expressing cell surface GRP78 (n=2). A representative graph is shown for each targeted phage clone. Phage displaying an antibody fragment against the viral protein M2 was used as a negative control. Experiments were performed at least twice with similar results. A representative experiment is shown. Open circles represent individual data points.
Figure 14:
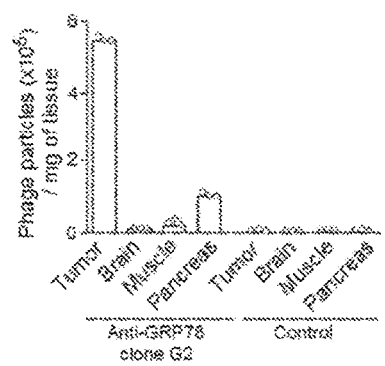
Figure 14:
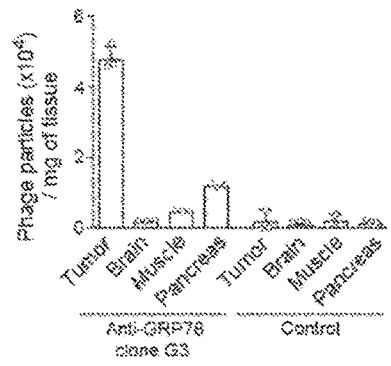

A total of four scFv clones against EphA5 (termed E1-4) and three against GRP78 (termed G1-3) were selected for functional studies (FIG. 22). Monoclonal antibodies were again displayed multivalently on phage, and tested individually for their ability to home and localize to tumors in vivo after i.v. administration. Phage displaying a scFv antibody against M2 (Gabbard et al., 2009), a conserved influenza virus protein, served as a standard negative control. Individual phage clones were administered i.v. in tumor-bearing mice and tumor tissue and control organs were recovered after 3 hours (FIGS. 13 and 14. Relative quantification of phage particles in tissue samples revealed marked accumulation of EphA5-binding phage to EphA5-expressing tumors (FIG. 13. On the other hand, GRP78-binding phage homed and localized to GRP78-expressing tumors (FIG. 14), compared to several negative control organs (shown are brain, muscle, and pancreas). No tumor homing was detected by control phage (insertless phage and phage displaying a scFv antibody against M2) in either experimental tumor model.

Assessment of Functional Binding Specificity

Figure 15A:
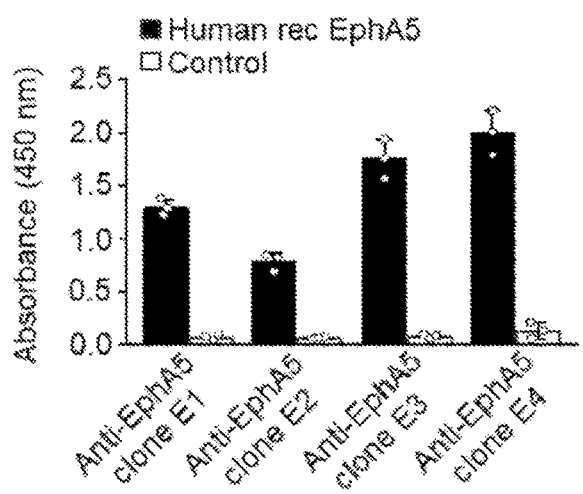
FIGS. 15A-15B. Characterization Of Scfv-Displaying Phage In Vitro (FIG. 15A) Selected anti-EphA5 clones or anti-GRP78 clones were tested individually for binding to recombinant antigens. Negative controls included an anti-M2 clone and BSA. Open circles represent individual data points.
Figure 15A:
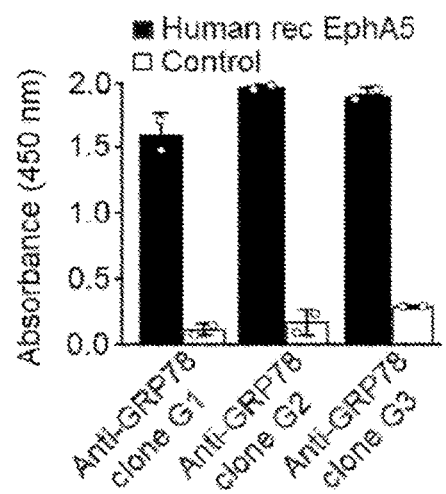
Figure 15B:
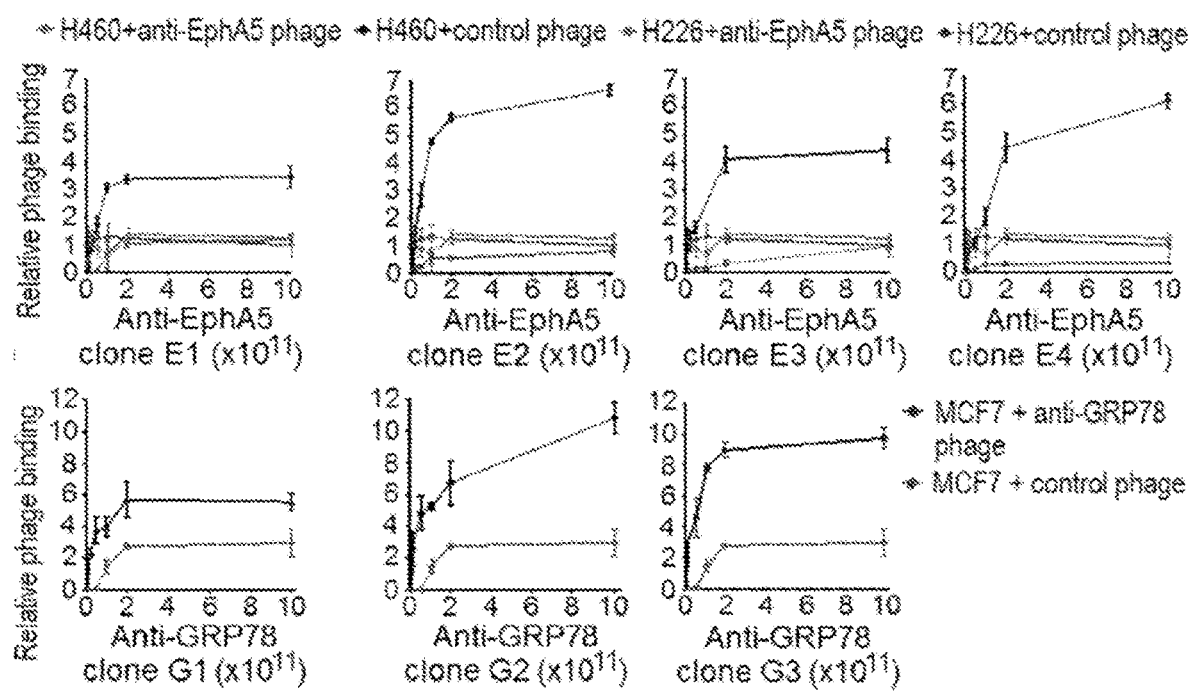
Figure 17:
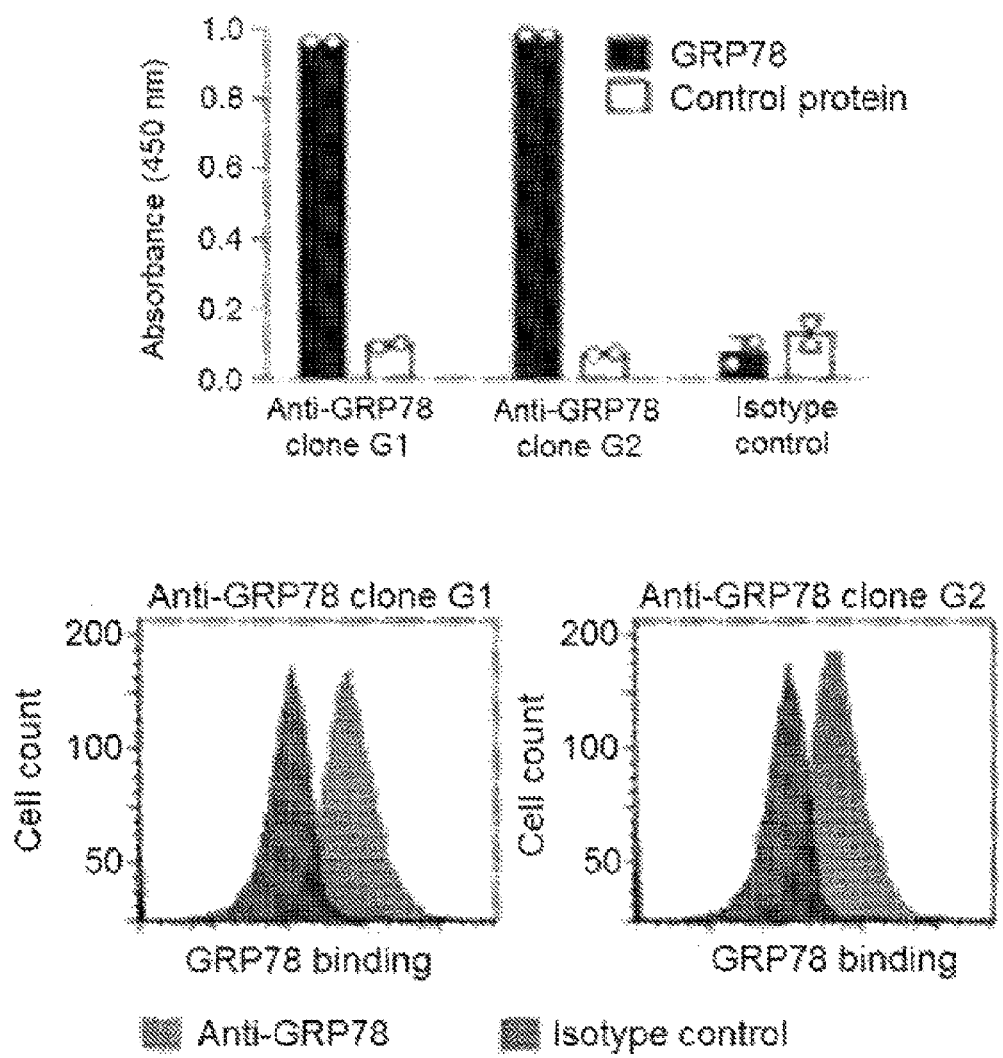
FIG. 17. Validation of Anti-GRP78 scfv-Fc Binding Specificity In Vitro. Anti-GRP78 scFv-Fc agents produced in yeast were tested by ELISA (FIG. 17, upper panel) and by flow cytometry (FIG. 17, lower panel) on Ef43.fgf4 cells. All clones showed binding specificity when compared to an isotype negative control antibody. Open circles represent individual data points.
Figure 18A:
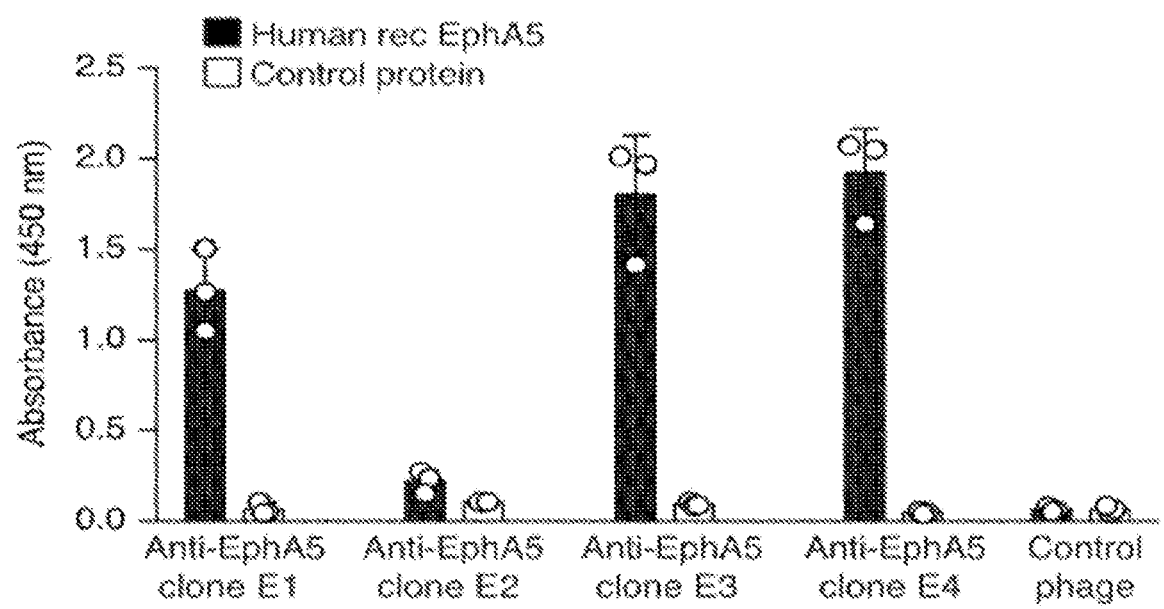
FIGS. 18A-18B. Validation of Anti-Epha5 scfv-Fcs In Vitro. The anti-EphA5 scFv-Fcs produced in CHO cells were tested by ELISA (A) and whole-cell ELISA (B) on EphA5 positive (H460) or negative (H226) lung cancer cells. All clones show binding specificity when compared to an isotype negative control. Open circles represent individual data points.
Figure 18B:
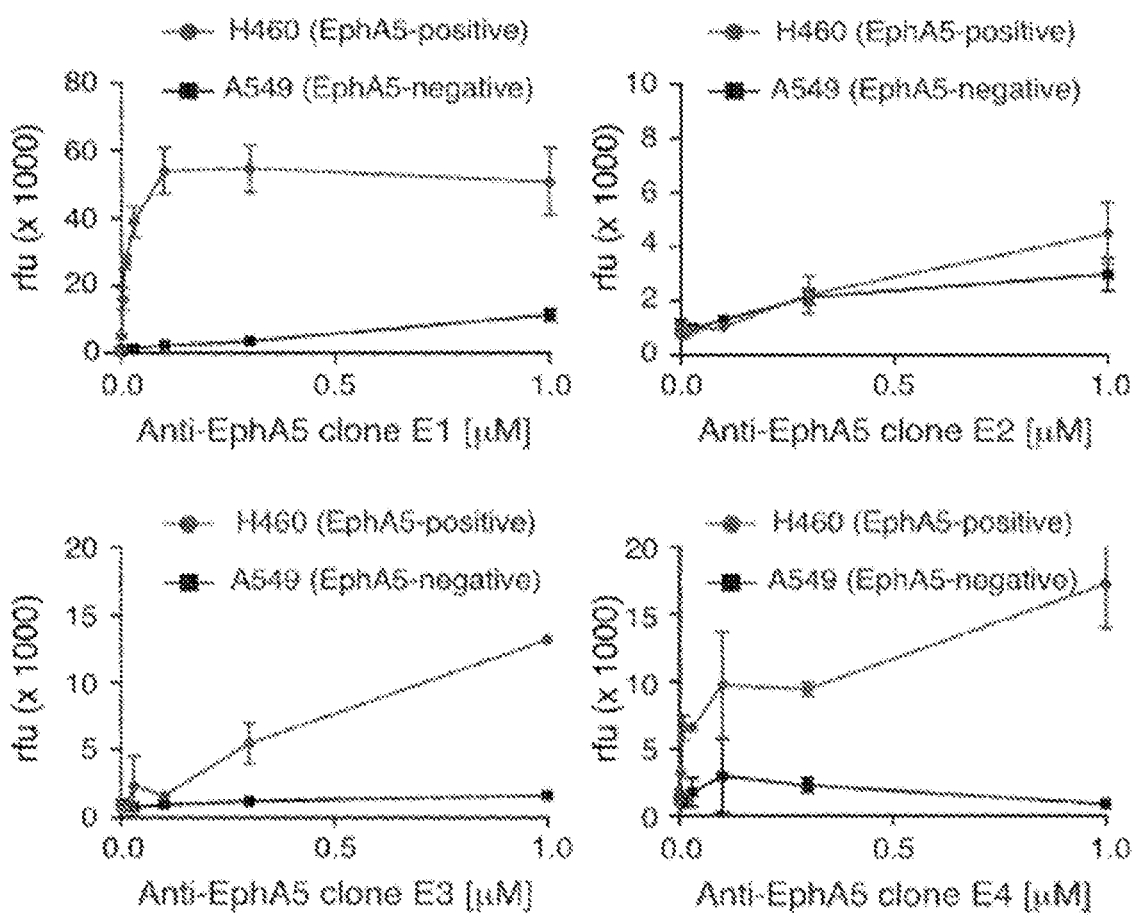
Figure 19:
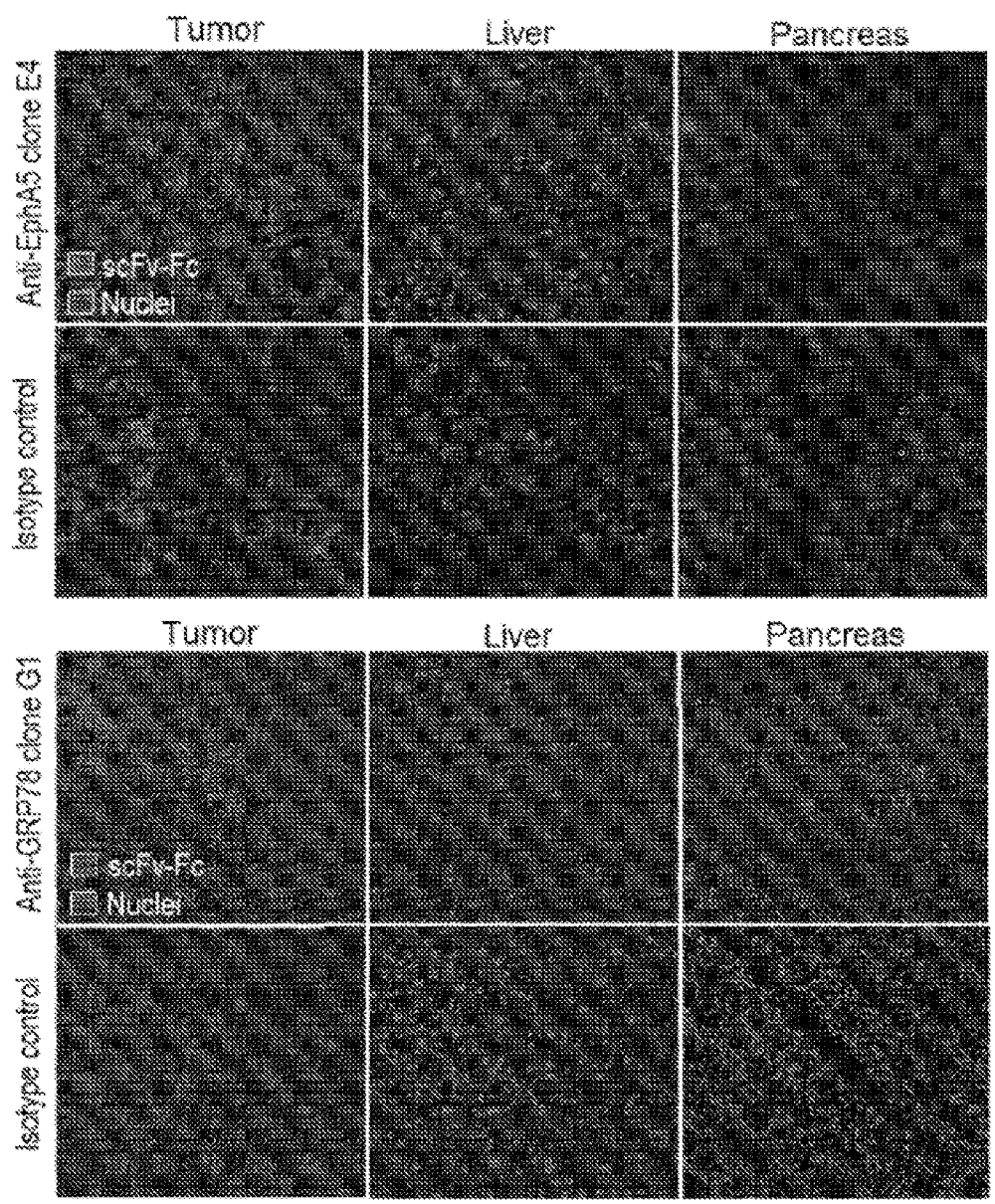
FIG. 19. Tumor Targeting In Vivo. The anti-EphA5 clone E4 scFv-Fc produced in CHO or the anti-GRP78 clone G1 scFv-Fc produced in S. cerevisia were administered i.v. into mice bearing human lung cancer xenografts or isogenic mammary tumor (n=2). After a circulation time no longer than 6 min, tumors and control organs were collected and processed for immunofluorescence with a Cy3-conjugated anti-Fc. Tumor targeting was observed whereas only background staining was detectable in negative control organs. An unrelated scFv-Fc served as negative control.

Having validated tumor-homing in vivo, we next evaluated binding specificity to recombinant proteins and endogenous corresponding targets expressed on the tumor cell surface. All individual monoclonal antibodies in multivalent phage-display format bound to their respective antigens, as measured by recombinant protein-based ELISA (FIGS. 15A-15B) and cell-based ELISA. Cells expressing surface EphA5 or GRP78 also showed receptor-mediated cell internalization of targeted phage clones. Negative controls included an insertless phage, phage displaying an unrelated scFv, and control cells. In order to test the antibodies as functional proteins, the scFvs were cloned into expression vectors in the scFv-human-Fc fusion format and were produced from either Chinese Hamster Ovary (CHO) cell culture supernatants, or the S. cerevisiae expression system, as indicated. Anti-GRP78 scFv-Fcs recognized human GRP78 on ELISA and flow cytometry (FIG. 17). Similarly, anti-EphA5 scFv-Fcs bound to immobilized recombinant EphA5, and endogenous EphA5 expressed on the cell surface (FIGs. 18A-18B). Moreover, when evaluated in vivo, the scFv-Fcs were able to infiltrate and localize to tumors after a 6 minutes circulation time, as assessed by immunofluorescence (FIG. 19). Taken together, these results indicate that the combination of in vitro screenings on recombinant cell surface receptors followed by in vivo selection of receptor-specific antibodies yields antibody clones with favorable on-target biodistribution.

Figure 20:
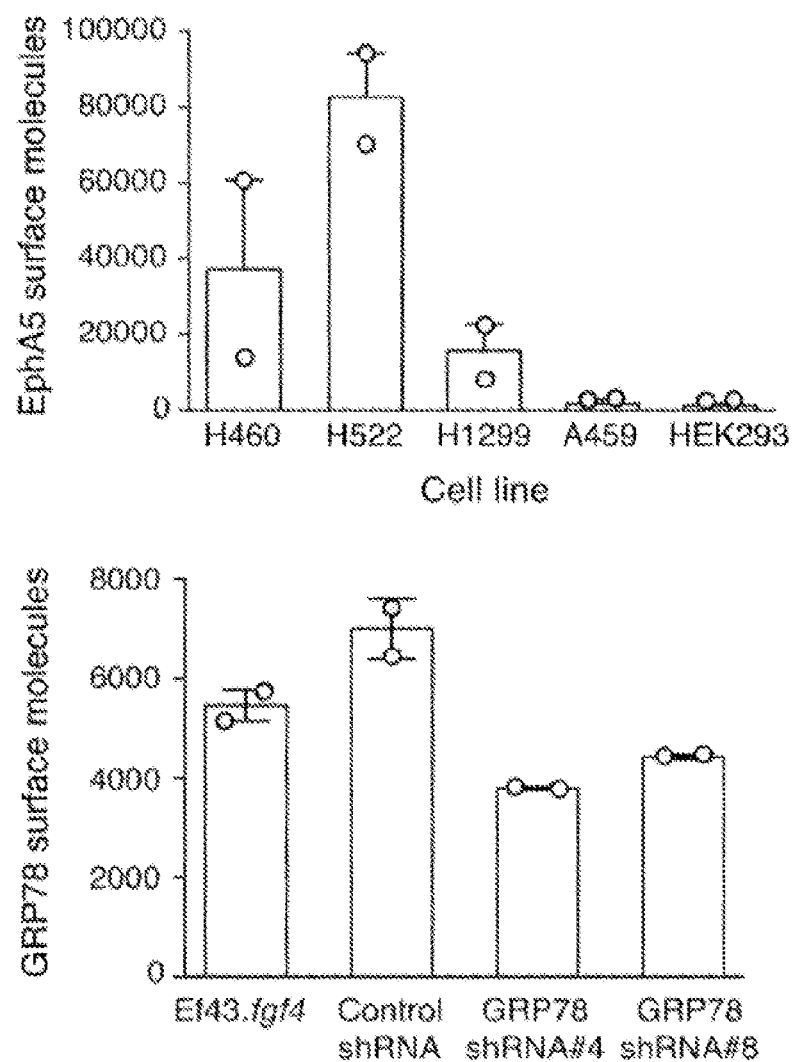
FIG. 20. Selection and Characterization of Tumor Cell Lines for In Vitro Cytotoxicity Assays The number of surface molecules was evaluated by flow cytometry-based quantitative analysis of antigen expression on the tumor cell surface.
Figure 21A:
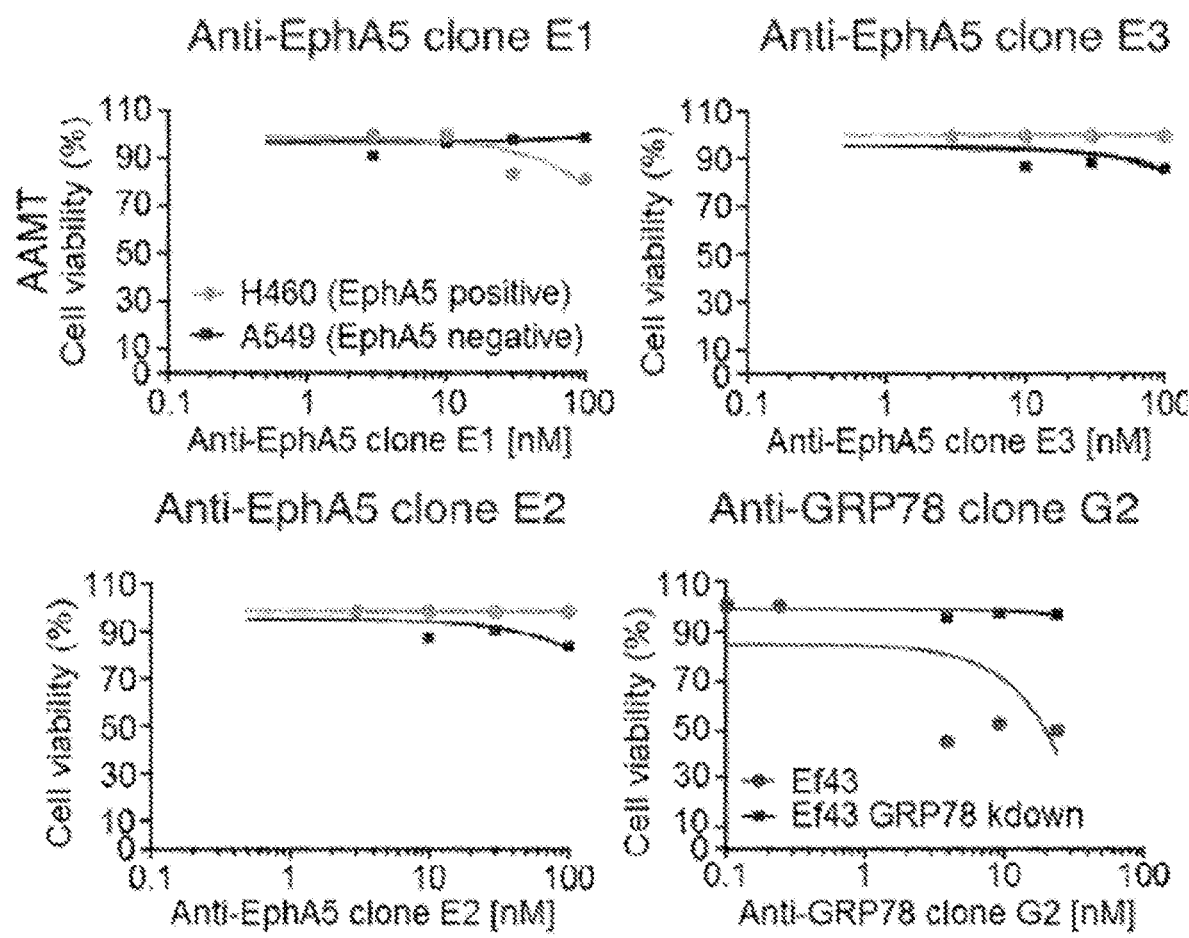
FIGS. 21A-21D. Complete Panel of Cytotoxic Profiles of Anti-Epha5 and Anti-GRP78 Monoclonal Antibodies Cytotoxicity was measured in real-time in presence of secondary Fab antibodies conjugated with AAMT, DMDM, MMAF, and DM1.
Figure 21B:
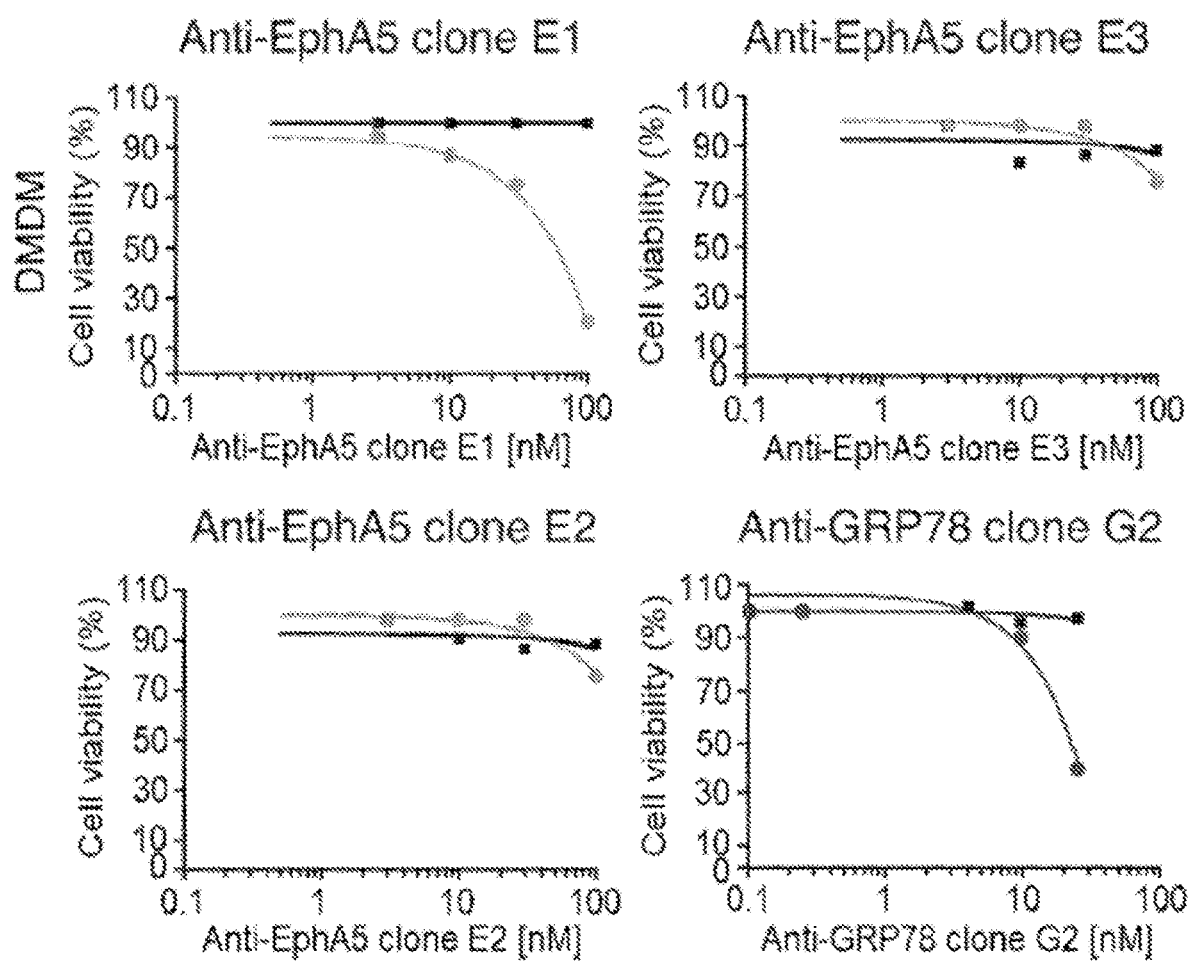
Figure 21C:
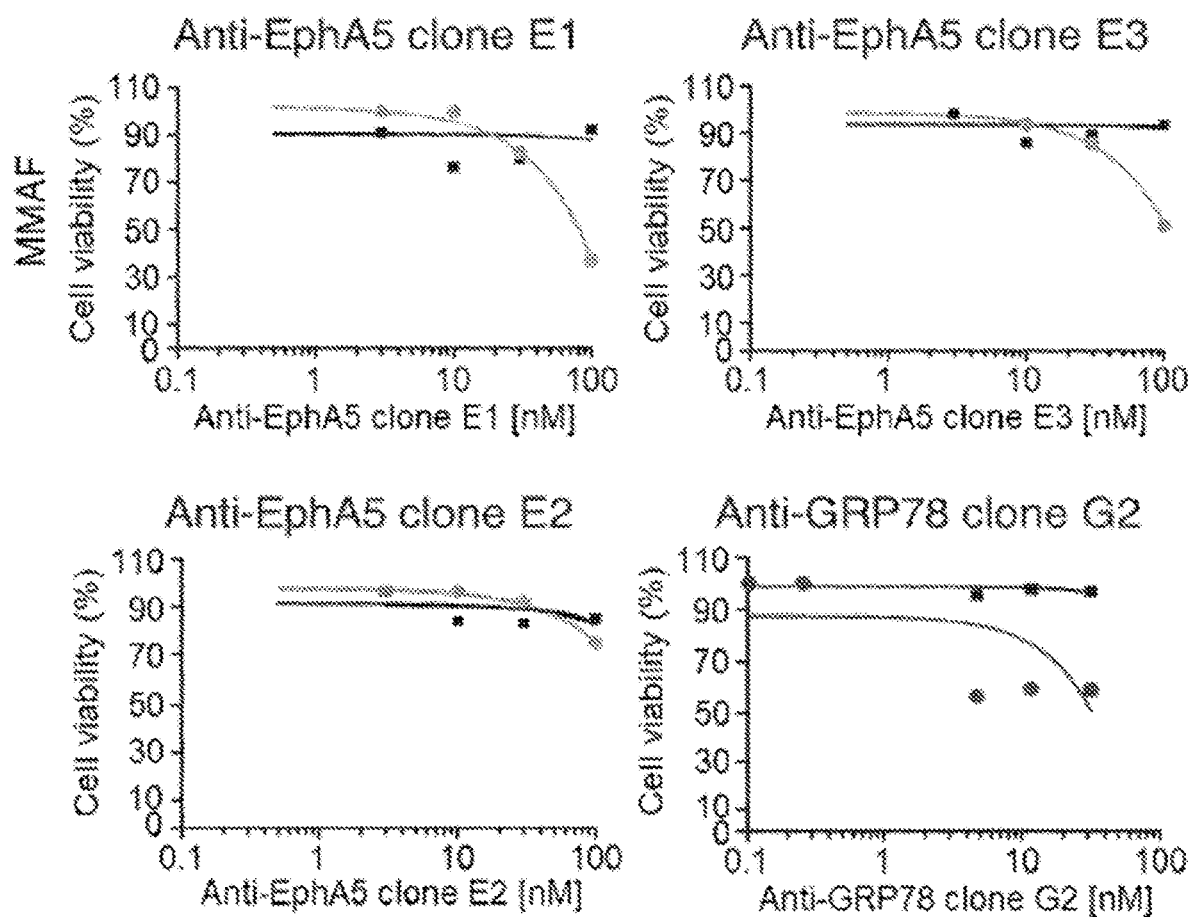
Figure 21D:
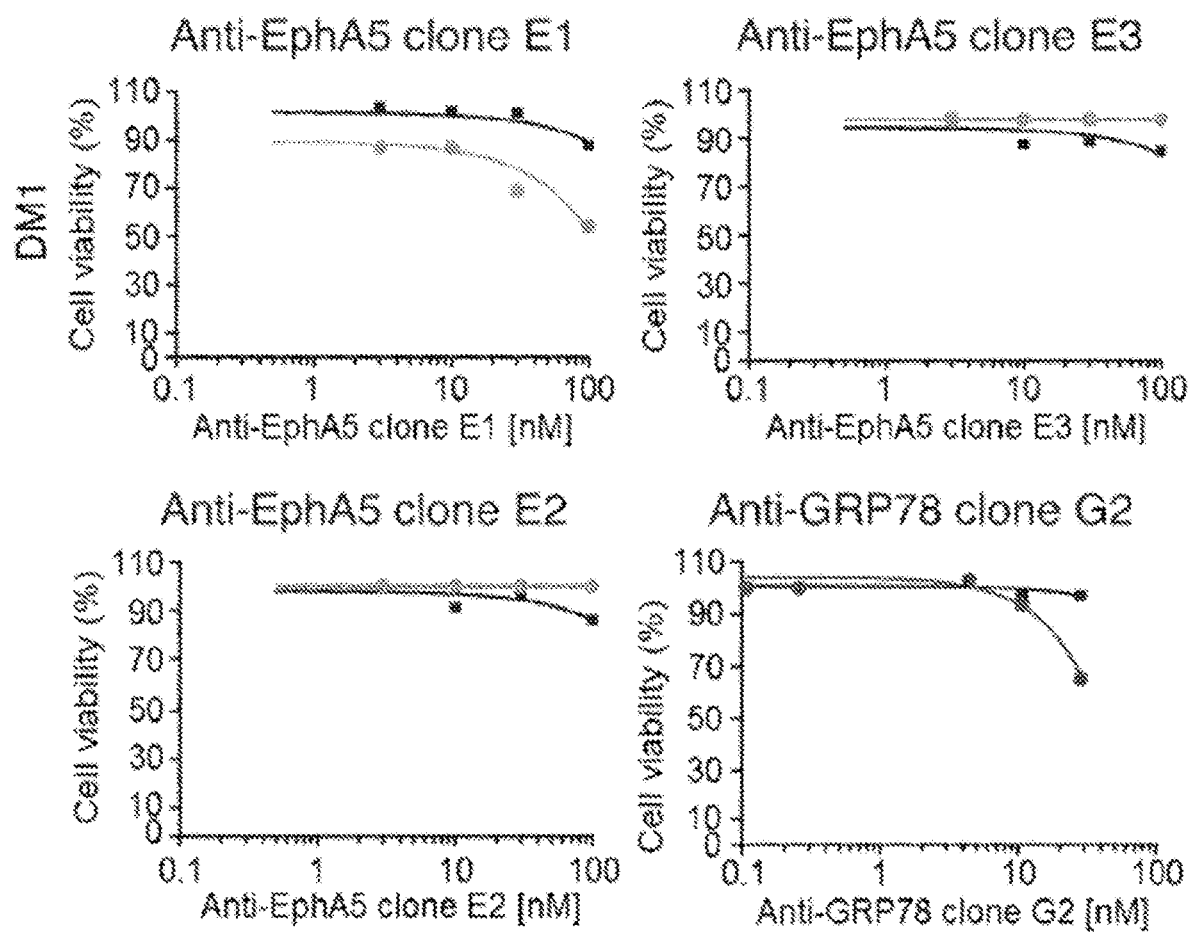

Monoclonal Antibodies have Specific Cytotoxicity Against Lung Cancer and Breast Cancer Cells ADCs were tested by using drug-conjugated secondary reagents recognizing the Fc region to deliver cytotoxic drugs. Monoclonal antibody candidates were prioritized based on binding and receptor-mediated internalization in target-expressing cells, and a cytotoxicity assay was used to determine the potency of the lead ADC candidates in a cell-based assay. Binding specificity and antigen-dependent efficacy were assessed with tumor cell lines expressing variable levels of the targets on their surfaces (FIG. 20). Negative controls included cells exposed to the primary scFv-Fc alone, cell lines depleted of EphA5 and GRP78, a non-specific primary scFv-Fc, and drug-conjugated secondary antibody alone.

Tumor cells were exposed to increasing concentrations of the lead scFv-Fcs, followed by secondary reagents conjugated to a representative panel of cytotoxic drugs: alpha-amanitin (AAMT), monomethyl auristatin F (MMAF), duocarmycin DM (DMDM), and emtansine (DM1). EphA5-expressing cells showed sensitivity to the scFv-Fc E4, when combined with all cytotoxic drugs. In particular, a clear concentration-dependent response at a low nanomolar range was observed for both AAMT and DMDM, supporting the functional retention of both receptor-binding specificity and cell internalization attributes. Similarly, the anti-GRP78 scFv-Fc G1 was found most efficient at inducing cell death, although at a higher nanomolar range. Control tumor cells were not affected under the same experimental conditions. Incubation with an irrelevant negative control scFv-Fc or drug-conjugated secondary antibody alone did not result in detectable tumor cell death. A complete panel of ADC experiments is depicted for reference (FIGS. 21A-21D).

DISCUSSION

A long-term goal of monoclonal antibody-based drug development is to produce recombinant human monoclonal antibodies with the lowest expected risk of immunogenicity. This is usually carried out by immunization of transgenic mice (Bruggemann et al., 2015) for production of human antibodies, humanization (Jones et al., 1986; Morrison et al., 1984; Queen et al., 1989; Riechmann et al., 1988) of murine antibodies (Gerhard et al., 1978; Kohler and Milstein, 1975; Koprowski et al., 1977; Pasqualini and Arap, 2004), or in vitro display methods, particularly phage (Marks et al., 1991) and/or yeast-display (Boder and Wittrup, 1997). The latter method does not depend on immunization, and may be used to identify human monoclonal antibodies directly from large naïve human libraries (Sblattero and Bradbury, 2000). The inventors have recently combined these two complementary antibody display platforms into a selection strategy that provides two key potential advantages over either platform alone: the ability to screen a vast number of clones in a single experiment, and to tailor the selection for precise functional attributes (Ferrara et al., 2012).

In the present application, the inventors introduce the SPARTA methodology, which serially integrates a two-step strategy based on in vitro screening and in vivo selection, to yield a robust monoclonal antibody discovery pipeline. Technical improvements include the recloning of sorted yeast-display antibodies back into our phage display vector (Sblattero and Bradbury, 2000), displaying them in a multivalent format (Chasteen et al., 2006), administering them systemically into tumor-bearing mice and isolating those that homed to tumors. The in vitro screening selections resulted in a range of hundreds of human recombinant antibodies against EphA5 and GRP78, while the in vivo functional selection identified those antibodies from the polyclonal pool able to recognize cell surface-associated targets within their in vivo context.

The use of two non-mutually exclusive approaches served to reduce the number of candidate targeted monoclonal antibodies into a practical biological number that could then be functionally evaluated. Another rational for our choice was to show the robustness and versatility of SPARTA and, to have an initial glimpse of whether or not one of these two empiric strategies might be either qualitatively superior and quantitatively cost-effective. First, a stochastic approach was applied to the GRP78-targeting selection, where a random screening of individual clones (n=45) led to the identification of three different scFvs. In the case of EphA5 we carried out deep NGS before and after each step of selection in vivo, allowing us to identify EphA5-binding clones that were highly enriched in the tumor. With either of these two independent approaches, we were able to isolate several different antibodies for each target that homed specifically and localized at the corresponding tumor models. These candidates were further investigated as phage-displayed monoclonal antibodies individually, and were shown to: (i) bind to their respective antigens; (ii) bind tumor lines expressing the antigens on their cell surface membrane; and (iii) undergo receptor-mediated internalization into target-expressing tumor cells. Together, these data provide strong evidence that SPARTA produces targeted monoclonal antibodies with translation potential since the efficacy of monoclonal antibody-based therapy relies on their selective uptake by cancer cells. When produced in the scFv-Fc format, antibody fusions retained all the binding functions of the original scFvs and tumor cell death was uniquevocally demonstrated with ADCs (FIGS. 21A-21D).

In summary, this study establishes SPARTA as a robust methodology for prompt identification of tumor-targeting human recombinant monoclonal antibodies with high specificity against established cell surface antigens. The results presented herein show that SPARTA may well become a methodology-of-choice to develop therapeutic antibodies from large human monoclonal antibody libraries.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, as well as other references cited in the present application, to the extent that they provide exemplary procedural or other details supplementary to those set forth herein, are specifically incorporated herein by reference.

EphA5 and GRP78 References

WO 2012/040472
Arap et al., 2004, Cancer Cell 6(3): 275-284
Daneshmand et al., 2007, Human Pathology 38(10): 1547-1552
Giaginis et al. (2010) Clinical significance of ephrin (eph)-A1, -A2, -a4, -a5 and -a7 receptors in pancreatic ductal adenocarcinoma. Pathol. Oncol. Res. 16,267-276.
Lee et al., 2006, Cancer Research 66(16): 7849-7853
Lee, 2014, Nature Rev Cancer 14(4): 263-276
Murai et al. (2010)Frequent epigenetic inactivation of the receptor tyrosine kinase EphA5 by promoter methylation in human breast cancer. Hum. Pathol. 41,48-58.
Pasquale E. B. (2008) Eph-ephrin bidirectional signaling in physiology and disease. Cell 133, 38-52.
Pasquale E. B. (2010) Eph receptors and ephrins in cancer: bidirectional signalling and beyond. Nat. Rev. Cancer 10, 165-180.
Pejovic et al. (2009) Expression profiling of the ovarian surface kinome reveals candidate genes for early neoplastic changes. Transl. Oncol. 2, 341-349.
Pitulescu et al. Genes & Dev., 24:2480-2492, 2010.
Staquicini et al. (2015) Receptor tyrosine kinase EphA5 is a functional molecular target in human lung cancer. J Biol Chem. 290(12): 7345-59.
Taylor et al. (1994)Expression and developmental regulation of Ehk-1, a neuronal Elk-like receptor tyrosine kinase in brain. Neuroscience 63, 163-178.
Zhou R. (1997) Regulation of topographic projection by the Eph family receptor Bsk (EphA5) and its ligands. Cell Tissue Res. 290, 251-259.

SPARTA References

Andris-Widhopf, J., Steinberger, P., Fuller, R., Rader, C., & Barbas, C. F. (2011). Generation of human scFv antibody libraries: PCR amplification and assembly of light- and heavy-chain coding sequences. Cold Spring Harbor protocols, 2011(9).
Arap, M. A., Landenranta, J., Mintz, P. J., Hajitou, A., Sarkis, A. S., Arap, W., and Pasqualini, R. (2004). Cell surface expression of the stress response chaperone GRP78 enables tumor targeting by circulating ligands. Cancer Cell 6, 275-284.
Arap, W., Kolonin, M. G., Trepel, M., Landenranta, J., Cardó-Vila, M., Giordano, R. J., Mintz, P. J., Ardelt, P. U., Yao, V. J., Vidal, C. I., et al. (2002). Steps toward mapping the human vasculature by phage display. Nat. Med. 8, 121-127.
Arap, W., Pasqualini, R., and Ruoslahti, E. (1998). Cancer treatment by targeted drug delivery to tumor vasculature in a mouse model. Science 279, 377-380.

Barbas, C. F., Burton, D. R., Scott, j k, & Silverman, G. J. (2001). Phage Display: A Laboratory Manual. Cold Spring Harbor Laboratory Press.

Barnhart, K. F., Christianson, D. R., Hanley, P. W., Driessen, W. H., Bernacky, B. J., Baze, W. B., Wen, S., Tian, M., Ma, J., Kolonin, M. G., et al. (2011). A peptidomimetic targeting white fat causes weight loss and improved insulin resistance in obese monkeys. Sci. Transl. Med. 3, 108ra112.

Boder, E. T., and Wittrup, K. D. (1997). Yeast surface display for screening combinatorial polypeptide libraries. Nat. Biotechnol. 15, 553-557.

Boder, E. T., and Wittrup, K.D. (1998). Optimal screening of surface-displayed polypeptide libraries. Biotechnol. Prog. 14, 55-62.

Bruggemann, M., Osborn, M. J., Ma, B., Hayre, J., Avis, S., Lundstrom, B., and Buelow, R. (2015). Human antibody production in transgenic animals. Arch. Immunol. Ther. Exp. (Warsz) 63,101-108.

Carter, P., Smith, L., and Ryan, M. (2004). Identification and validation of cell surface antigens for antibody targeting in oncology. Endocr. Relat. Cancer 11, 659-687.

Chasteen, L., Ayriss, J., Pavlik, P., and Bradbury, A. R. (2006). Eliminating helper phage from phage display. Nucleic Acids Res. 34, e145.

Christianson, D. R., Ozawa, M. G., Pasqualini, R., and Arap, W. (2007). Techniques to decipher molecular diversity by phage display. Methods Mol. Biol. 357, 385-406.

D'Angelo, S., Glanville, J., Ferrara, F., Naranjo, L., Gleasner, C. D., Shen, X., Bradbury, A. R., and Kiss, C. (2014a). The antibody mining toolbox: an open source tool for the rapid analysis of antibody repertoires. mAbs 6, 160-172.

D'Angelo, S., Kumar, S., Naranjo, L., Ferrara, F., Kiss, C., and Bradbury, A. R. (2014b). From deep sequencing to actual clones. Protein Eng. Des. Sel. 27, 301-307.

Deramchia, K., Jacobin-Valat, M. J., Vallet, A., Bazin, H., Santarelli, X., Sanchez, S., Dos Santos, P., Franconi, J. M., Claverol, S., Bonetto, S., et al. (2012). In vivo phage display to identify new human antibody fragments homing to atherosclerotic endothelial and subendothelial tissues. Am. J. Pathol. 180, 2576-2589.

Dias-Neto, E., Nunes, D. N., Giordano, R. J., Sun, J., Botz, G. H., Yang, K., Setubal, J. C., Pasqualini, R., and Arap, W. (2009). Next-generation phage display: integrating and comparing available molecular tools to enable cost-effective high-throughput analysis. PloS One 4, e8338.

Dobroff, A. S., D'Angelo, S., Eckhardt, B. L., Ferrara, F., Staquicini, D. I., Cardó-Vila, M., Staquicini, F. I., Nunes, D. N., Kim, K., Driessen, W. H., et al. (2016). Towards a transcriptome-based theranostic platform for unfavorable breast cancer phenotypes. Proc. Natl. Acad. Sci. U S A. 113, 12780-12785.

Driessen, W. H., Bronk, L. F., Edwards, J. K., Proneth, B., Souza, G. R., Decuzzi, P., Pasqualini, R., and Arap, W. (2010). On the synergistic effects of ligand-mediated and phage-intrinsic properties during in vivo selection. Adv. Genet. 69, 115-133.

Ferrara, F., D'Angelo, S., Gaiotto, T., Naranjo, L., Tian, H., Graslund, S., Dobrovetsky, E., Hraber, P., Lund-Johansen, F., Saragozza, S., et al. (2015). Recombinant renewable polyclonal antibodies. mAbs 7, 32-41.

Ferrara, F., Naranjo, L. A., Kumar, S., Gaiotto, T., Mukundan, H., Swanson, B., and Bradbury, A. R. (2012). Using phage and yeast display to select hundreds of monoclonal antibodies: application to antigen 85, a tuberculosis biomarker. PloS One 7, e49535.

Ferrara, F., Staquicini, D. I., Driessen, W. H., D'Angelo, S., Dobroff, A. S., Barry, M., Lomo, L. C., Staquicini, F. I., Cardó-Vila, M., Soghomonyan, S., et al. (2016). Targeted molecular-genetic imaging and ligand-directed therapy in aggressive variant prostate cancer. Proc. Natl. Acad. Sci. U S A. 113, 12786-12791.

Gabbard, J., Velappan, N., Di Niro, R., Schmidt, J., Jones, C. A., Tompkins, S. M., and Bradbury, A. R. (2009). A humanized anti-M2 scFv shows protective in vitro activity against influenza. Protein Eng. Des. Sel. 22, 189-198.

Gerhard, W., Croce, C. M., Lopes, D., and Koprowski, H. (1978). Repertoire of antiviral antibodies expressed by somatic cell hybrids. Proc. Natl. Acad. Sci. U S A. 75, 1510-1514.

Hajitou, A., Pasqualini, R., and Arap, W. (2006). Vascular targeting: recent advances and therapeutic perspectives. Trends Cardiovasc. Med. 16, 80-88.

Hoogenboom, H. R., Griffiths, A. D., Johnson, K. S., Chiswell, D. J., Hudson, P., & Winter, G. (1991). Multisubunit proteins on the surface of filamentous phage: methodologies for displaying antibody (Fab) heavy and light chains. *Nucleic Acids Res,* 19(15), 4133-4137.

Huston, J. S., Levinson, D., Mudgett-Hunter, M., Tai, M. S., Novotný, J., Margolies, M. N., Ridge, R. J., et al. (1988). Protein engineering of antibody binding sites: recovery of specific activity in an anti-digoxin single-chain Fv analogue produced in *Escherichia coli. Proceedings of the National Academy of Sciences of the United States of America,* 85(16), 5879-83. Jones, P. T., Dear, P. H., Foote, J., Neuberger, M. S., and Winter, G. (1986). Replacing the complementarity-determining regions in a human antibody with those from a mouse. Nature 321, 522-525.

Kohler, G., and Milstein, C. (1975). Continuous cultures of fused cells secreting antibody of predefined specificity. Nature 256, 495-497.

Kolonin, M., Pasqualini, R., and Arap, W. (2001). Molecular addresses in blood vessels as targets for therapy. Curr. Opin. Chem. Biol. 5, 308-313.

Kolonin, M. G., Saha, P. K., Chan, L., Pasqualini, R., and Arap, W. (2004). Reversal of obesity by targeted ablation of adipose tissue. Nat. Med. 10, 625-632.

Kolonin, M. G., Sun, J., Do, K. A., Vidal, C. I., Ji, Y., Baggerly, K. A., Pasqualini, R., and Arap, W. (2006). Synchronous selection of homing peptides for multiple tissues by in vivo phage display. FASEB J. 20, 979-981.

Koprowski, H., Gerhard, W., and Croce, C. M. (1977). Production of antibodies against influenza virus by somatic cell hybrids between mouse myeloma and primed spleen cells. Proc. Natl. Acad. Sci. U S A. 74, 2985-2988.

Krag, D. N., Shukla, G. S., Shen, G. P., Pero, S., Ashikaga, T., Fuller, S., Weaver, D. L., Burdette-Radoux, S., and Thomas, C. (2006). Selection of tumor-binding ligands in cancer patients with phage display libraries. Cancer Res. 66, 7724-7733.

Krebber, A., Bornhauser, S., Burmester, J., Honegger, A., Willuda, J., Bosshard, H. R., & Pluckthun, A. (1997). Reliable cloning of functional antibody variable domains from hybridomas and spleen cell repertoires employing a reengineered phage display system. J Immunol Methods, 201(1), 35-55.

Marks, J. D., & Bradbury, A. (2004). PCR cloning of human immunoglobulin genes. *Methods in molecular biology* (Clifton, N.J.), 248, 117-34.

Marks, J. D., Hoogenboom, H. R., Bonnert, T. P., McCafferty, J., Griffiths, A. D., and Winter, G. (1991). By-passing immunization. Human antibodies from V-gene libraries displayed on phage. J. Mol. Biol. 222, 581-597.

Morrison, S. L., Johnson, M. J., Herzenberg, L. A., and Oi, V. T. (1984). Chimeric human antibody molecules: mouse antigen-binding domains with human constant region domains. Proc. Natl. Acad. Sci. U S A. 81, 6851-6855.

Ozawa, M. G., Zurita, A. J., Dias-Neto, E., Nunes, D. N., Sidman, R .L., Gelovani, J. G., Arap, W., and Pasqualini, R. (2008). Beyond receptor expression levels: the relevance of target accessibility in ligand-directed pharmacodelivery systems. Trends Cardiovasc. Med. 18, 126-132.

Pasqualini, R., and Arap, W. (2002). Profiling the molecular diversity of blood vessels. Cold Spring Harb. Symp. Quant. Biol. 67, 223-225.

Pasqualini, R., and Arap, W. (2004). Hybridoma-free generation of monoclonal antibodies. Proc. Natl. Acad. Sci. U S A. 101, 257-259.

Pasqualini, R., and Ruoslahti, E. (1996). Organ targeting in vivo using phage display peptide libraries. Nature 380, 364-366.

Phipps, M. L., Lillo, A. M., Shou, Y., Schmidt, E. N., Paavola, C. D., Naranjo, L., Bemdich, S., Swanson, B. I., Bradbury, A. R., and Martinez, J. S. (2016). Beyond helper phage: using "helper cells" to select peptide affinity ligands. PLoS One 11, e0160940.

Queen, C., Schneider, W. P., Selick, H. E., Payne, P. W., Landolfi, N. F., Duncan, J. F., Avdalovic, N. M., Levitt, M., Junghans, R. P., and Waldmann, T. A. (1989). A humanized antibody that binds to the interleukin 2 receptor. Proc. Natl. Acad. Sci. U S A. 86, 10029-10033.

Rajotte, D., Arap, W., Hagedorn, M., Koivunen, E., Pasqualini, R., and Ruoslahti, E. (1998). Molecular heterogeneity of the vascular endothelium revealed by in vivo phage display. J. Clin. Invest. 102, 430-437.

Riechmann, L., Clark, M., Waldmann, H., and Winter, G. (1988). Reshaping human antibodies for therapy. Nature 332, 323-327.

Sanchez-Martin, D., Sorensen, M.D., Lykkemark, S., Sanz, L., Kristensen, P., Ruoslahti, E., and Alvarez-Vallina, L. (2015). Selection strategies for anticancer antibody discovery: searching off the beaten path. Trends Biotechnol. 33, 292-301.

Sblattero, D., and Bradbury, A. (2000). Exploiting recombination in single bacteria to make large phage antibody libraries. Nat. Biotechnol. 18, 75-80.

Schaefer, J. V, Honegger, A., & Pluckthun, A. (2010). Construction of scFv Fragments from Hybridoma or Spleen Cells by PCR Assembly. (R. Kontermann & S. Dübel, Eds.)

Shukla, G .S., Krag, D. N., Peletskaya, E. N., Pero, S. C., Sun, Y. J., Carman, C. L., McCahill, L. E., and Roland, T.A. (2013). Intravenous infusion of phage-displayed antibody library in human cancer patients: enrichment and cancer-specificity of tumor-homing phage-antibodies. Cancer Immunol. Immunother. 62, 1397-1410.

Staquicini, F. I., Cardó-Vila, M., Kolonin, M. G., Trepel, M., Edwards, J. K., Nunes, D. N., Sergeeva, A., Efstathiou, E., Sun, J., Almeida, N. F., et al. (2011a). Vascular ligand-receptor mapping by direct combinatorial selection in cancer patients. Proc. Natl. Acad. Sci. U S A. 108, 18637-18642.

Staquicini, F. I., Moeller, B. J., Arap, W., and Pasqualini, R. (2010). Combinatorial vascular targeting in translational medicine. Proteomics Clin. Appl. 4, 626-632.

Staquicini, F. I., Ozawa, M.G., Moya, C. A., Driessen, W. H., Barbu, E. M., Nishimori, H., Soghomonyan, S., Flores, L. G., 2nd, Liang, X., Paolillo, V., et al. (2011b). Systemic combinatorial peptide selection yields a non-canonical iron-mimicry mechanism for targeting tumors in a mouse model of human glioblastoma. J. Clin. Invest. 121, 161-173.

Staquicini, F. I., Qian, M. D., Salameh, A., Dobroff, A. S., Edwards, J. K., Cimino, D. F., Moeller, B. J., Kelly, P., Nunez, M. I., Tang, X., et al. (2015). Receptor tyrosine kinase EphA5 is a functional molecular target in human lung cancer. J. Biol. Chem. 290, 7345-7359.

What is claimed is:

1. An isolated monoclonal antibody, wherein the antibody specifically binds to GRP78 (78 kDa glucose-regulated protein) and comprises:
a heavy chain variable region (VH) comprising a VH CDR1 having the amino acid sequence set forth in SEQ ID NO: 39, a VH CDR2 having the amino acid sequence set forth in SEQ ID NO: 40, and a VH CDR3 having the amino acid sequence set forth in SEQ ID NO: 41;
and
a light chain variable region (VL) comprising a VL CDR1 having the amino acid sequence set forth in SEQ ID NO: 42, a VL CDR2 having the amino acid sequence set forth in SEQ ID NO: 43, and a VL CDR3 having the amino acid sequence set forth in SEQ ID NO: 44.

2. The antibody of claim 1, wherein the antibody comprises a VH having an amino acid sequence that is at least 90% identical to SEQ ID NO: 37 and a VL having an amino acid sequence that is at least 90% identical to SEQ ID NO: 38.

3. The antibody of claim 1, wherein the antibody comprises a VH having an amino acid sequence that is at least 95% identical to SEQ ID NO: 37 and a VL having an amino acid sequence that is at least 95% identical to SEQ ID NO: 38.

4. The antibody of claim 1, wherein the antibody comprises the VH having the amino acid sequence set forth in SEQ ID NO: 37 and the VL having the amino acid sequence set forth in SEQ ID NO: 38.

5. The antibody of claim 1, wherein the antibody is a recombinant antibody.

6. The antibody of claim 1, wherein the antibody is an IgG, IgM, IgA, or an antigen binding fragment thereof.

7. The antibody of claim 1, wherein the antibody is a Fab', a F(ab')$_2$, a F(ab')$_3$, a monovalent scFv, or a bivalent scFv.

8. The antibody of claim 1, wherein the antibody is a full length antibody.

9. The antibody of claim 1, wherein the antibody is a human, humanized antibody, or de-immunized antibody.

10. An immunoconjugate comprising the antibody of claim 1 conjugated to at least one effector moiety selected from an imaging agent, a chemotherapeutic agent, a toxin, and a radionuclide.

11. The immunoconjugate of claim 10, wherein there is one effector moiety, and wherein the one effector moiety is a toxin.

12. The immunoconjugate of claim 11, wherein the toxin is auristatin or monomethyl auristatin E (MMAE).

13. The immunoconjugate of claim 12, wherein the toxin is MMAE.

14. A composition comprising the antibody of claim 1 and at least one pharmaceutically acceptable carrier.

15. A composition comprising the immunoconjugate of claim 10 and at least one pharmaceutically acceptable carrier.

16. A composition comprising the immunoconjugate of claim 12 and at least one pharmaceutically acceptable carrier.

17. A composition comprising the immunoconjugate of claim 13 and at least one pharmaceutically acceptable carrier.

18. A method of treating or ameliorating a cancer in a subject, the method comprising administering to the subject an effective amount of the antibody of claim 1.

19. A method of treating or ameliorating a cancer in a subject, the method comprising administering to the subject an effective amount of the immunoconjugate of claim 10.

20. A method of detecting a cancer in a subject, comprising testing for the presence of elevated GRP78 in a sample from the subject relative to a control, wherein the testing comprises contacting the sample with the antibody of claim 1.

21. A method of detecting GRP78, neutralizing GRP78, or counteracting the effects of GRP78, the method comprising contacting the GRP78 with the antibody of claim 1.

22. The method of claim 21, wherein the GRP78 is in a cultured cell.

23. The method of claim 21, wherein the GRP78 is on a surface of a cell.

24. The method of claim 22, wherein the GRP78 is in a subject.

25. The method of claim 24, wherein the GRP78 is in or on a surface of a cancer cell in the subject.

26. The method of claim 25, wherein the subject is a human.

* * * * *